US012679829B2

(12) United States Patent
Chu et al.

(10) Patent No.: US 12,679,829 B2
(45) Date of Patent: Jul. 14, 2026

(54) FUSED IMIDAZOLE DERIVATIVES AS IL-17 MODULATORS

(71) Applicant: UCB Biopharma SRL, Brussels (BE)

(72) Inventors: Shuyu Chu, Slough (GB); Helen Tracey Horsley, Slough (GB); James Thomas Reuberson, Slough (GB); Richard David Taylor, Slough (GB); Zhaoning Zhu, Slough (GB); Rose Elizabeth Chappell, Abingdon (GB); Gregory William Haslett, Slough (GB); Adam Peter Smalley, Slough (GB); Nathaniel Julius Thomas Monck, Abingdon (GB); Gareth Neil Brace, Abingdon (GB); Prafulkumar Tulshibhai Chovatia, Abingdon (GB)

(73) Assignee: UCB Biopharma SRL, Brussels (BE)

( * ) Notice: Subject to any disclaimer, the term of this patent is extended or adjusted under 35 U.S.C. 154(b) by 1117 days.

(21) Appl. No.: 17/621,877

(22) PCT Filed: Jun. 24, 2020

(86) PCT No.: PCT/EP2020/067758
§ 371 (c)(1),
(2) Date: Dec. 22, 2021

(87) PCT Pub. No.: WO2020/260425
PCT Pub. Date: Dec. 30, 2020

(65) Prior Publication Data

US 2022/0242855 A1 Aug. 4, 2022

(30) Foreign Application Priority Data

Jun. 26, 2019 (GB) ...................................... 1909191

(51) Int. Cl.

| | |
|---|---|
| ***C07D 405/14*** | (2006.01) |
| ***A61K 31/4245*** | (2006.01) |
| ***A61K 31/4353*** | (2006.01) |
| ***A61K 31/4439*** | (2006.01) |
| ***A61K 31/497*** | (2006.01) |
| ***A61K 31/501*** | (2006.01) |
| ***A61K 31/519*** | (2006.01) |
| ***A61K 45/06*** | (2006.01) |

(Continued)

(52) U.S. Cl.
CPC ........ *C07D 405/14* (2013.01); *A61K 31/4245* (2013.01); *A61K 31/4353* (2013.01); *A61K 31/4439* (2013.01); *A61K 31/497* (2013.01); *A61K 31/501* (2013.01); *A61K 31/519* (2013.01); *A61K 45/06* (2013.01); *C07D 417/14* (2013.01); *C07D 487/04* (2013.01); *C07D 498/04* (2013.01)

(58) Field of Classification Search
CPC .. C07D 405/14; C07D 417/14; C07D 487/04; C07D 498/04; A61K 31/4245; A61K 31/4353; A61K 31/4439; A61K 31/497; A61K 31/501; A61K 31/519; A61K 45/06
See application file for complete search history.

(56) References Cited

U.S. PATENT DOCUMENTS

| | | | |
|---|---|---|---|
| 6,649,631 | B1 | 11/2003 | Orme et al. |
| 2002/0107392 | A1 | 8/2002 | Renhowe |

(Continued)

FOREIGN PATENT DOCUMENTS

| | | |
|---|---|---|
| JP | 2000-509719 | 12/1997 |
| JP | 2001-510450 | 7/2001 |

(Continued)

OTHER PUBLICATIONS

Ito, Journal of Medicinal Chemistry, 2018, 61, 7710-7728 (Year: 2018).*
Johannes, Chem Med Chem Communications, 2018, 13, 231-235 (Year: 2018).*
Bibian, Bioorganic and Medicinal Chemistry Letters 23, 2013, 4374-4380 (Year: 2013).*
Liu, Current Opinion in Rheumatology, May 2019; 31 (3): 307-315 (Year: 2019).*
STN Registry No. 2249628-87-1 (Year: 2018).*
STN Registry No. 1428141-54-1 (Year: 2013).*
STN Registry No. 1440305-73-6 (Year: 2013).*

(Continued)

*Primary Examiner* — Andrew D Kosar
*Assistant Examiner* — Phillip Matthew Rzeczycki
(74) *Attorney, Agent, or Firm* — McDonnell Boehnen Hulbert & Berghoff LLP

(57) ABSTRACT

A series of substituted fused bicyclic imidazole derivatives of formula (I), including benzimidazole derivatives and analogues thereof, being potent modulators of human IL-17 activity, are accordingly of benefit in the treatment and/or prevention of various human ailments including inflammatory and autoimmune disorders, wherein i. a. A represents C—$R^1$ or N; B represents C—$R^2$ or N; D represents C—$R^3$ or N; E represents C—$R^4$ or N; Z represents —CH($R^5$)N(H)$CH_2R^6$, —CH($R^5$)N(H)S(O)$_2R^6$, —C(=C$R^{5a}R^{5b}$)N(H)C(O)$R^6$, —CH($R^5$)$R^7$, —CH($R^5$)N(H)$R^7$ or —CH($R^5$)C(O)N(H)$R^7$; $R^0$ represents hydrogen or $C_{1-6}$ alkyl.

(I)

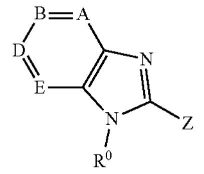

14 Claims, No Drawings

(51) Int. Cl.
*C07D 417/14* (2006.01)
*C07D 487/04* (2006.01)
*C07D 498/04* (2006.01)

(56) References Cited

U.S. PATENT DOCUMENTS

2011/0245257 A1 10/2011 Cushing et al.
2015/0274729 A1* 10/2015 Roush .................. C07D 473/34
514/263.21

FOREIGN PATENT DOCUMENTS

| | | | | |
|---|---|---|---|---|
| WO | 1997/48697 | | 12/1997 | |
| WO | 1998/17267 | | 4/1998 | |
| WO | 2009/089036 | A2 | 7/2009 | |
| WO | 2009/110520 | | 9/2009 | |
| WO | 2013/116682 | A1 | 8/2013 | |
| WO | WO-2014052640 | A1 * | 4/2014 | ............. A61K 31/10 |
| WO | 2014/066726 | A2 | 5/2014 | |
| WO | WO-2016027249 | A1 * | 2/2016 | ......... A61K 31/4375 |
| WO | 2018/229079 | A1 | 12/2018 | |
| WO | 2019/138017 | A1 | 7/2019 | |

OTHER PUBLICATIONS

STN Registry No. 1462335-81-4 (Year: 2013).*
STN Registry No. 2227476-83-5 (Year: 2018).*
STN Registry No. 2227476-84-6 (Year: 2018).*
STN Registry No. 1164543-11-6 (Year: 2009).*
STN Registry No. 1164551-28-3 (Year: 2009).*
STN Registry No. 1261141-30-3 (Year: 2011).*
STN Registry No. 376373-61-4 (Year: 2001).*
STN Registry No. 897446-03-6 (Year: 2006).*
STN Registry No. 1026017-81-1 (Year: 2008).*
STN Registry No. 1186539-72-9 (Year: 2009).*
Kaushik, Med Chem Research, 2012, 21:459-467 (Year: 2012).*
Dutta, Alokdut et al, Effect of optimized structure and electronic properties of some benzimidazole derivatives on corrosion inhibition of mild steel in hydrochloric acid medium: Electrochemical and theoretical studies, Journal of Chemical Sciences, 2015, 921-929, vol. 127 No. 5.
Gaffen, Sarah L., An overview of IL-17 function and signaling, Cytokine, 2008, 402-407, 43.
Ilkay Yildiz-Oren et al, Synthesis and structure-activity relationships of new antimicrobial active multisubstituted penzazole derivatives, European Journal of Medicinal Chemistry, 2004, 291-298, vol. 39 No. 3.
Kamaras, Peter et al, Synthesis of an unsymmetrical dinucleating ligand that leads to an Asymmetir dicopper (II) complex having different donor sets at each copper, J. Am. Chem. Soc, 1994, 10334-10335, vol. 116 No. 22.
Kong, Xianqi et al, Structure-Activity relationships of 1,2-Disubstituted Benzimidazoles: Selective Inhibition of Heme Oxygenase-2 activity, Chem Med Chem, 2015, 1435-1441, vol. 10 No. 8.
Korn et al, IL-17 and Th17 Cells, Annu. Rev. Immunol., 2009, 485-517, 27.
Lin, Shou-Yuan et al, Microwave-assisted one step high-throughput synthesis of benzimidazoles, Tetrahedron Letters, 2006, 2883-2886, vol. 47 No. 17.
Moseley et al, Interleukin-17 family and IL-17 receptors, Cytokine Growth Factor Rev, 2003, 155-174, 14.
Rouvier et al, CTLA-8, cloned from an activated T cell, bearing AU-rich messenger RNA instability sequences, and homologous to a herpesvirus saimiri gene, J. Immunol, 1993, 5445-5456, 150.
Wang, Fei et al, Molecular design, synthesis and anticoagulant activity evaluation of fluorinated dabigatran analogues, Bioorganic & Medicinal Chemistry, 2016, 2739-2753, vol. 24 No 12.
Wright et al, The human IL17/IL-17A Heterodimeric Cytokine Signals through the IL-17RA/IL-17RC Receptor Complex, J. Immunol, 2008, 2799-2805, 181.

* cited by examiner

FUSED IMIDAZOLE DERIVATIVES AS IL-17 MODULATORS

CROSS-REFERENCE TO RELATED APPLICATIONS

This application is a U.S. national phase of International Application No. PCT/EP2020/067758, filed Jun. 24, 2020, which claims priority from Great Britain patent application no. GB 1909191.7, filed Jun. 26, 2019, the disclosure of each of which is hereby incorporated by reference in its entirety.

The present invention relates to heterocyclic compounds, and to their use in therapy. More particularly, this invention is concerned with pharmacologically active substituted fused bicyclic imidazole derivatives, including benzimidazole derivatives and analogues thereof. These compounds act as modulators of IL-17 activity, and are accordingly of benefit as pharmaceutical agents for the treatment and/or prevention of pathological conditions, including adverse inflammatory and autoimmune disorders.

IL-17A (originally named CTLA-8 and also known as IL-17) is a pro-inflammatory cytokine and the founder member of the IL-17 family (Rouvier et al., *J. Immunol.,* 1993, 150, 5445-5456). Subsequently, five additional members of the family (IL-17B to IL-17F) have been identified, including the most closely related, IL-17F (ML-1), which shares approximately 55% amino acid sequence homology with IL-17A (Moseley et al., *Cytokine Growth Factor Rev.,* 2003, 14, 155-174). IL-17A and IL-17F are expressed by the recently defined autoimmune related subset of T helper cells, Th17, that also express IL-21 and IL-22 signature cytokines (Korn et al., *Ann. Rev. Immunol.,* 2009, 27, 485-517). IL-17A and IL-17F are expressed as homodimers, but may also be expressed as the IL-17A/F heterodimer (Wright et al., *J. Immunol.,* 2008, 181, 2799-2805). IL-17A and F signal through the receptors IL-17R, IL-17RC or an IL-17RA/RC receptor complex (Gaffen, *Cytokine,* 2008, 43, 402-407). Both IL-17A and IL-17F have been associated with a number of autoimmune diseases.

The compounds in accordance with the present invention, being potent modulators of human IL-17 activity, are therefore beneficial in the treatment and/or prevention of various human ailments, including inflammatory and autoimmune disorders.

Furthermore, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/116682 and WO 2014/066726 relate to separate classes of chemical compounds that are stated to modulate the activity of IL-17 and to be useful in the treatment of medical conditions, including inflammatory diseases.

WO 2018/229079 describes a class of spirocyclic oxoindoline derivatives, and analogues thereof, that are stated to act as modulators of IL-17 activity, and thus to be of benefit in the treatment of pathological conditions including adverse inflammatory and autoimmune disorders.

Co-pending international patent application PCT/EP2019/050594 (published on 18 Jul. 2019 as WO 2019/138017) describes a class of fused bicyclic imidazole derivatives, including benzimidazole derivatives and analogues thereof, that are stated to act as modulators of IL-17 activity, and thus to be of benefit in the treatment of pathological conditions including adverse inflammatory and autoimmune disorders.

None of the prior art available to date, however, discloses or suggests the precise structural class of substituted benzimidazole derivatives, and analogues thereof, as provided by the present invention.

The present invention provides a compound of formula (I) or an N-oxide thereof, or a pharmaceutically acceptable salt thereof:

(I)

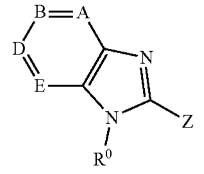

wherein

A represents C—$R^1$ or N;

B represents C—$R^2$ or N;

D represents C—$R^3$ or N;

E represents C—$R^4$ or N;

Z represents —$CH(R^5)N(H)CH_2R^6$, —$CH(R^5)N(H)S(O)_2R^6$, —$C(=CR^{5a}R^{5b})N(H)C(O)R^6$, —$CH(R^5)R^7$, —$CH(R^5)N(H)R^7$ or —$CH(R^5)C(O)N(H)R^7$;

$R^0$ represents hydrogen or $C_{1-6}$ alkyl;

$R^1$, $R^2$, $R^3$ and $R^4$ independently represent hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2R^e$, —$NHSO_2NR^bR^c$, —$N{=}S(O)R^bR^c$, —$COR^d$, —$CO_2R^d$, —$CONR^bR^c$, —$CON(OR^a)R^b$, —$SO_2NR^bR^c$ or —$S(O)(NR^c)R^a$; or $C_{1-6}$ alkyl, $C_{2-6}$ alkenyl, $C_{2-6}$ alkynyl, $C_{3-9}$ cycloalkyl, $C_{3-9}$ cycloalkyl($C_{1-6}$)alkyl, $C_{4-9}$ cycloalkenyl, aryl, aryl($C_{1-6}$)alkyl, $C_{3-7}$ heterocycloalkyl, $C_{3-7}$ heterocycloalkyl($C_{1-6}$)alkyl, $C_{3-7}$ hetero-cycloalkenyl, $C_{4-9}$ heterobicycloalkyl, heteroaryl or heteroaryl($C_{1-6}$)alkyl, any of which groups may be optionally substituted by one or more substituents;

$R^5$ represents hydrogen; or $R^5$ represents $C_{1-6}$ alkyl, $C_{3-9}$ cycloalkyl, $C_{3-9}$ cycloalkyl($C_{1-6}$)alkyl, $C_{4-9}$ cycloalkenyl, $C_{4-12}$ bicycloalkyl, $C_{5-9}$ spirocycloalkyl, $C_{5-9}$ spirocycloalkyl($C_{1-6}$)alkyl, $C_{8-11}$ tricycloalkyl, $C_{8-11}$ tricycloalkyl($C_{1-6}$)alkyl, $C_{7-13}$ dispirocycloalkyl, $C_{7-13}$ dispirocycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

$R^{5a}$ represents $C_{3-7}$ cycloalkyl, $C_{4-9}$ bicycloalkyl, aryl, $C_{3-7}$ heterocycloalkyl or heteroaryl, any of which groups may be optionally substituted by one or more substituents; and $R^{5b}$ represents hydrogen or $C_{1-6}$ alkyl; or $R^{5a}$ and $R^{5b}$, when taken together with the carbon atom to which they are both attached, represent $C_{3-7}$ cycloalkyl, $C_{4-9}$ bicycloalkyl or $C_{3-7}$ heterocycloalkyl, any of which groups may be optionally substituted by one or more substituents;

$R^6$ represents —$OR^{6a}$ or —$NR^{6b}R^{6c}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl ($C_{1-6}$)alkyl, any of which groups may be optionally substituted by one or more substituents;

$R^{6a}$ represents $C_{1-6}$ alkyl; or $R^{6a}$ represents $C_{3-9}$ cycloalkyl, which group may be optionally substituted by one or more substituents;

$R^{6b}$ represents hydrogen or $C_{1-6}$ alkyl;

$R^{6c}$ represents hydrogen or $C_{1-6}$ alkyl;

$R^7$ represents aryl, heteroaryl or spiro[($C_{3-7}$)heterocycloalkyl][heteroaryl], any of which groups may be optionally substituted by one or more substituents;

$R^a$ represents trifluoromethyl; or $R^a$ represents $C_{1-6}$ alkyl, $C_{3-9}$ cycloalkyl, $C_{3-9}$ cycloalkyl($C_{1-6}$)alkyl, aryl, aryl ($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-9}$ cycloalkyl, $C_{3-9}$ cycloalkyl ($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

$R^d$ represents hydrogen; or $R^d$ represents $C_{1-6}$ alkyl, $C_{3-9}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

The present invention also provides a compound of formula (I) as defined above, or a pharmaceutically acceptable salt thereof.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of IL-17 function is indicated.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of IL-17 function is indicated.

The present invention also provides a method for the treatment and/or prevention of disorders for which the administration of a modulator of IL-17 function is indicated which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one, two or three substituents. Suitably, such groups will be unsubstituted, or substituted by one or two substituents.

For use in medicine, the salts of the compounds of formula (I) will be pharmaceutically acceptable salts. Other salts may, however, be useful in the preparation of the compounds of formula (I) or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of formula (I) include acid addition salts which may, for example, be formed by mixing a solution of a compound of formula (I) with a solution of a pharmaceutically acceptable acid.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkenyl groups include vinyl and allyl.

Suitable $C_{2-6}$ alkynyl groups include ethynyl and propargyl.

The term "$C_{3-9}$ cycloalkyl" as used herein refers to monovalent groups of 3 to 9 carbon atoms derived from a saturated monocyclic hydrocarbon, and may comprise benzo-fused analogues thereof. Suitable $C_{3-9}$ cycloalkyl groups include cyclopropyl, cyclobutyl, benzocyclobutenyl, cyclopentyl, indanyl, cyclohexyl, cycloheptyl, cyclooctyl and cyclononanyl.

The term "$C_{4-9}$ cycloalkenyl" as used herein refers to monovalent groups of 4 to 9 carbon atoms derived from an unsaturated monocyclic hydrocarbon, and may comprise benzo-fused analogues thereof. Suitable $C_{4-9}$ cycloalkenyl groups include cyclobutenyl, cyclopentenyl, cyclohexenyl, cycloheptenyl and cyclooctenyl.

The term "$C_{4-12}$ bicycloalkyl" as used herein refers to monovalent groups of 4 to 12 carbon atoms derived from a saturated bicyclic hydrocarbon. Typical bicycloalkyl groups include bicyclo[1.1.1]pentanyl, bicyclo[3.1.0]hexanyl, bicyclo[4.1.0]heptanyl and bicyclo[2.2.2]octanyl.

The term "$C_{5-9}$ spirocycloalkyl" as used herein refers to saturated bicyclic ring systems containing 5 to 9 carbon atoms, in which the two rings are linked by a common atom. Suitable spirocycloalkyl groups include spiro[2.3]hexanyl, spiro[2.4]heptanyl, spiro[3.3]heptanyl, spiro[3.4]octanyl, spiro[3.5]nonanyl and spiro[4.4]nonanyl.

The term "$C_{8-11}$ tricycloalkyl" as used herein refers to monovalent groups of 8 to 11 carbon atoms derived from a saturated tricyclic hydrocarbon. Typical tricycloalkyl groups include adamantanyl.

The term "$C_{7-13}$ dispirocycloalkyl" as used herein refers to saturated tricyclic ring systems containing 7 to 13 carbon atoms, in which the three rings incorporate two spiro linkages. Suitable dispirocycloalkyl groups include dispiro[2.0.24.13]heptanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzofuranyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include 2,5-dihydropyrrolyl, thiazolinyl, imidazolinyl, dihydropyranyl, dihydrothiopyranyl, 1,2-dihydropyridinyl, 1,2,3,4-tetrahydropyridinyl, 1,2,3,6-tetrahydropyridinyl, 2,3-dihydro-1,4-oxazinyl and 6,7-dihydro-5H-1,4-oxazepinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 6-oxabicyclo[3.1.0]hexanyl, 3-azabicyclo[3.1.0]hexanyl, 2-oxa-5-azabicyclo[2.2.1]heptanyl, 6-azabicyclo[3.2.0]heptanyl, 6-oxabicyclo[3.1.1]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 8-oxabicyclo[3.2.1]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,7-dioxa-9-azabicyclo-[3.3.1]nonanyl and 3,9-diazabicyclo[4.2.1]nonanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, pyrazolo[1,5-a]pyrazinyl, indazolyl, 4,5,6,7-tetrahydroindazolyl, oxazolyl, benzoxazolyl, isoxazolyl, isoxazolo[4,5-b]pyridinyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]-pyridinyl, imidazo[1,2-b]pyridazinyl, purinyl, imidazo[1,2-a]pyrimidinyl, imidazo[1,2-c]-pyrimidinyl, imidazo[1,2-a]pyrazinyl, oxadiazolyl, thiadiazolyl, triazolyl, [1,2,4]triazolo-[1,5-a]pyrimidinyl, 6,8-dihydro-5H-[1,2,4]triazolo[4,3-a]pyrazinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C{=}O$)↔enol ($CH{=}CHOH$) tautomers or amide ($NHC{=}O$)↔hydroxyimine ($N{=}COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^{1}H$, $^{2}H$ (deuterium) or $^{3}H$ (tritium) atom, preferably $^{1}H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one embodiment, A represents C—$R^1$. In another embodiment, A represents N.

In one embodiment, B represents C—$R^2$. In another embodiment, B represents N.

In one embodiment, D represents C—$R^3$. In another embodiment, D represents N.

In one embodiment, E represents C—$R^4$. In another embodiment, E represents N.

In a particular embodiment, A represents C—$R^1$, B represents C—$R^2$, D represents C—$R^3$ and E represents C—$R^4$.

In another embodiment, A represents C—$R^1$, B represents C—$R^2$, D represents N and E represents C—$R^4$.

In another embodiment, A represents C—$R^1$, B represents N, D represents C—$R^3$ and E represents C—$R^4$.

In another embodiment, A represents N, B represents C—$R^2$, D represents C—$R^3$ and E represents C—$R^4$.

In another embodiment, A represents N, B represents C—$R^2$, D represents C—$R^3$ and E represents N.

In another embodiment, A represents N, B represents C—$R^2$, D represents N and E represents C—$R^4$.

Suitably, the present invention provides a compound of formula (I-1), (I-2), (I-3), (I-4), (I-5) or (I-6) or an N-oxide thereof, or a pharmaceutically acceptable salt thereof:

(I-1)

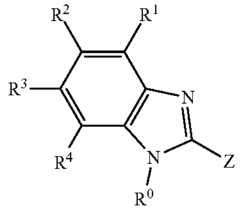

(I-2)

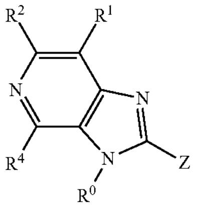

(I-3)

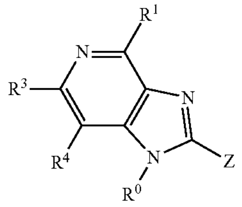

(I-4)

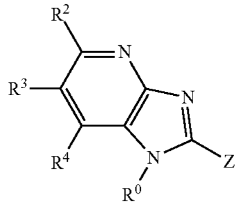

(I-5)

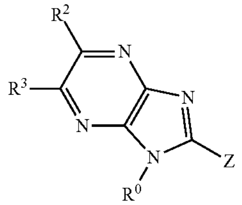

(I-6)

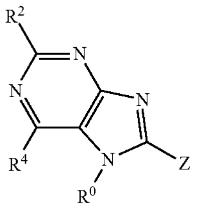

wherein Z, $R^0$, $R^1$, $R^2$, $R^3$ and $R^4$ are as defined above.

Favourably, the present invention provides a compound of formula (I-1) as defined above or an N-oxide thereof, or a pharmaceutically acceptable salt thereof.

Suitably, $R^0$ represents hydrogen or methyl.

In a particular embodiment, $R^0$ represents hydrogen. In another embodiment, $R^0$ represents $C_{1-6}$ alkyl, especially methyl.

Generally, $R^1$, $R^2$, $R^3$ and $R^4$ independently represent hydrogen, halogen, cyano, —$OR^a$, —$SOR^a$, —$NR^bR^c$, —$NR^cCOR^d$ or —N═S(O)$R^bR^c$; or $C_{1-6}$ alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, heteroaryl or heteroaryl($C_{1-6}$)alkyl, any of which groups may be optionally substituted by one or more substituents.

Appositely, $R^1$, $R^2$, $R^3$ and $R^4$ independently represent hydrogen or halogen; or $C_{1-6}$ alkyl or $C_{3-7}$ heterocycloalkyl, either of which groups may be optionally substituted by one or more substituents.

Suitably, $R^1$, $R^2$, $R^3$ and $R^4$ independently represent hydrogen or halogen; or $C_{3-7}$ heterocycloalkyl, which group may be optionally substituted by one or more substituents.

Aptly, $R^2$, $R^3$ and $R^4$ independently represent hydrogen, fluoro, chloro, cyano, —$OR^a$, —$SOR^a$, —$NR^bR^c$, —$NR^c$-$COR^d$ or —N═S(O)$R^bR^c$; or methyl, ethyl, propyl, phenyl, benzyl, tetrahydrofuranyl, pyrrolidinyl, tetrahydropyranyl, piperidinyl, piperazinyl, morpholinyl, oxazepinyl, pyrrolidinylmethyl, piperidinylmethyl, piperazinylmethyl, morpholinylmethyl, 2,5-dihydropyrrolyl, 3,6-dihydro-2H-pyranyl, 1,2,3,4-tetrahydropyridinyl, 2,3-dihydro-1,4-oxazinyl, 6,7-dihydro-5H-1,4-oxazepinyl, furyl, pyrazolyl, 6,8-dihydro-5H-[1,2,4]triazolo[4,3-a]pyrazinyl, pyridinyl, pyrimidinyl, pyrazinyl, pyridinylmethyl or pyridinylethyl, any of which groups may be optionally substituted by one or more substituents.

More aptly, $R^1$, $R^2$, $R^3$ and $R^4$ independently represent hydrogen or fluoro; or ethyl, tetrahydrofuranyl, pyrrolidinyl or tetrahydropyranyl, any of which groups may be optionally substituted by one or more substituents.

Typically, $R^2$, $R^3$ and $R^4$ independently represent hydrogen or fluoro; or tetrahydrofuranyl or pyrrolidinyl, either of which groups may be optionally substituted by one or more substituents.

Illustrative examples of optional substituents which may be present on $R^1$, $R^2$, $R^3$ or $R^4$ include one, two or three substituents independently selected from halogen, cyano, nitro, $C_{1-6}$ alkyl, trifluoromethyl, difluoroethyl, phenyl, fluorophenyl, benzyl, oxetanyl, pyrrolidinyl, tetrahydropyranyl, morpholinyl, piperazinyl, oxadiazolyl, ($C_{1-6}$)alkyloxadiazolyl, hydroxy, hydroxy($C_{1-6}$)alkyl, oxo, $C_{1-6}$ alkoxy, difluoromethoxy, trifluoromethoxy, pentafluorothio, $C_{1-6}$ alkylthio, $C_{1-6}$ alkylsulfinyl, ($C_{1-6}$)alkyl(imino)sulfinyl, $C_{1-6}$ alkyl sulfonyl, amino, amino($C_{1-6}$)alkyl, $C_{1-6}$ alkylamino, di($C_{1-6}$)alkylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, hydroxy($C_{1-6}$)alkylcarbonyl, carboxy, $C_{2-6}$ alkoxycarbonyl, aminocarbonyl, $C_{1-6}$ alkylaminocarbonyl, chloro($C_{1-6}$)alkylaminocarbonyl, di($C_{1-6}$)alkylaminocarbonyl, azetidinylcarbonyl, hydroxyazetidinylcarbonyl, difluoroazetidinylcarbonyl, (hydroxy)(trifluoromethyl)azetidinylcarbonyl, (hydroxy)-(methyl)azetidinylcarbonyl, morpholinylcarbonyl, ($C_{1-6}$)alkylpyrazolylcarbonyl, aminosulfonyl, $C_{1-6}$ alkylaminosulfonyl, di($C_{1-6}$)alkylaminosulfonyl, ($C_{1-6}$)alkylsulfoximinyl, trifluoromethylsulfoximinyl, [($C_{1-6}$)alkyl][N—($C_{1-6}$)alkyl]sulfoximinyl, [($C_{1-6}$)alkyl][N-carboxy($C_{1-6}$)alkyl]sulfoximinyl, [N—($C_{2-6}$)alkoxycarbonyl($C_{1-6}$)alkyl][($C_{1-6}$)alkyl]-sulfoximinyl, ($C_{3-7}$)cycloalkylsulfoximinyl, N-[di($C_{1-6}$)alkylsulfoxo]iminyl and di($C_{1-6}$)alkylsulfoximinyl.

Typical examples of optional substituents which may be present on $R^1$, $R^2$, $R^3$ or $R^4$ include one, two or three substituents independently selected from benzyl and difluoroazetidinylcarbonyl.

Illustrative examples of particular substituents which may be present on $R^1$, $R^2$, $R^3$ or $R^4$ include one, two or three substituents independently selected from fluoro, chloro, bromo, cyano, nitro, methyl, ethyl, isopropyl, tert-butyl, trifluoromethyl, difluoroethyl, phenyl, fluorophenyl, benzyl, oxetanyl, pyrrolidinyl, tetrahydropyranyl, morpholinyl, piperazinyl, oxadiazolyl, methyloxadiazolyl, hydroxy, hydroxymethyl, hydroxyisopropyl, oxo, methoxy, tert-butoxy, difluoromethoxy, trifluoromethoxy, pentafluorothio, methylthio, methylsulfinyl, (imino)(methyl)sulfinyl, methyl sulfonyl, amino, aminomethyl, aminoethyl, methylamino, tert-butylamino, dimethylamino, acetylamino, acetylaminoethyl, methoxycarbonylamino, methylsulfonylamino, formyl, acetyl, hydroxyacetyl, carboxy, methoxycarbonyl, ethoxycarbonyl, tert-butoxycarbonyl, aminocarbonyl, methylaminocarbonyl, ethylaminocarbonyl, chloropropylaminocarbonyl, dimethylaminocarbonyl, azetidinylcarbonyl, hydroxyazetidinylcarbonyl, difluoroazetidinylcarbonyl, (hydroxy)(trifluoromethyl)azetidinylcarbonyl, (hydroxy)(methyl)azetidinylcarbonyl, morpholinylcarbonyl, ethylpyrazolylcarbonyl, aminosulfonyl, methylaminosulfonyl, dimethylaminosulfonyl, methylsulfoximinyl, ethylsulfoximinyl, trifluoromethylsulfoximinyl, (methyl)(N-methyl) sulfoximinyl, (N-carboxymethyl)(methyl)sulfoximinyl, (N-tert-butoxycarbonylmethyl)(methyl)sulfoximinyl, cyclopropylsulfoximinyl, N-(dimethylsulfoxo)iminyl and dimethylsulfoximinyl.

Typical examples of particular substituents on $R^1$, $R^2$, $R^3$ or $R^4$ include one, two or three substituents independently selected from benzyl and difluoroazetidinylcarbonyl.

Particular values of $R^1$, $R^2$, $R^3$ or $R^4$ include hydrogen, fluoro, chloro, cyano, —$OR^a$, —$SOR^a$, —$NR^bR^c$, —$NR^cCOR^d$, —N═S(O)$R^bR^c$, tert-butoxycarbonylmethyl, dimethylaminocarbonylmethyl, acetylaminoethyl, carboxyethyl, tert-butoxycarbonylethyl, methylaminocarbonylethyl, dimethylaminocarbonylethyl, acetylaminopropyl, methylsulfonylphenyl, methyl sulfonylaminophenyl, tert-butoxycarbonylphenyl, dimethylaminocarbonylphenyl, ethoxycarbonylbenzyl, carboxytetrahydrofuranyl, methoxycarbonyltetrahydrofuranyl, dimethylaminocarbonyltetrahydrofuranyl, hydroxyazetidinylcarbonyltetrahydrofuranyl, difluoroazetidinylcarbonyltetrahydrofuranyl, (hydroxy)(trifluoromethyl)-azetidinylcarbonyltetrahydrofuranyl, morpholinylcarbonyltetrahydrofuranyl, methoxycarbonylpyrrolidinyl, tert-butoxycarbonylpyrrolidinyl, dimethylaminocarbonylpyrrolidinyl, difluoroazetidinylcarbonylpyrrolidinyl, (ethoxycarbonyl)(methylsulfonyl)-pyrrolidinyl, (acetyl)(ethoxycarbonyl)pyrrolidinyl, (benzyl)(difluoroazetidinylcarbonyl)-pyrrolidinyl, (tert-butoxycarbonyl)(difluoroazetidinylcarbonyl)pyrrolidinyl, tetrahydropyranyl, ethoxycarbonyltetrahydropyranyl, dimethylaminocarbonyltetrahydropyranyl, piperidinyl, methylpiperidinyl, acetylpiperidinyl, hydroxyacetylpiperidinyl, methoxycarbonylpiperidinyl, tert-butoxycarbonylpiperidinyl, dimethylaminocarbonylpiperidinyl, ethylpyrazolylcarbonylpiperidinyl, methylpiperazinyl, morpholinyl, methyloxadiazolylmorpholinyl, methyl sulfonylmorpholinyl, acetylmorpholinyl, hydroxyacetylmorpholinyl, methoxycarbonylmorpholinyl, ethoxycarbonylmorpholinyl, tert-butoxycarbonylmorpholinyl, ethylaminocarbonylmorpholinyl, difluoroazetidinylcarbonylmorpholinyl, oxazepinyl, tert-butoxycarbonyloxazepinyl, oxopyrrolidinylmethyl, carboxypyrrolidinylmethyl, methoxycarbonylpyrrolidinylmethyl, dimethylaminocarbonylpyrrolidinylmethyl, methyl sulfonylpiperidinylmethyl, piperazinylmethyl, methylpiperazinylmethyl, oxetanylpiperazinylmethyl, methyl sulfonylpiperazinylmethyl, acetylpiperazinylmethyl, tert-butoxycarbonylpiperazinylmethyl, (acetyl)(tert-butoxycarbonyl) piperazinylmethyl, morpholinylmethyl, (tert-butoxycarbonyl)(difluoroazetidinylcarbonyl)-2,5-dihydropyrrolyl, 3,6-dihydro-2H-pyranyl, ethoxycarbonyl-3,6-dihydro-2H-pyranyl, dimethylaminocarbonyl-3,6-dihydro-2H-pyranyl, tert-butoxycarbonyl-1,2,3,4-tetrahydropyridinyl, tert-butoxycarbonyl-2,3-dihydro-1,4-oxazinyl, tert-butoxycarbonyl-6,7-dihydro-5H-1,4-oxazepinyl, difluoroazetidinylcarbonylfuryl, difluoroazetidinylcarbonylpyrazolyl, acetyl-6,8-dihydro-5H-[1,2,4]triazolo[4,3-a]-pyrazinyl, (imino)(methyl)sulfinylpyridinyl, ethoxycarbonylpyridinyl, chloropropylaminocarbonylpyridinyl, dimethylaminocarbonylpyridinyl, azetidinylcarbonylpyridinyl, difluoroazetidinylcarbonylpyridinyl, (hydroxy)(methyl)azetidinylcarbonylpyridinyl, (dimethylaminocarbonyl)(fluoro)pyridinyl, dimethylaminocarbonylpyrimidinyl, (dimethylaminocarbonyl)(methyl)pyrimidinyl, dimethylaminocarbonylpyrazinyl, pyridinylmethyl, cyanopyridinylmethyl, oxadiazolylpyridinylmethyl, ethoxycarbonylpyridinylmethyl, aminocarbonylpyridinylmethyl, pyridinylethyl and hydroxypyridinylethyl. Additional values include difluoroazetidinylcarbonylethyl and difluoroazetidinylcarbonyltetrahydropyranyl.

Selected values of $R^1$, $R^2$, $R^3$ or $R^4$ include hydrogen, fluoro, difluoroazetidinylcarbonylethyl, difluoroazetidinylcarbonyltetrahydrofuranyl, (benzyl)(difluoroazetidinylcarbonyl)pyrrolidinyl and difluoroazetidinylcarbonyltetrahydropyranyl.

Suitable values of $R^1$, $R^2$, $R^3$ or $R^4$ include hydrogen, fluoro, difluoroazetidinylcarbonyltetrahydrofuranyl and (benzyl)(difluoroazetidinylcarbonyl)pyrrolidinyl.

Suitably, $R^1$ represents hydrogen or halogen.

In a first embodiment, $R^1$ represents hydrogen. In a second embodiment, $R^1$ represents halogen. In one aspect of that embodiment, $R^1$ represents fluoro. In another aspect of that embodiment, $R^1$ represents chloro.

Typical values of $R^1$ include hydrogen and fluoro, especially fluoro.

Generally, $R^2$ represents hydrogen, cyano, —$OR^a$, —$SOR^a$, —$NR^bR^c$, —$NR^cCOR^d$ or —N═S(O)$R^bR^c$; or $R^2$ represents $C_{1-6}$ alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, heteroaryl or heteroaryl($C_{1-6}$)alkyl, any of which groups may be optionally substituted by one or more substituents.

Appositely, $R^2$ represents $C_{1-6}$ alkyl or $C_{3-7}$ heterocycloalkyl, either of which groups may be optionally substituted by one or more substituents.

Suitably, $R^2$ represents $C_{3-7}$ heterocycloalkyl, which group may be optionally substituted by one or more substituents.

Aptly, $R^2$ represents hydrogen, cyano, —$OR^a$, —$SOR^a$, —$NR^bR^c$, —$NR^cCOR^d$ or —N═S(O)$R^bR^c$; or $R^2$ represents methyl, ethyl, propyl, phenyl, benzyl, tetrahydrofuranyl, pyrrolidinyl, tetrahydropyranyl, piperidinyl, piperazinyl, morpholinyl, oxazepinyl, pyrrolidinylmethyl, piperidinylmethyl, piperazinylmethyl, morpholinylmethyl, 2,5-dihydropyrrolyl, 3,6-dihydro-2H-pyranyl, 1,2,3,4-tetrahydropyridinyl, 2,3-dihydro-1,4-oxazinyl, 6,7-dihydro-5H-1,4-oxazepinyl, furyl, pyrazolyl, 6,8-dihydro-5H-[1,2,4]-triazolo[4,3-a]pyrazinyl, pyridinyl, pyrimidinyl, pyrazinyl, pyridinylmethyl or pyridinylethyl, any of which groups may be optionally substituted by one or more substituents.

More aptly, $R^2$ represents ethyl, tetrahydrofuranyl, pyrrolidinyl or tetrahydropyranyl, any of which groups may be optionally substituted by one or more substituents.

Typically, $R^2$ represents tetrahydrofuranyl or pyrrolidinyl, either of which groups may be optionally substituted by one or more substituents.

Illustrative examples of optional substituents on $R^2$ include one, two or three substituents independently selected from halogen, cyano, nitro, $C_{1-6}$ alkyl, trifluoromethyl, phenyl, fluorophenyl, benzyl, oxetanyl, pyrrolidinyl, tetrahydropyranyl, morpholinyl, piperazinyl, oxadiazolyl, $(C_{1-6})$alkyloxadiazolyl, hydroxy, hydroxy-$(C_{1-6})$alkyl, oxo, $C_{1-6}$ alkoxy, difluoromethoxy, trifluoromethoxy, $C_{1-6}$ alkylthio, $C_{1-6}$ alkylsulfinyl, $(C_{1-6})$alkyl(imino)sulfinyl, $C_{1-6}$ alkylsulfonyl, amino, amino$(C_{1-6})$alkyl, $C_{1-6}$ alkylamino, di$(C_{1-6})$alkylamino, $C_{2-6}$ alkylcarbonylamino, $C_{2-6}$ alkylcarbonylamino-$(C_{1-6})$alkyl, $C_{2-6}$ alkoxycarbonylamino, $C_{1-6}$ alkylsulfonylamino, formyl, $C_{2-6}$ alkylcarbonyl, hydroxy $(C_{1-6})$alkylcarbonyl, carboxy, $C_{2-6}$ alkoxycarbonyl, aminocarbonyl, $C_{1-6}$ alkylaminocarbonyl, chloro$(C_{1-6})$alkylaminocarbonyl, di$(C_{1-6})$alkylaminocarbonyl, azetidinylcarbonyl, hydroxyazetidinylcarbonyl, difluoroazetidinylcarbonyl, (hydroxy)-(trifluoromethyl)azetidinylcarbonyl, (hydroxy)(methyl)azetidinylcarbonyl, morpholinylcarbonyl, $(C_{1-6})$alkylpyrazolylcarbonyl, aminosulfonyl, $C_{1-6}$ alkylaminosulfonyl, di-$(C_{1-6})$alkylaminosulfonyl and di$(C_{1-6})$alkylsulfoximinyl.

Typical examples of optional substituents on $R^2$ include one, two or three substituents independently selected from benzyl and difluoroazetidinylcarbonyl.

Illustrative examples of particular substituents on $R^2$ include one, two or three substituents independently selected from fluoro, chloro, bromo, cyano, nitro, methyl, ethyl, isopropyl, tert-butyl, trifluoromethyl, phenyl, fluorophenyl, benzyl, oxetanyl, pyrrolidinyl, tetrahydropyranyl, morpholinyl, piperazinyl, oxadiazolyl, methyloxadiazolyl, hydroxy, hydroxymethyl, oxo, methoxy, tert-butoxy, difluoromethoxy, trifluoromethoxy, methylthio, methylsulfinyl, (imino)(methyl)sulfinyl, methyl sulfonyl, amino, aminomethyl, aminoethyl, methylamino, tert-butylamino, dimethylamino, acetylamino, acetylaminoethyl, methoxycarbonylamino, methylsulfonylamino, formyl, acetyl, hydroxyacetyl, carboxy, methoxycarbonyl, ethoxycarbonyl, tert-butoxycarbonyl, aminocarbonyl, methylaminocarbonyl, ethylaminocarbonyl, chloropropylaminocarbonyl, dimethylaminocarbonyl, azetidinylcarbonyl, hydroxyazetidinylcarbonyl, difluoroazetidinylcarbonyl, (hydroxy)(trifluoromethyl)azetidinylcarbonyl, (hydroxy)(methyl)-azetidinylcarbonyl, morpholinylcarbonyl, ethylpyrazolylcarbonyl, aminosulfonyl, methylaminosulfonyl, dimethylaminosulfonyl and dimethylsulfoximinyl.

Typical examples of particular substituents on $R^2$ include one, two or three substituents independently selected from benzyl and difluoroazetidinylcarbonyl.

Illustrative values of $R^2$ include hydrogen, cyano, —$OR^a$, —$SOR^a$, —$NR^bR^c$, —$NR^cCOR^d$, —N═S(O)$R^bR^c$, tert-butoxycarbonylmethyl, dimethylaminocarbonylmethyl, acetylaminoethyl, carboxyethyl, tert-butoxycarbonylethyl, methylaminocarbonylethyl, dimethylaminocarbonylethyl, acetylaminopropyl, methyl sulfonylphenyl, methylsulfonylaminophenyl, tert-butoxycarbonylphenyl, dimethylaminocarbonylphenyl, ethoxycarbonylbenzyl, carboxytetrahydrofuranyl, methoxycarbonyltetrahydrofuranyl, dimethylaminocarbonyltetrahydrofuranyl, hydroxyazetidinylcarbonyltetrahydrofuranyl, difluoroazetidinylcarbonyltetrahydrofuranyl, (hydroxy)(trifluoromethyl)azetidinylcarbonyltetrahydrofuranyl, morpholinylcarbonyltetrahydrofuranyl, methoxycarbonylpyrrolidinyl, tert-butoxycarbonylpyrrolidinyl, dimethylaminocarbonylpyrrolidinyl, difluoroazetidinylcarbonylpyrrolidinyl, (ethoxycarbonyl)(methylsulfonyl) pyrrolidinyl, (acetyl)-(ethoxycarbonyl)pyrrolidinyl, (benzyl)(difluoroazetidinylcarbonyl)pyrrolidinyl, (tert-butoxycarbonyl)(difluoroazetidinylcarbonyl)pyrrolidinyl, tetrahydropyranyl, ethoxycarbonyltetrahydropyranyl, dimethylaminocarbonyltetrahydropyranyl, piperidinyl, methylpiperidinyl, acetylpiperidinyl, hydroxyacetylpiperidinyl, methoxycarbonylpiperidinyl, tert-butoxycarbonylpiperidinyl, dimethylaminocarbonylpiperidinyl, ethylpyrazolylcarbonylpiperidinyl, methylpiperazinyl, morpholinyl, methyloxadiazolylmorpholinyl, methyl sulfonylmorpholinyl, acetylmorpholinyl, hydroxyacetylmorpholinyl, methoxycarbonylmorpholinyl, ethoxycarbonylmorpholinyl, tert-butoxycarbonylmorpholinyl, ethylaminocarbonylmorpholinyl, difluoroazetidinylcarbonylmorpholinyl, oxazepinyl, tert-butoxycarbonyloxazepinyl, oxopyrrolidinylmethyl, carboxypyrrolidinylmethyl, methoxycarbonylpyrrolidinylmethyl, dimethylaminocarbonylpyrrolidinylmethyl, methylsulfonylpiperidinylmethyl, piperazinylmethyl, methylpiperazinylmethyl, oxetanylpiperazinylmethyl, methyl sulfonylpiperazinylmethyl, acetylpiperazinylmethyl, tert-butoxycarbonylpiperazinylmethyl, (acetyl)(tert-butoxycarbonyl)piperazinylmethyl, morpholinylmethyl, (tert-butoxycarbonyl)(difluoroazetidinylcarbonyl)-2,5-dihydropyrrolyl, 3,6-dihydro-2H-pyranyl, ethoxycarbonyl-3,6-dihydro-2H-pyranyl, dimethylaminocarbonyl-3,6-dihydro-2H-pyranyl, tert-butoxycarbonyl-1,2,3,4-tetrahydropyridinyl, tert-butoxycarbonyl-2,3-dihydro-1,4-oxazinyl, tert-butoxycarbonyl-6,7-dihydro-5H-1,4-oxazepinyl, difluoroazetidinylcarbonylfuryl, difluoroazetidinylcarbonylpyrazolyl, acetyl-6,8-dihydro-5H-[1,2,4]triazolo[4,3-a]pyrazinyl, (imino)(methyl)sulfinylpyridinyl, ethoxycarbonylpyridinyl, chloropropylaminocarbonylpyridinyl, dimethylaminocarbonylpyridinyl, azetidinylcarbonylpyridinyl, difluoroazetidinylcarbonylpyridinyl, (hydroxy)-(methyl)azetidinylcarbonylpyridinyl, (dimethylaminocarbonyl)(fluoro)pyridinyl, dimethylaminocarbonylpyrimidinyl, (dimethylaminocarbonyl)(methyl)pyrimidinyl, dimethylaminocarbonylpyrazinyl, pyridinylmethyl, cyanopyridinylmethyl, oxadiazolylpyridinylmethyl, ethoxycarbonylpyridinylmethyl, aminocarbonylpyridinylmethyl, pyridinylethyl and hydroxypyridinylethyl. Additional values include difluoroazetidinylcarbonylethyl and difluoroazetidinylcarbonyltetrahydropyranyl.

Selected values of $R^2$ include difluoroazetidinylcarbonylethyl [especially 1-(3,3-difluoroazetidin-1-ylcarbonyl) ethyl], difluoroazetidinylcarbonyltetrahydrofuranyl, (benzyl)(difluoroazetidinylcarbonyl)pyrrolidinyl and difluoroazetidinylcarbonyltetrahydropyranyl [especially 4-(3,3-difluoroazetidin-1-ylcarbonyl)tetrahydropyran-4-yl].

Suitable values of $R^2$ include difluoroazetidinylcarbonyltetrahydrofuranyl and (benzyl)(difluoroazetidinylcarbonyl)pyrrolidinyl.

Typically, $R^3$ represents hydrogen, halogen or —$NR^bR^c$; or $R^3$ represents $C_{1-6}$ alkyl, aryl, $C_{3-7}$ heterocycloalkyl, $C_{3-7}$ heterocycloalkyl$(C_{1-6})$alkyl or heteroaryl, any of which groups may be optionally substituted by one or more substituents.

Suitably, $R^3$ represents hydrogen, fluoro or —$NR^bR^c$; or $R^3$ represents ethyl, phenyl, morpholinyl, piperidinylmethyl, piperazinylmethyl, morpholinylmethyl or pyridinyl, any of which groups may be optionally substituted by one or more substituents.

Typical examples of optional substituents on $R^3$ include one, two or three substituents independently selected from halogen, cyano, nitro, $C_{1-6}$ alkyl, trifluoromethyl, hydroxy, hydroxy$(C_{1-6})$alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkyl sulfonyl, amino, amino$(C_{1-6})$alkyl, $C_{1-6}$ alkylamino, di$(C_{1-6})$alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di$(C_{1-6})$alkylaminocarbonyl, difluoroazetidinylcarbonyl, aminosulfonyl, $C_{1-6}$ alkylaminosulfonyl and di($C_{1-6}$)alkylaminosulfonyl.

Typical examples of specific substituents on $R^3$ include one, two or three substituents independently selected from fluoro, chloro, bromo, cyano, nitro, methyl, ethyl, isopropyl, tert-butyl, trifluoromethylhydroxy, hydroxymethyl, oxo, methoxy, tert-butoxy, difluoromethoxy, trifluoromethoxy, methylthio, methylsulfinyl, methyl sulfonyl, amino, aminomethyl, aminoethyl, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, difluoroazetidinylcarbonyl, aminosulfonyl, methylaminosulfonyl and dimethylaminosulfonyl.

Illustrative values of $R^3$ include hydrogen, fluoro, —$NR^bR^c$, tert-butoxycarbonylethyl, dimethylaminocarbonylphenyl, morpholinyl, methyl sulfonylpiperidinylmethyl, methylsulfonylpiperazinylmethyl, acetylpiperazinylmethyl, morpholinylmethyl and difluoroazetidinylcarbonylpyridinyl.

In a particular embodiment, $R^3$ represents hydrogen.

Typically, $R^4$ represents hydrogen, halogen or —$OR^a$.

In a first embodiment, $R^4$ represents hydrogen. In a second embodiment, $R^4$ represents halogen. In one aspect of that embodiment, $R^4$ represents fluoro. In another aspect of that embodiment, $R^4$ represents chloro. In a third embodiment, $R^4$ represents —$OR^a$.

Typical values of $R^4$ include hydrogen, fluoro and —$OR^a$, especially hydrogen.

In a first embodiment, Z represents —$CH(R^5)N(H)CH_2R^6$.

In a second embodiment, Z represents —$CH(R^5)N(H)S(O)_2R^6$.

In a third embodiment, Z represents —$C(=CR^{5a}R^{5b})N(H)C(O)R^6$.

In a fourth embodiment, Z represents —$CH(R^5)R^7$.

In a fifth embodiment, Z represents —$CH(R^5)N(H)R^7$.

In a sixth embodiment, Z represents —$CH(R^5)C(O)N(H)R^7$.

A first sub-class of compounds according to the invention is represented by the compounds of formula (IA), and pharmaceutically acceptable salts thereof:

(IA)

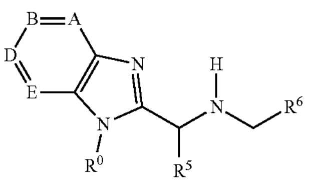

wherein

A, B, D, E, $R^0$, $R^5$ and $R^6$ are as defined above.

A second sub-class of compounds according to the invention is represented by the compounds of formula (IB), and pharmaceutically acceptable salts thereof:

(IB)

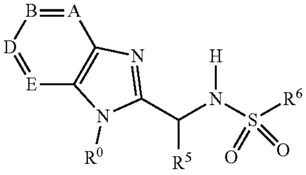

wherein

A, B, D, E, $R^0$, $R^5$ and $R^6$ are as defined above.

A third sub-class of compounds according to the invention is represented by the compounds of formula (IC), and pharmaceutically acceptable salts thereof:

(IC)

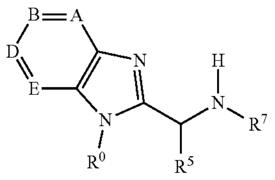

wherein

A, B, D, E, $R^0$, $R^5$ and $R^7$ are as defined above.

A fourth sub-class of compounds according to the invention is represented by the compounds of formula (ID), and pharmaceutically acceptable salts thereof:

(ID)

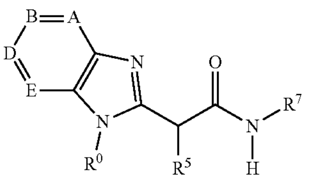

wherein

A, B, D, E, $R^0$, $R^5$ and $R^7$ are as defined above.

A fifth sub-class of compounds according to the invention is represented by the compounds of formula (IE), and pharmaceutically acceptable salts thereof:

(IE)

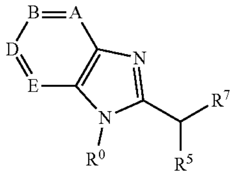

wherein

A, B, D, E, $R^0$, $R^5$ and $R^7$ are as defined above.

A sixth sub-class of compounds according to the invention is represented by the compounds of formula (IF), and pharmaceutically acceptable salts thereof:

(IF)

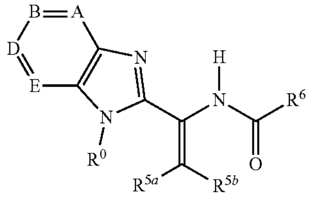

wherein

A, B, D, E, $R^0$, $R^{5a}$, $R^{5b}$ and $R^6$ are as defined above.

Generally, Z represents —$CH(R^5)N(H)S(O)_2R^6$ or —$CH(R^5)N(H)R^7$.

Thus, particular sub-classes of compounds according to the invention are represented by the compounds of formula (IB) and (IC) as defined above, and pharmaceutically acceptable salts thereof.

Typically, $R^5$ represents $C_{1-6}$ alkyl, $C_{3-9}$ cycloalkyl, $C_{3-9}$ cycloalkyl($C_{1-6}$)alkyl, $C_{4-9}$ cycloalkenyl, $C_{4-12}$ bicycloalkyl, $C_{5-9}$ spirocycloalkyl, $C_{5-9}$ spirocycloalkyl($C_{1-5}$)alkyl, $C_{8-11}$ tricycloalkyl, $C_{8-11}$ tricycloalkyl($C_{1-6}$)alkyl, $C_{7-13}$ dispirocycloalkyl, aryl, aryl-($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Suitably, $R^5$ represents $C_{3-9}$ cycloalkyl, $C_{4-12}$ bicycloalkyl, $C_{5-9}$ spirocycloalkyl or $C_{7-13}$ dispirocycloalkyl, any of which groups may be optionally substituted by one or more substituents.

Appositely, $R^5$ represents $C_{3-9}$ cycloalkyl, which group may be optionally substituted by one or more substituents.

In a first embodiment, $R^5$ represents hydrogen. In a second embodiment, $R^5$ represents optionally substituted $C_{1-6}$ alkyl. In a third embodiment, $R^5$ represents optionally substituted $C_{3-9}$ cycloalkyl. In a fourth embodiment, $R^5$ represents optionally substituted $C_{3-9}$ cycloalkyl($C_{1-6}$)alkyl. In a fifth embodiment, $R^5$ represents optionally substituted $C_{4-9}$ cycloalkenyl. In a sixth embodiment, $R^5$ represents optionally substituted $C_{4-9}$ bicycloalkyl. In a seventh embodiment, $R^5$ represents optionally substituted $C_{5-9}$ spirocycloalkyl. In an eighth embodiment, $R^5$ represents optionally substituted $C_{5-9}$ spirocycloalkyl($C_{1-6}$)alkyl. In a ninth embodiment, $R^5$ represents optionally substituted $C_{8-11}$ tricycloalkyl. In a tenth embodiment, $R^5$ represents optionally substituted $C_{8-11}$ tricycloalkyl($C_{1-6}$)alkyl. In an eleventh embodiment, $R^5$ represents optionally substituted aryl. In a twelfth embodiment, $R^5$ represents optionally substituted aryl($C_{1-6}$)alkyl. In a thirteenth embodiment, $R^5$ represents optionally substituted $C_{3-7}$ heterocycloalkyl. In a fourteenth embodiment, $R^5$ represents optionally substituted $C_{3-7}$ heterocycloalkyl($C_{1-6}$)-alkyl. In a fifteenth embodiment, $R^5$ represents optionally substituted heteroaryl. In a sixteenth embodiment, $R^5$ represents optionally substituted heteroaryl($C_{1-6}$)alkyl. In a seventeenth embodiment, $R^5$ represents optionally substituted $C_{7-13}$ dispirocycloalkyl. In an eighteenth embodiment, $R^5$ represents optionally substituted $C_{7-13}$ dispirocycloalkyl-($C_{1-6}$)alkyl.

In a particular embodiment, $R^5$ is other than hydrogen.

Typical values of $R^5$ include methyl, isopropyl, 1-methylpropyl, 2-methylpropyl, cyclopropyl, cyclopentyl, indanyl, cyclohexyl, cycloheptyl, cyclooctyl, cyclohexylmethyl, cyclooctenyl, bicyclo[4.1.0]heptanyl, spiro[3.3]heptanyl, spiro[2.5]octanyl, spiro[3.3]-heptanylmethyl, adamantanyl, adamantanylmethyl, dispiro[2.0.24.13]heptanyl, phenyl, benzyl, phenylethyl, naphthylmethyl, thienyl, indolyl, pyridinyl, thienylmethyl, indolylmethyl and pyridinylmethyl, any of which groups may be optionally substituted by one or more substituents.

Illustrative values of $R^5$ include cyclopentyl, cyclohexyl, cycloheptyl, cyclooctyl, bicyclo[4.1.0]heptanyl, spiro[2.5]octanyl and dispiro[2.0.24.13]heptanyl, any of which groups may be optionally substituted by one or more substituents.

Suitable values of $R^5$ include cyclopentyl and cyclohexyl, either of which groups may be optionally substituted by one or more substituents.

Typical examples of optional substituents on $R^5$ include one, two or three substituents independently selected from halogen, cyano, nitro, $C_{1-6}$ alkyl, trifluoromethyl, phenyl, hydroxy, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on $R^5$ include one, two or three substituents independently selected from halogen, $C_{1-6}$ alkyl and trifluoromethyl.

Suitable examples of optional substituents on $R^5$ include one, two or three substituents independently selected from $C_{1-6}$ alkyl and trifluoromethyl.

Typical examples of particular substituents on $R^5$ include one, two or three substituents independently selected from fluoro, chloro, bromo, cyano, nitro, methyl, ethyl, isopropyl, tert-butyl, trifluoromethyl, phenyl, hydroxy, oxo, methoxy, tert-butoxy, difluoromethoxy, trifluoromethoxy, methylthio, methylsulfinyl, methyl sulfonyl, amino, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Selected examples of particular substituents on $R^5$ include one, two or three substituents independently selected from fluoro, methyl and trifluoromethyl.

Suitable examples of particular substituents on $R^5$ include one, two or three substituents independently selected from methyl and trifluoromethyl.

Illustrative examples of specific values of $R^5$ include hydrogen, methyl, isopropyl, 1-methylpropyl, 2-methylpropyl, cyclopropyl, cyclopentyl, indanyl, cyclohexyl, methylcyclohexyl, trifluoromethylcyclohexyl, difluorocyclohexyl, dimethylcyclohexyl, cycloheptyl, cyclooctyl, cyclohexylmethyl, cyclooctenyl, bicyclo[4.1.0]heptanyl, spiro-[3.3]heptanyl, spiro[2.5]octanyl, dispiro[2.0.24.13]heptanyl, phenyl, chlorophenyl, benzyl, fluorobenzyl, chlorobenzyl, (chloro)(fluoro)benzyl, dichlorobenzyl, bromobenzyl, cyanobenzyl, methylbenzyl, trifluoromethylbenzyl, phenylbenzyl, hydroxybenzyl, methoxybenzyl, tert-butoxybenzyl, aminocarbonylbenzyl, phenylethyl, chlorophenylethyl, naphthylmethyl, thienylmethyl, indolylmethyl and pyridinylmethyl.

Apposite examples of specific values of $R^5$ include cyclopentyl, cyclohexyl, methylcyclohexyl, trifluoromethylcyclohexyl, difluorocyclohexyl, dimethylcyclohexyl, cycloheptyl, cyclooctyl, bicyclo[4.1.0]heptanyl, spiro[2.5]octanyl and dispiro[2.0.24.13]-heptanyl.

Selected examples of specific values of $R^5$ include cyclopentyl, methylcyclohexyl, trifluoromethylcyclohexyl and difluorocyclohexyl.

Representative examples of specific values of $R^5$ include cyclopentyl, methylcyclohexyl and trifluoromethylcyclohexyl.

In a first embodiment, $R^5$ represents cyclopentyl. In a second embodiment, $R^5$ represents methylcyclohexyl, especially 4-methylcyclohexyl. In a third embodiment, $R^5$ represents trifluoromethylcyclohexyl, especially 4-(trifluoromethyl)cyclohexyl. In a fourth embodiment, $R^5$ represents difluorocyclohexyl, especially 4,4-difluorocyclohexyl.

In a first embodiment, $R^{5a}$ represents optionally substituted $C_{3-7}$ cycloalkyl. In a second embodiment, $R^{5a}$ represents optionally substituted $C_{4-9}$ bicycloalkyl. In a third embodiment, $R^{5a}$ represents optionally substituted aryl. In a fourth embodiment, $R^{5a}$ represents optionally substituted $C_{3-7}$ heterocycloalkyl. In a fifth embodiment, $R^{5a}$ represents optionally substituted heteroaryl.

Typical values of $R^{5a}$ include cyclobutyl, cyclopentyl, bicyclo[1.1.1]pentanyl, phenyl, dihydrobenzofuranyl and pyrrolyl, any of which groups may be optionally substituted by one or more substituents.

Typical examples of optional substituents on $R^{5a}$ include $C_{1-6}$ alkyl, halogen, cyano, trifluoromethyl, trifluoroethyl, phenyl, hydroxy, $C_{1-6}$ alkoxy, $C_{1-6}$ alkylthio, $C_{1-6}$ alkylsulfinyl, $C_{1-6}$ alkylsulfonyl, $C_{2-6}$ alkylcarbonyl, amino, $C_{1-6}$ alkylamino and di($C_{1-6}$)alkylamino.

Selected examples of optional substituents on $R^{5a}$ include $C_{1-6}$ alkyl and halogen.

Typical examples of particular substituents on $R^{5a}$ include methyl, fluoro, chloro, bromo, cyano, trifluoromethyl, trifluoroethyl, phenyl, hydroxy, methoxy, methylthio, methylsulfinyl, methylsulfonyl, acetyl, amino, methylamino and dimethylamino.

Selected examples of particular substituents on $R^{5a}$ include methyl and chloro.

Selected values of $R^{5a}$ include cyclobutyl, cyclopentyl, bicyclo[1.1.1]pentanyl, phenyl, chlorophenyl, dihydrobenzofuranyl and methylpyrrolyl.

Suitably, $R^{5b}$ represents hydrogen, methyl or ethyl.

In a first embodiment, $R^{5b}$ represents hydrogen. In a second embodiment, $R^{5b}$ represents $C_{1-6}$ alkyl, especially methyl or ethyl.

Alternatively, $R^{5a}$ and $R^{5b}$, when taken together with the carbon atom to which they are both attached, may represent $C_{3-7}$ cycloalkyl, $C_{4-9}$ bicycloalkyl or $C_{3-7}$ heterocycloalkyl, any of which groups may be unsubstituted, or substituted by one or more substituents, typically by one or two substituents.

In a first embodiment, $R^{5a}$ and $R^{5b}$, when taken together with the carbon atom to which they are both attached, may suitably represent optionally substituted $C_{3-7}$ cycloalkyl. Examples include cyclobutyl, benzocyclobutenyl, cyclopentyl, indanyl, cyclohexyl, tetrahydronaphthalenyl, cycloheptanyl, benzocycloheptenyl, cyclooctanyl and cyclononanyl, any of which groups may be optionally substituted by one or more substituents.

In a second embodiment, $R^{5a}$ and $R^{5b}$, when taken together with the carbon atom to which they are both attached, may suitably represent optionally substituted $C_{4-9}$ bicycloalkyl. Examples include bicyclo[3.1.0]hexanyl, bicyclo[2.2.1]heptanyl and bicyclo[3.2.1]octanyl, any of which groups may be optionally substituted by one or more substituents.

In a third embodiment, $R^{5a}$ and $R^{5b}$, when taken together with the carbon atom to which they are both attached, may suitably represent optionally substituted $C_{3-7}$ heterocycloalkyl. Examples include tetrahydropyranyl and piperidinyl, either of which groups may be optionally substituted by one or more substituents.

Typical examples of optional substituents on such groups include $C_{1-6}$ alkyl, halogen, cyano, trifluoromethyl, trifluoroethyl, phenyl, hydroxy, $C_{1-6}$ alkoxy, $C_{1-6}$ alkylthio, $C_{1-6}$ alkylsulfinyl, $C_{1-6}$ alkylsulfonyl, $C_{2-6}$ alkylcarbonyl, amino, $C_{1-6}$ alkylamino and di($C_{1-6}$)alkylamino.

Selected examples of optional substituents on such groups include $C_{1-6}$ alkyl, halogen, trifluoromethyl, trifluoroethyl, phenyl and $C_{1-6}$ alkoxy.

Typical examples of particular substituents on such groups include methyl, fluoro, chloro, bromo, cyano, trifluoromethyl, trifluoroethyl, phenyl, hydroxy, methoxy, methylthio, methylsulfinyl, methylsulfonyl, acetyl, amino, methylamino and dimethylamino.

Selected examples of particular substituents on such groups include methyl, chloro, trifluoromethyl, trifluoroethyl, phenyl and methoxy.

Selected values of $R^{5a}$ and $R^{5b}$, when taken together with the carbon atom to which they are both attached, include methylcyclobutyl, dimethylcyclobutyl, phenylcyclobutyl, benzocyclobutenyl, methylbenzocyclobutenyl, chlorobenzocyclobutenyl, methoxy-benzocyclobutenyl, cyclopentyl, methylcyclopentyl, indanyl, chloroindanyl, cyclohexyl, methylcyclohexyl, dimethylcyclohexyl, trifluoromethylcyclohexyl, tetrahydronaphthalenyl, cycloheptanyl, benzocycloheptenyl, cyclooctanyl, cyclononanyl, bicyclo[3.1.0]hexanyl, bicyclo[2.2.1]heptanyl, bicyclo[3.2.1]octanyl, tetramethyl-tetrahydropyranyl and trifluoroethylpiperidinyl.

Typically, $R^6$ represents —$OR^6$ or —$NR^{6b}R^{6c}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, heteroaryl or heteroaryl-($C_{1-6}$)alkyl, any of which groups may be optionally substituted by one or more substituents.

Suitably, $R^6$ represents —$OR^{6a}$; or $R^6$ represents $C_{1-6}$ alkyl, aryl or heteroaryl, any of which groups may be optionally substituted by one or more substituents.

More suitably, $R^6$ represents $C_{1-6}$ alkyl or heteroaryl, either of which groups may be optionally substituted by one or more substituents.

Appositely, $R^6$ represents —$OR^{6a}$; or $R^6$ represents heteroaryl, which group may be optionally substituted by one or more substituents.

In a first embodiment, $R^6$ represents optionally substituted $C_{1-6}$ alkyl. In a second embodiment, $R^6$ represents optionally substituted $C_{3-9}$ cycloalkyl. In a third embodiment, $R^6$ represents optionally substituted $C_{3-9}$ cycloalkyl($C_{1-6}$)alkyl. In a fourth embodiment, $R^6$ represents optionally substituted aryl. In a fifth embodiment, $R^6$ represents optionally substituted aryl($C_{1-6}$)alkyl. In a sixth embodiment, $R^6$ represents optionally substituted $C_{3-7}$ heterocycloalkyl. In a seventh embodiment, $R^6$ represents optionally substituted $C_{3-7}$ heterocycloalkyl($C_{1-6}$)alkyl. In an eighth embodiment, $R^6$ represents optionally substituted heteroaryl. In a ninth embodiment, $R^6$ represents optionally substituted heteroaryl($C_{1-6}$)alkyl. In a tenth embodiment, $R^6$ represents —$OR^{6a}$. In an eleventh embodiment, $R^6$ represents —$NR^{6a}R^{6b}$.

Typical values of $R^6$ include —$OR^{6a}$ or —$NR^{6a}R^{6b}$; and methyl, ethyl, propyl, 2-methylpropyl, butyl, cyclopropyl, cyclobutyl, cyclohexyl, cyclohexylmethyl, phenyl, benzyl, phenylethyl, pyrazolyl, isoxazolyl, imidazolyl, oxadiazolyl, triazolyl, pyridinyl, triazolylmethyl, benzotriazolylmethyl or pyridinylmethyl, any of which groups may be optionally substituted by one or more substituents. Additional values include furyl and thiazolyl, either of which groups may be optionally substituted by one or more substituents.

Illustrative values of $R^6$ include —$OR^{6a}$; and methyl, phenyl, pyrazolyl, isoxazolyl, imidazolyl, oxadiazolyl or triazolyl, any of which groups may be optionally substituted by one or more substituents.

Selected values of $R^6$ include 2-methylpropyl, furyl, pyrazolyl and thiazolyl, any of which groups may be optionally substituted by one or more substituents.

Suitable values of $R^6$ include pyrazolyl, which group may be optionally substituted by one or more substituents.

Typical examples of optional substituents on $R^6$ include one, two or three substituents independently selected from halogen, cyano, nitro, $C_{1-6}$ alkyl, trifluoromethyl, phenyl, fluorophenyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$) alkyl, $C_{1-6}$ alkylamino, di($C_{1-6}$)alkylamino, pyrrolidinyl, tetrahydropyranyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl and di-($C_{1-6}$)alkylsulfoximinyl.

Selected examples of optional substituents on $R^6$ include one, two or three substituents independently selected from halogen and $C_{1-6}$ alkyl.

Suitable examples of optional substituents on $R^6$ include one, two or three substituents independently selected from $C_{1-6}$ alkyl.

Typical examples of particular substituents on $R^6$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, tetrahydropyranyl, morpholinyl, piperazinyl, acetylamino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl, dimethylaminosulfonyl and dimethylsulfoximinyl.

Selected examples of particular substituents on $R^6$ include one, two or three substituents independently selected from chloro, methyl and ethyl.

Suitable examples of particular substituents on $R^6$ include one, two or three substituents independently selected from ethyl.

Illustrative examples of particular values of $R^6$ include methyl, difluoromethyl, methylsulfonylmethyl, aminomethyl, methylaminomethyl, difluoroethyl, carboxyethyl, difluoropropyl, 2-methylpropyl, butyl, cyanocyclopropyl, methylcyclopropyl, ethyl-cyclopropyl, dimethylcyclopropyl, trifluoromethylcyclopropyl, phenylcyclopropyl, fluorophenylcyclopropyl, hydroxycyclopropyl, aminocyclopropyl, cyclobutyl, trifluoromethylcyclobutyl, cyclohexyl, cyclohexylmethyl, phenyl, fluorophenyl, chlorophenyl, cyanophenyl, methylphenyl, hydroxyphenyl, methylsulfonylphenyl, dimethyl-sulfoximinylphenyl, benzyl, fluorobenzyl, difluorobenzyl, chlorobenzyl, (chloro)(fluoro)-benzyl, dichlorobenzyl, (chloro)(difluoro)benzyl, bromobenzyl, cyanobenzyl, methylbenzyl, dimethylbenzyl, trifluoromethylbenzyl, phenylbenzyl, hydroxybenzyl, hydroxymethylbenzyl, benzoyl, methoxybenzyl, dimethoxybenzyl, trifluoromethoxy-benzyl, methyl sulfonylbenzyl, aminomethylbenzyl, aminoethylbenzyl, dimethylaminobenzyl, pyrrolidinylbenzyl, (dimethyl)(pyrrolidinyl)benzyl, morpholinylbenzyl, (dimethyl)(morpholinyl)benzyl, piperazinylbenzyl, acetylaminoethylbenzyl, phenylethyl, chlorophenylethyl, methylpyrazolyl, ethylpyrazolyl, (methyl)(tetrahydropyranyl)pyrazolyl, methylisoxazolyl, ethylisoxazolyl, methylimidazolyl, dimethylimidazolyl, methyloxadiazolyl, ethyloxadiazolyl, methyltriazolyl, ethyltriazolyl, pyridinyl, triazolylmethyl, benzotriazolylmethyl, pyridinylmethyl and aminopyridinylmethyl. Additional examples include dimethylfuryl, dimethylpyrazolyl and chlorothiazolyl.

Selected examples of particular values of $R^6$ include 2-methylpropyl, dimethylfuryl, ethylpyrazolyl, dimethylpyrazolyl and chlorothiazolyl.

Typical examples of particular values of $R^6$ include ethylpyrazolyl.

Generally, $R^{6a}$ represents $C_{1-6}$ alkyl.

In a first embodiment, $R^{6a}$ represents $C_{1-6}$ alkyl. In a second embodiment, Rha represents optionally substituted $C_{3-9}$ cycloalkyl.

Typically, $R^{6a}$ represents $C_{1-6}$ alkyl; or $R^{6a}$ represents cyclobutyl, which group may be optionally substituted by one or more substituents.

Typical examples of optional substituents on $R^{6a}$ include one, two or three substituents independently selected from halogen, cyano, nitro, $C_{1-6}$ alkyl, trifluoromethyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkyl sulfonyl, amino, amino($C_{1-6}$)alkyl, $C_{1-6}$ alkylamino, di ($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on $R^{6a}$ include one, two or three substituents independently selected from halogen.

Typical examples of specific substituents on $R^{6a}$ include one, two or three substituents independently selected from fluoro, chloro, bromo, cyano, nitro, methyl, ethyl, isopropyl, tert-butyl, trifluoromethylhydroxy, hydroxymethyl, oxo, methoxy, tert-butoxy, difluoromethoxy, trifluoromethoxy, methylthio, methylsulfinyl, methyl sulfonyl, amino, aminomethyl, aminoethyl, methylamino, tert-butylamino, dimethylamino, acetylamino, methoxycarbonylamino, methyl sulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Suitable examples of specific substituents on $R^{6a}$ include one, two or three substituents independently selected from fluoro.

Illustrative examples of specific values of $R^{6a}$ include methyl, ethyl, n-propyl, isopropyl, n-butyl, tert-butyl and difluorocyclobutyl.

Suitable examples of specific values of $R^{6a}$ include tert-butyl and difluorocyclobutyl.

Typically, $R^{6a}$ represents tert-butyl.

Typically, $R^{6b}$ represents hydrogen or methyl.

In a first embodiment, $R^{6b}$ represents hydrogen. In a second embodiment, $R^{6b}$ represents $C_{1-6}$ alkyl, especially methyl.

Typically, $R^{6c}$ represents hydrogen or methyl.

In a first embodiment, $R^{6c}$ represents hydrogen. In a second embodiment, $R^{6c}$ represents $C_{1-6}$ alkyl, especially methyl.

In a first embodiment, $R^7$ represents aryl, which group may be optionally substituted by one or more substituents. In a second embodiment, $R^7$ represents heteroaryl, which group may be optionally substituted by one or more substituents. In a third embodiment, $R^7$ represents spiro[($C_{3-7}$) heterocycloalkyl][heteroaryl], which group may be optionally substituted by one or more substituents.

Typical values of $R^7$ include phenyl, pyrazolo[1,5-a] pyrazinyl, benzoxazolyl, benzothiazolyl, benzimidazolyl, imidazo[1,2-b]pyridazinyl, imidazo[1,2-c]pyrimidinyl, purinyl, pyridinyl, pyridazinyl, cinnolinyl, pyrimidinyl, pyrazinyl and spiro[tetrahydropyranyl][indole], any of which groups may be optionally substituted by one or more substituents. Additional values include isoxazolo[4,5-b]pyridinyl and oxadiazolyl.

Select values of $R^7$ include isoxazolo[4,5-b]pyridinyl, imidazo[1,2-c]pyrimidinyl, oxadiazolyl, pyridinyl, pyridazinyl and pyrazinyl, any of which groups may be optionally substituted by one or more substituents.

Suitable values of $R^7$ include imidazo[1,2-c]pyrimidinyl and pyridazinyl, either of which groups may be optionally substituted by one or more substituents.

Typical examples of optional substituents on $R^7$ include one, two or three substituents independently selected from halogen, cyano, nitro, $C_{1-6}$ alkyl, difluoromethyl, trifluoromethyl, phenyl, fluorophenyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkyl sulfonyl, amino, amino($C_{1-6}$)alkyl, $C_{1-6}$ alkylamino, di($C_{1-6}$)alkylamino, pyrrolidinyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl. Additional examples include tetrahydropyranyl.

Selected examples of optional substituents on $R^7$ include one, two or three substituents independently selected from $C_{1-6}$ alkyl, difluoromethyl and tetrahydropyranyl.

Suitable examples of optional substituents on $R^7$ include one, two or three substituents independently selected from difluoromethyl.

Typical examples of particular substituents on $R^7$ include one, two or three substituents independently selected from fluoro, chloro, bromo, cyano, nitro, methyl, ethyl, isopropyl, tert-butyl, difluoromethyl, trifluoromethyl, phenyl, fluorophenyl, hydroxy, hydroxymethyl, oxo, methoxy, isopropoxy, tert-butoxy, difluoromethoxy, trifluoromethoxy, methylthio, methylsulfinyl, methyl sulfonyl, amino, aminomethyl, aminoethyl, methylamino, tert-butylamino, dimethylamino, pyrrolidinyl, morpholinyl, piperazinyl, acetylamino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl. Additional examples include tetrahydropyranyl.

Selected examples of particular substituents on $R^7$ include one, two or three substituents independently selected from methyl, isopropyl, difluoromethyl and tetrahydropyranyl.

Typical examples of particular substituents on $R^7$ include one, two or three substituents independently selected from difluoromethyl.

Illustrative values of $R^7$ include phenyl, pyrazolo[1,5-a] pyrazinyl, benzoxazolyl, fluorobenzoxazolyl, methylbenzoxazolyl, benzothiazolyl, benzimidazolyl, fluoro-benzimidazolyl, imidazo[1,2-b]pyridazinyl, imidazo[1,2-c] pyrimidinyl, purinyl, pyridinyl, cyanopyridinyl, methylpyridinyl, methoxypyridinyl, pyridazinyl, chloropyridazinyl, cyanopyridazinyl, methylpyridazinyl, ethylpyridazinyl, isopropylpyridazinyl, difluoromethylpyridazinyl, trifluoromethylpyridazinyl, methoxypyridazinyl, isopropoxy-pyridazinyl, difluoromethoxypyridazinyl, dimethylaminopyridazinyl, cinnolinyl, pyrimidinyl, pyrazinyl, methylpyrazinyl and spiro[tetrahydropyranyl][oxoindole]. Additional values include isoxazolo[4,5-b]pyridinyl, methyloxadiazolyl, isopropyloxadiazolyl, tetrahydropyranyloxadiazolyl and difluoromethylpyridinyl.

Favoured values of $R^7$ include isoxazolo[4,5-b]pyridinyl, imidazo[1,2-c]-pyrimidinyl, methyloxadiazolyl, isopropyloxadiazolyl, tetrahydropyranyloxadiazolyl, pyridinyl, difluoromethylpyridinyl, difluoromethylpyridazinyl and pyrazinyl.

Representative values of $R^7$ include imidazo[1,2-c]pyrimidinyl and difluoromethylpyridazinyl.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$) alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkyl sulphonylamino, aminocarbonyl, $C_{1-6}$ alkylaminocarbonyl and di($C_{1-6}$)alkylaminocarbonyl.

Typical examples of particular substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methyl sulphonylamino, aminocarbonyl, methylaminocarbonyl and dimethylaminocarbonyl.

In general, $R^a$ represents $C_{1-6}$ alkyl, $C_{3-9}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted by one or more substituents.

Appositely, $R^a$ represents $C_{1-6}$ alkyl, $C_{3-9}$ cycloalkyl, aryl, $C_{3-7}$ heterocycloalkyl or heteroaryl, any of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Illustrative values of $R^a$ include methyl, ethyl, cyclopropyl, phenyl, benzyl, oxetanyl, tetrahydropyranyl, piperidinyl, pyridinyl, pyridazinyl and isoindolylpropyl, any of which groups may be optionally substituted by one or more substituents.

Representative values of $R^a$ include methyl, cyclopentyl, phenyl, oxetanyl, tetrahydropyranyl, piperidinyl, pyridinyl and pyridazinyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy, oxo and $C_{1-6}$ alkylsulfonyl.

Selected examples of specific substituents on $R^a$ include methoxy, oxo and methylsulfonyl.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl. In a further embodiment, $R^a$ represents optionally substituted $C_{3-9}$ cycloalkyl, e.g. cyclopentyl. In a further embodiment, $R^a$ represents optionally substituted $C_{3-7}$ heterocycloalkyl.

Particular values of $R^a$ include methyl, methoxyethyl, cyclopentyl, phenyl, benzyl, oxetanyl, tetrahydropyranyl, methylsulfonylpiperidinyl, dioxoisoindolylpropyl, pyridinyl and pyridazinyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of Rb include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methyl sulphonylethyl, hydroxyethyl, cyanoethyl, dimethylaminoethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

Favourably, $R^c$ represents $C_{3-7}$ heterocycloalkyl, which group may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected values of $R^c$ include tetrahydropyranyl and piperidinyl, either of which groups may be optionally substituted by one or more substituents.

Selected examples of suitable substituents on $R^c$ include $C_{1-6}$ alkylsulfonyl, $C_{2-6}$ alkylcarbonyl and $C_{2-6}$ alkoxycarbonyl.

Selected examples of specific substituents on $R^c$ include methylsulfonyl, acetyl and tert-butoxycarbonyl.

Specific values of $R^c$ include hydrogen, methyl, cyclobutyl, cyclopentyl, cyclohexyl, tetrahydropyranyl, methyl sulfonylpiperidinyl, acetylpiperidinyl and tert-butoxycarbonylpiperidinyl.

Particular values of $R^c$ include tetrahydropyranyl and methylsulfonylpiperidinyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkyl-sulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, amino-azetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

A first sub-class of compounds according to the invention is represented by the compounds of formula (IIA) and N-oxides thereof, and pharmaceutically acceptable salts thereof:

(IIA)

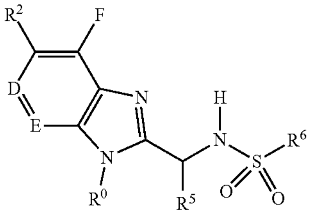

wherein

D, E, $R^2$, $R^5$ and $R^6$ are as defined above.

A second sub-class of compounds according to the invention is represented by the compounds of formula (JIB) and N-oxides thereof, and pharmaceutically acceptable salts thereof:

(IIB)

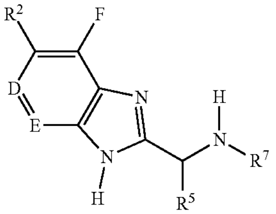

wherein

D, E, $R^2$, $R^5$ and $R^7$ are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments, including inflammatory and autoimmune disorders.

The compounds according to the present invention are useful in the treatment and/or prophylaxis of a pathological disorder that is mediated by a pro-inflammatory IL-17 cytokine or is associated with an increased level of a pro-inflammatory IL-17 cytokine. Generally, the pathological condition is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury, pelvic inflammatory disease, Alzheimer's Disease, Crohn's disease, inflammatory bowel disease, irritable bowel syndrome, ulcerative colitis, Castleman's disease, ankylosing spondylitis and other spondyloarthropathies, dermatomyositis, myocarditis, uveitis, exophthalmos, autoimmune thyroiditis, Peyronie's Disease, coeliac disease, gall bladder disease, Pilonidal disease, peritonitis, psoriasis, atopic dermatitis, vasculitis, surgical adhesions, stroke, autoimmune diabetes, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, chronic lymphatic leukemia, gastric cancer and colon cancer), heart disease including ischaemic diseases such as myocardial infarction as well as atherosclerosis, intravascular coagulation, bone resorption, osteoporosis, periodontitis, hypochlorhydia and pain (particularly pain associated with inflammation).

WO 2009/089036 reveals that modulators of IL-17 activity may be administered to inhibit or reduce the severity of ocular inflammatory disorders, in particular ocular surface inflammatory disorders including Dry Eye Syndrome (DES). Consequently, the compounds in accordance with the present invention are useful in the treatment and/or prevention of an IL-17-mediated ocular inflammatory disorder, in particular an IL-17-mediated ocular surface inflammatory disorder including Dry Eye Syndrome. Ocular surface inflammatory disorders include Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory conditions, conjunctival scarring disorders, ocular autoimmune conditions, Pemphigoid syndrome, Stevens-Johnson syndrome, ocular allergy, severe allergic (atopic) eye disease, conjunctivitis and microbial keratitis. Particular categories of Dry Eye Syndrome include keratoconjunctivitis sicca (KCS), Sjögren syndrome, Sjögren syndrome-associated keratoconjunctivitis sicca, non-Sjögren syndrome-associated keratoconjunctivitis sicca, keratitis sicca, sicca syndrome, xerophthalmia, tear film disorder, decreased tear production, aqueous tear deficiency (ATD), meibomian gland dysfunction and evaporative loss.

Illustratively, the compounds of the present invention may be useful in the treatment and/or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, inflammatory bowel diseases (including Crohn's disease and ulcerative colitis), ankylosing spondylitis and other spondyloarthropathies, cancer and pain (particularly pain associated with inflammation).

Suitably, the compounds of the present invention are useful in the treatment and/or prophylaxis of psoriasis, psoriatic arthritis or ankylosing spondylitis.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds according to the present invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds according to the present invention may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate.

Alternatively, for ophthalmic administration the compounds according to the present invention may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound according to the present invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (IA) above may be prepared by a two-step procedure which comprises: (i) reacting a compound of formula $R^6$—CHO with a compound of formula (III):

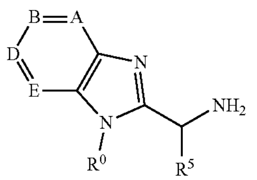

(III)

wherein A, B, D, E, $R^0$, $R^5$ and $R^6$ are as defined above; and (ii) treating the material thereby obtained with a reducing agent.

Step (i) is conveniently accomplished at ambient temperature in the presence of acetic acid in a suitable solvent, e.g. a cyclic ether such as tetrahydrofuran.

Suitably, the reducing agent of use in step (ii) comprises a cyanoborohydride salt. Typical cyanoborohydride salts include macroporous polymer supported cyanoborohydride (MP-$BH_3CN$), in which case the reaction is conveniently effected at ambient temperature in a suitable solvent, e.g. a $C_{1-4}$ alkanol such as ethanol.

The compounds of formula (TB) above may be prepared by a process which comprises reacting a compound of formula (III) as defined above with a compound of formula $L^1$-$S(O)_2R^6$, wherein $R^6$ is as defined above, and $L^1$ represents a suitable leaving group.

The leaving group $L^1$ is suitably a halogen atom, e.g. chloro.

The reaction is conveniently carried out at ambient temperature in the presence of pyridine. Alternatively, the reaction may be carried out at ambient temperature in the presence of a base, e.g. an organic amine such as N,N-diisopropylethylamine, in a suitable solvent, e.g. a chlorinated solvent such as dichloromethane.

The compounds of formula (IC) above may be prepared by a process which comprises reacting a compound of formula (III) as defined above with a compound of formula $L^2$-$R^7$, wherein $R^7$ is as defined above, and $L^2$ represents a suitable leaving group.

The leaving group $L^2$ is suitably a halogen atom, e.g. chloro or bromo.

The reaction is conveniently carried out in the presence of a base. Suitable bases include organic amines, e.g. a trialkylamine such as N,N-diisopropylethylamine. The reaction is typically performed at an elevated temperature in a suitable solvent, e.g. a cyclic ether such as 1,4-dioxane, or a cyclic amide such as 1-methyl-2-pyrrolidinone, or an organic sulfoxide such as dimethyl sulfoxide.

Alternatively, the reaction may be performed in the presence of a transition metal catalyst. Suitable transition metal catalysts of use in this procedure include the following:

[(2-di-tert-butylphosphino-3,6-dimethoxy-2',4',6'-triisopropyl-1,1'-biphenyl)-2-(2'-amino-1,1'-biphenyl)]palladium(II) methanesulfonate (tBuBrettPhos Pd G3);

[(2-dicyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3), generally in conjunction with 2-(dicyclohexylphosphino)-3,6-dimethoxy-2',4',6'-triisopropyl-1,1'-biphenyl (BrettPhos);

bis{[2-(diadamantylphosphino)-3-methoxy-2,4,6-triisopropyl-3-(2,3,5,6-tetrafluoro-4-butylphenyl)-1,1-biphenyl]palladium(O)}1,5-cyclooctadiene (AlPhos palladium complex);

{[2',6'-bis(dimethylamino)-2-(tert-butyl)(phenyl)phosphino-1,1'-biphenyl]-2-(2'-amino-1,1'-biphenyl)}palladium(II) methanesulfonate [(tBu)PhCPhos Pd G3];

{[2',6'-bis(dimethylamino)-2-(tert-butyl)(phenyl)phosphino-1,1'-biphenyl]-2-(2'-methylamino-1,1'-biphenyl)}palladium(II) methanesulfonate [(tBu)PhCPhos Pd G4]; and copper(I) iodide, generally in conjunction with potassium phosphate.

The reaction is conveniently carried out at an elevated temperature in the presence of a base. Suitable bases include the following:

a tert-butoxide salt such as potassium tert-butoxide or sodium tert-butoxide;

lithium bis(trimethylsilyl)amide; and 1,8-diazabicyclo[5.4.0]undec-7-ene (DBU).

Moreover, the reaction is conveniently effected in a suitable solvent or solvent mixture. The solvent or solvents may suitably be selected from a cyclic ether such as 1,4-dioxane or tetrahydrofuran; a dialkyl ether such as tert-butyl methyl ether; a $C_{1-6}$ alkanol such as n-butanol; a lower alkylene glycol such as ethylene glycol; and a sulfoxide solvent such as dimethyl sulfoxide.

In a particular procedure, the compounds of formula (IC) above wherein $R^7$ represents a 5-substituted 1,2,4-oxadiazol-3-yl moiety may be prepared by a three-step process which comprises the following steps:

(i) reacting a compound of formula (III) as defined above with cyanogen bromide;

(ii) reacting the resulting material with hydroxyammonium chloride; and (iii) reacting the material thereby obtained with the appropriate carboxylic acid chloride derivative.

Step (i) is conveniently effected in the presence of a base, e.g. an alkali metal bicarbonate such as sodium bicarbonate.

Step (ii) is conveniently performed at an elevated temperature in the presence of a base, e.g. an alkali metal carbonate such as sodium carbonate.

Step (iii) is conveniently accomplished in the presence of pyridine.

The intermediates of formula (III) above wherein $R^0$ represents hydrogen may be prepared by a three-step procedure which comprises the following steps:

(i) reacting a compound of formula (IV) with a compound of formula (V):

(IV)

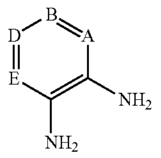

(V)

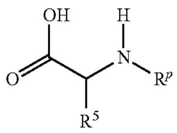

wherein A, B, D, E and $R^5$ are as defined above, and $R^p$ represents a N-protecting group;

(ii) cyclisation of the resulting material; and (iii) removal of the N-protecting group $R^p$.

The N-protecting group $R^p$ will suitably be tert-butoxycarbonyl (BOC). Alternatively, the N-protecting group $R^p$ may be benzyloxycarbonyl.

Step (i) is conveniently accomplished in the presence of a coupling agent and a base. Suitable coupling agents include 1-[bis(dimethylamino)methylene]-1H-1,2,3-triazolo[4,5-b]pyridinium 3-oxid hexafluorophosphate (HATU); and 2,4,6-tripropyl-1,3,5,2,4,6-trioxatriphosphorinane-2,4,6-trioxide. Suitable bases include organic amines, e.g. a trialkylamine such as N,N-diisopropylethylamine. The reaction is conveniently performed at ambient or elevated temperature in a suitable solvent, e.g. a cyclic ether such as tetrahydrofuran, or a dipolar aprotic solvent such as N,N-dimethylformamide, or a chlorinated solvent such as dichloromethane.

Cyclisation step (ii) is conveniently effected by heating in a suitable medium, e.g. acetic acid.

Where the N-protecting group $R^p$ is BOC, the removal thereof in step (iii) may conveniently be effected by treatment with an acid, e.g. a mineral acid such as hydrochloric acid, or an organic acid such as trifluoroacetic acid.

Where the N-protecting group $R^p$ is benzyloxycarbonyl, the removal thereof in step (iii) may conveniently be effected by catalytic hydrogenation, typically by treatment with hydrogen gas or ammonium formate in the presence of a hydrogenation catalyst, e.g. palladium on charcoal, or palladium hydroxide on charcoal.

Alternatively, the intermediates of formula (III) above wherein $R^0$ represents hydrogen may be prepared by a procedure which comprises the following steps:

(i) reacting a compound of formula (VI) with a compound of formula (VII):

(VI)

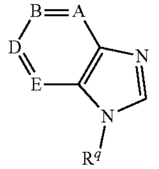

(VII)

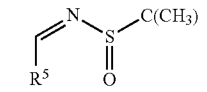

wherein A, B, D, E and $R^5$ are as defined above, and $R^q$ represents a N-protecting group; to provide a compound of formula (VIII):

(VIII)

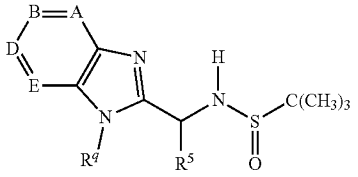

wherein A, B, D, E, $R^5$ and $R^q$ are as defined above; and (ii) removal of the tert-butylsulfinyl group and the N-protecting group $R^q$ from compound (VIII).

The N-protecting group $R^q$ will suitably be 2-(trimethylsilyl)ethoxymethyl.

Step (i) is suitably effected by treatment of compound (VI) with a base, e.g. an organic base such as n-butyllithium, followed by reaction with compound (VII). The reaction is conveniently accomplished in a suitable solvent, e.g. a cyclic ether such as tetrahydrofuran.

Where the N-protecting group $R^q$ is 2-(trimethylsilyl)ethoxymethyl, removal of the tert-butylsulfinyl group and the N-protecting group $R^q$ from compound (VIII) in step (ii) may both be accomplished by treatment with an acid, e.g. a mineral acid such as hydrochloric acid.

Where the N-protecting group $R^q$ is 2-(trimethylsilyl)ethoxymethyl, the intermediates of formula (VI) above may be prepared by a procedure which comprises the following steps:

(i) reaction of a compound of formula (IV) as defined above with formic acid; and (ii) reaction of the material thereby obtained with 2-(trimethylsilyl)ethoxymethyl chloride.

Step (i) is conveniently carried out at an elevated temperature.

Step (ii) is suitably effected by treating the reactants with a base, e.g. an inorganic base such as sodium hydride; or an organic base such as N,N-diisopropylethylamine.

The intermediates of formula (VII) above may be prepared by reacting an aldehyde derivative of formula $R^5$—CHO with 2-methyl-2-propanesulfinamide. The reaction is suitably effected in the presence of pyridinium p-toluenesulfonate and magnesium sulfate. The reaction is conveniently carried out at ambient temperature in a suitable solvent, e.g. a chlorinated solvent such as dichloromethane.

The compounds of formula (ID) above may be prepared by a process which comprises reacting a compound of formula $R^7$—$NH_2$ with a compound of formula (IX):

(IX)

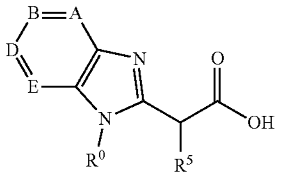

wherein A, B, D, E, $R^0$, $R^5$ and $R^7$ are as defined above; under conditions analogous to those described above for the reaction between compounds (IV) and (V).

The intermediates of formula (IX) above may be prepared by a two-step procedure which comprises: (i) reacting a compound of formula (IV) as defined above with a compound of formula (X), or a salt thereof, e.g. a lithium salt thereof:

(X)

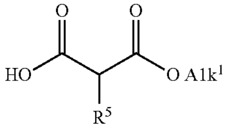

wherein $R^5$ is as defined above, and $Alk^1$ represents $C_{1-6}$ alkyl, e.g. methyl; under conditions analogous to those described above for the reaction between compounds (IV) and (V); and (ii) saponification of the resulting material by treatment with a base.

The saponification reaction in step (ii) will generally be effected by treatment with a base. Suitable bases include inorganic hydroxides, e.g. an alkali metal hydroxide such as lithium hydroxide. Where lithium hydroxide is employed in step (ii) of the above procedure, the product may be the lithium salt of the carboxylic acid of formula (IX).

Step (ii) is conveniently effected at ambient temperature in water and a suitable organic solvent, e.g. a $C_{1-4}$ alkanol such as ethanol.

The compounds of formula (IE) above may be prepared by a process which comprises reacting a compound of formula (IV) as defined above with a compound of formula (XI):

(XI)

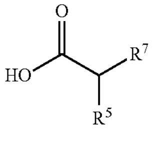

wherein $R^5$ and $R^7$ are as defined above; under conditions analogous to those described above for the reaction between compounds (IV) and (V).

The compounds of formula (IF) above may be prepared by a process which comprises reacting a compound of formula (IV) as defined above with a compound of formula (XII):

(XII)

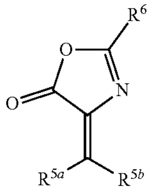

wherein $R^{5a}$, $R^{5b}$ and $R^6$ are as defined above.

The reaction will generally be performed in the presence of acetic acid. The reaction is conveniently carried out at an elevated temperature in a suitable solvent, e.g. a cyclic ether such as tetrahydrofuran.

The intermediates of formula (XII) above may be prepared by reacting a compound of formula $R^{5a}C(O)R^{5b}$ with a compound of formula (XIII):

(XIII)

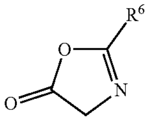

wherein $R^{5a}$, $R^{5b}$ and $R^6$ are as defined above.

The reaction is conveniently effected by treating the reagents with titanium tetrachloride; followed by treatment of the resulting material with pyridine.

Where they are not commercially available, the starting materials of formula (IV), (V), (X), (XI) and (XIII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) comprising a N-BOC moiety (wherein BOC is an abbreviation for tert-butoxycarbonyl) may be converted into the corresponding compound comprising a N—H moiety by treatment with an acid, e.g. a mineral acid such as hydrochloric acid, or an organic acid such as trifluoroacetic acid.

A compound of formula (I) comprising a N—H functionality may be alkylated, e.g. methylated, by treatment with a suitable alkyl halide, e.g. iodomethane, typically in the presence of a base, e.g. an inorganic carbonate such as sodium carbonate.

A compound of formula (I) comprising a N—H functionality may be acylated, e.g. acetylated, by treatment with a suitable acyl halide, e.g. acetyl chloride, typically in the presence of a base, e.g. an organic base such as N,N-diisopropylethylamine or triethylamine. Similarly, a compound of formula (I) comprising a N—H functionality may be acylated, e.g. acetylated, by treatment with a suitable acyl anhydride, e.g. acetic anhydride, typically in the presence of a base, e.g. an organic base such as triethylamine.

Similarly, a compound of formula (I) comprising a N—H functionality may be converted into the corresponding compound comprising a N—$S(O)_2Alk^1$ functionality (wherein $Alk^1$ is as defined above) by treatment with the appropriate $C_{1-4}$ alkylsulfonyl chloride reagent, e.g. methylsulfonyl chloride, typically in the presence of a base, e.g. an organic base such as triethylamine.

Similarly, a compound of formula (I) comprising a N—H functionality may be converted into the corresponding compound comprising a carbamate or urea moiety respectively by treatment with the appropriate chloroformate or carbamoyl chloride reagent, typically in the presence of a base, e.g. an organic base such as triethylamine. Alternatively, a compound of formula (I) comprising a N—H functionality may be converted into the corresponding compound comprising a urea moiety by treatment with the appropriate amine-substituted (3-methylimidazol-3-ium-1-yl)methanone iodide derivative, typically in the presence of a base, e.g. an organic base such as triethylamine. Alternatively, a compound of formula (I) comprising a N—H functionality may be converted into the corresponding compound comprising a urea moiety N—C(O)N(H)$Alk^1$ (wherein $Alk^1$ is as defined above) by treatment with the appropriate isocyanate derivative $Alk^1$-N═C═O, typically in the presence of a base, e.g. an organic base such as triethylamine.

A compound of formula (I) comprising a N—H functionality may be converted into the corresponding compound comprising a N—C(H) functionality by treatment with the appropriate aldehyde or ketone in the presence of a reducing agent such as sodium triacetoxyborohydride.

A compound of formula (I) comprising a $C_{1-4}$ alkoxycarbonyl moiety —$CO_2Alk^1$ (wherein $Alk^1$ is as defined above) may be converted into the corresponding compound comprising a carboxylic acid (—$CO_2H$) moiety by treatment with a base, e.g. an alkali metal hydroxide salt such as lithium hydroxide. Alternatively, a compound of formula (I) comprising a tert-butoxycarbonyl moiety may be converted into the corresponding compound comprising a carboxylic acid (—$CO_2H$) moiety by treatment with trifluoroacetic acid.

A compound of formula (I) comprising a carboxylic acid (—$CO_2H$) moiety may be converted into the corresponding compound comprising an amide moiety by treatment with the appropriate amine, under conditions analogous to those described above for the reaction between compounds (IV) and (V), step (i).

A compound of formula (I) comprising a $C_{1-4}$ alkoxycarbonyl moiety —$CO_2Alk^1$ (wherein $Alk^1$ is as defined above) may be converted into the corresponding compound comprising a hydroxymethyl (—$CH_2OH$) moiety by treatment with a reducing agent such as lithium aluminium hydride.

A compound of formula (I) comprising a $C_{1-4}$ alkylcarbonyloxy moiety —OC(O)$Alk^1$ (wherein $Alk^1$ is as defined above), e.g. acetoxy, may be converted into the corresponding compound comprising a hydroxy (—OH) moiety by treatment with a base, e.g. an alkali metal hydroxide salt such as sodium hydroxide.

A compound of formula (I) comprising a halogen atom, e.g. bromo, may be converted into the corresponding compound comprising an optionally substituted aryl, heterocycloalkenyl or heteroaryl moiety by treatment with the appropriately substituted aryl, heterocycloalkenyl or heteroaryl boronic acid or a cyclic ester thereof formed with an organic diol, e.g. pinacol, 1,3-propanediol or neopentyl glycol. The reaction is typically effected in the presence of a transition metal catalyst, and a base. The transition metal catalyst may be [1,1'-bis(diphenylphosphino)ferrocene]dichloropalladium(II). In the alternative, the transition metal catalyst may be tris(dibenzylideneacetone)dipalladium(O), which may advantageously be employed in conjunction with 2-dicyclohexylphosphino-2',4',6'-triisopropylbiphenyl (XPhos). Suitably, the base may be an inorganic base such as sodium carbonate or potassium carbonate.

A compound of formula (I) comprising a halogen atom, e.g. bromo, may be converted into the corresponding compound comprising an optionally substituted aryl or heteroaryl moiety via a two-step procedure which comprises: (i) reaction with bis(pinacolato)diboron; and (ii) reaction of the compound thereby obtained with an appropriately substituted bromoaryl or bromoheteroaryl derivative. Step (i) is conveniently effected in the presence of a transition metal catalyst such as [1,1'-bis-(diphenylphosphino)ferrocene] dichloropalladium(II), and potassium acetate. Step (ii) is conveniently effected in the presence of a transition metal catalyst such as [1,1'-bis-(diphenylphosphino)ferrocene] dichloropalladium(II), and a base, e.g. an inorganic base such as sodium carbonate or potassium carbonate.

A compound of formula (I) comprising a cyano (—CN) moiety may be converted into the corresponding compound comprising a 1-aminoethyl moiety by a two-step process which comprises: (i) reaction with methylmagnesium chloride, ideally in the presence of titanium(IV) isopropoxide; and (ii) treatment of the resulting material with a reducing agent such as sodium borohydride. If an excess of methylmagnesium chloride is employed in step (i), the corresponding compound comprising a 1-amino-1-methylethyl moiety may be obtained.

A compound of formula (I) comprising the moiety —S— may be converted into the corresponding compound comprising the moiety —S(O)(NH)— by treatment with (diacetoxyiodo)benzene and ammonium carbamate.

A compound of formula (I) comprising a C═C double bond may be converted into the corresponding compound comprising a CH—CH single bond by treatment with gaseous hydrogen in the presence of a hydrogenation catalyst, e.g. palladium on charcoal.

A compound of formula (I) comprising an aromatic nitrogen atom may be converted into the corresponding compound comprising an N-oxide moiety by treatment with a suitable oxidising agent, e.g. 3-chloroperbenzoic acid.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Greene's Protective Groups in Organic Synthesis*, ed. P. G. M. Wuts, John Wiley & Sons, 5th edition, 2014. The protecting groups may be removed at any convenient subsequent stage utilising methods known from the art.

The compounds in accordance with this invention potently inhibit the ability of IL-17A to bind to IL-17RA. When tested in the IL-17 FRET assay described below, compounds of the present invention exhibit an $IC_{50}$ value of 10 μM or less, generally of 5 μM or less, usually of 1 μM or less, typically of 500 nM or less, suitably of 100 nM or less, ideally of 50 nM or less, and preferably of 25 nM or less (the skilled person will appreciate that a lower $IC_{50}$ figure denotes a more active compound).

Moreover, certain compounds in accordance with this invention potently inhibit IL-17 induced IL-6 release from human dermal fibroblasts. Indeed, when tested in the HDF cell line assay described below, compounds of the present invention exhibit an $IC_{50}$ value of 10 μM or less, generally of 5 μM or less, usually of 1 μM or less, typically of 500 nM or less, suitably of 100 nM or less, ideally of 50 nM or less, and preferably of 25 nM or less (as before, the skilled person will appreciate that a lower $IC_{50}$ figure denotes a more active compound).

IL-17 FRET Assay

The purpose of this assay is to test the ability of compounds to disrupt the interaction between IL-17A and soluble IL-17 Receptor A (IL-17RA). The ability of a compound to inhibit IL-17A binding to IL-17RA is measured in this assay.

An IL-17AA-TEV-Human Fc construct was expressed in a CHO SXE cell system and purified by protein A chromatography and size exclusion. The protein was labelled with an amine reactive AlexaFluor 647 dye (Thermo Fisher #A20006), as per manufacturer's instruction.

Soluble IL-17RA (33-317)-HKH-TEV-Fc was expressed in an Expi HEK293 cell system and purified by protein A chromatography and size exclusion. The Fc tag was cleaved by TEV, producing IL-17RA (33-317)-HKH, and the protein was labelled with amine reactive terbium (Thermo Fisher #PV3581).

In assay buffer [Dulbecco's PBS (Sigma #14190-094), 0.05% P20 (Thermo Scientific #28320), 1 mg/mL BSA (Sigma #A2153-500G)] the following solutions were prepared:

For IL-17A assay

IL-17A-Fc-AF647 at 5 nM

IL-17RA-HKH-Tb at 5 nM

Compounds were serially diluted in DMSO before receiving an aqueous dilution into a 384 well dilution plate (Greiner #781281), to give a 25% DMSO solution.

IL-17A (10 μL) was added to a black low volume assay plate (Costar #4511) and diluted compound (5 μL) was transferred from the aqueous dilution plate. The cytokine and compound were allowed to incubate for 1 h, then IL-17RA (10 μL) was added. The plates were wrapped in foil and incubated at room temperature for 18-20 h with gentle shaking (<400 rpm) before being read on a Perkin Elmer Envision plate reader (Excitation: 330 nm; Emission 615/645 nm).

The final assay concentrations were IL-17A-AF647 2 nM and IL-17RA-Tb 2 nM, 5% DMSO.

When tested in the IL-17 FRET assay, the compounds of the accompanying Examples were all found to exhibit $IC_{50}$ values of 10 μM or better.

When tested in the IL-17 FRET assay, compounds of the accompanying Examples exhibit $IC_{50}$ values generally in the range of about 0.01 nM to about 10 μM, usually in the range of about 0.01 nM to about 5 μM, typically in the range of about 0.01 nM to about 1 μM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

Inhibition of IL-17A Induced IL-6 Release from Dermal Fibroblast Cell Line

The purpose of this assay is to test the neutralising ability to IL-17 proteins, in a human primary cell system. Stimulation of normal human dermal fibroblasts (HDF) with IL-17 alone produces only a very weak signal but in combination with certain other cytokines, such as TNFα, a synergistic effect can be seen in the production of inflammatory cytokines, i.e. IL-6.

HDFs were stimulated with IL-17A (50 pM) in combination with TNF-α (25 pM). The resultant IL-6 response was then measured using a homogenous time-resolved FRET kit from Cisbio. The kit utilises two monoclonal antibodies, one labelled with Eu-Cryptate (Donor) and the second with d2 or XL665 (Acceptor). The intensity of the signal is proportional to the concentration of IL-6 present in the sample (Ratio is calculated by 665/620×104).

The ability of a compound to inhibit IL-17 induced IL-6 release from human dermal fibroblasts is measured in this assay.

HDF cells (Sigma #106-05n) were cultured in complete media (DMEM+10% FCS+2 mM L-glutamine) and maintained in a tissue culture flask using standard techniques. Cells were harvested from the tissue culture flask on the morning of the assay using TrypLE (Invitrogen #12605036). The TrypLE was neutralised using complete medium (45 mL) and the cells were centrifuged at 300×g for 3 minutes. The cells were re-suspended in complete media (5 mL) counted and adjusted to a concentration of $3.125\times10^4$ cells/mL before being added to the 384 well assay plate (Corning #3701) at 40 μL per well. The cells were left for a minimum of three hours, at 37° C./5% $CO_2$, to adhere to the plate.

Compounds were serially diluted in DMSO before receiving an aqueous dilution into a 384 well dilution plate (Greiner #781281), where 5 μL from the titration plate was transferred to 45 μL of complete media and mixed to give a solution containing 10% DMSO.

Mixtures of TNFα and IL-17 cytokine were prepared in complete media to final concentrations of TNFα 25 pM/IL-17A 50 pM, then 30 μL of the solution was added to a 384 well reagent plate (Greiner #781281).

10 μL from the aqueous dilution plate was transferred to the reagent plate containing 30 μL of the diluted cytokines, to give a 2.5% DMSO solution. The compounds were incubated with the cytokine mixtures for one hour at 37° C. After the incubation, 10 μL was transferred to the assay plate, to give a 0.5% DMSO solution, then incubated for 18-20 h at 37° C./5% $CO_2$.

From the Cisbio IL-6 FRET kit (Cisbio #62IL6PEB) europium cryptate and Alexa 665 were diluted in reconstitution buffer and mixed 1:1, as per kit insert. To a white low volume 384 well plate (Greiner #784075) were added FRET reagents (10 μL), then supernatant (10 μL) was transferred from the assay plate to Greiner reagent plate. The mixture was incubated at room temperature for 3 h with gentle shaking (<400 rpm) before being read on a Synergy Neo 2 plate reader (Excitation: 330 nm; Emission: 615/645 nm).

When tested in the above assay, compounds of the accompanying Examples were found to exhibit $IC_{50}$ values of 10 μM or better.

When tested in the above assay, compounds of the accompanying Examples exhibit $IC_{50}$ values generally in the range of about 0.01 nM to about 10 usually in the range of about 0.01 nM to about 5 μM, typically in the range of about 0.01 nM to about 1 μM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

The following Examples illustrate the preparation of compounds according to the invention.

EXAMPLES

Abbreviations

- DCM: dichloromethane DMF: N,N-dimethylformamide
- MeOH: methanol THF: tetrahydrofuran
- DMSO: dimethyl sulfoxide DIPEA: N,N-diisopropylethylamine
- EtOAc: ethyl acetate TFA: trifluoroacetic acid
- EtOH: ethanol AcOH: acetic acid
- NMP: 1-methyl-2-pyrrolidinone DMA: N,N-dimethylacetamide
- TBME: tert-butyl methyl ether DBU: 1,8-diazabicyclo [5.4.0]undec-7-ene
- HATU: 1-[bis(dimethylamino)methylene]-1H-1,2,3-triazolo[4,5-b]pyridinium 3-oxid hexafluorophosphate
- XPhos: 2-dicyclohexylphosphino-2',4',6'-triisopropylbiphenyl
- BrettPhos: 2-(dicyclohexylphosphino)-3,6-dimethoxy-2',4',6'-triisopropyl-1,1'-biphenyl
- $Pd_2(dba)_3$: tris(dibenzylideneacetone)dipalladium(0)
- $Pd(dppf)Cl_2$·DCM: [1,1'-bis(diphenylphosphino)ferrocene]dichloropalladium(II), complex with dichloromethane
- BrettPhos Pd G3: [(2-dicyclohexylphosphino-3,6-dimethoxy-2',4',6'-triisopropyl-1,1'-biphenyl)-2-(2'-amino-1,1'-biphenyl)]palladium(II) methanesulfonate
- AlPhos palladium complex: bis{[2-(diadamantylphosphino)-3-methoxy-2,4,6-triisopropyl-3-(2,3,5,6-tetrafluoro-4-butylphenyl)-1,1-biphenyl]palladium(0)}1,5-cyclooctadiene
- (tBu)PhCPhos Pd G3: {[2',6'-bis(dimethylamino)-2-(tert-butyl)(phenyl)phosphino-1,1'-biphenyl]-2-(2'-amino-1,1'-biphenyl)}palladium(II) methanesulfonate
- (tBu)PhCPhos Pd G4: {[2',6'-bis(dimethylamino)-2-(tert-butyl)(phenyl)phosphino-1,1'-biphenyl]-2-(2'-methylamino-1,1'-biphenyl)}palladium(II) methanesulfonate
- h: hour r.t.: room temperature
- M: mass RT: retention time
- HPLC: High Performance Liquid Chromatography
- LCMS: Liquid Chromatography Mass Spectrometry Analytical Conditions All reactions involving air- or moisture-sensitive reagents were performed under a nitrogen atmosphere using dried solvents and glassware.

HPLC-MS was performed on an Agilent 1200-6120 LC-MS system coupled to UV Detection (230 to 400 nm and 215 nm) and Mass Spec Detection Agilent 6120 Mass Spectrometer (ES) m/z 120 to 800 (unless stated otherwise in the Methods detailed below).

Method 1

- X-Bridge C18 Waters 2.1×20 mm, 2.5 μm column
- Mobile Phase A: 5 mM ammonium formate in water+0.1% ammonia solution
- Mobile Phase B: acetonitrile+5% water+0.1% ammonia solution
- Gradient program: Flow rate 1 mL/minute

| Time | A % | B % |
|---|---|---|
| 0.00 | 96.00 | 4.00 |
| 1.50 | 5.00 | 95.00 |
| 2.25 | 5.00 | 95.00 |
| 2.50 | 96.00 | 4.00 |

Method 2

- X-Bridge C18 Waters 2.1×30 mm, 2.5 μm column
- Mobile Phase A: 5 mM ammonium formate in water+0.1% ammonia solution
- Mobile Phase B: acetonitrile+5% water+0.1% ammonia solution
- Gradient program: Flow rate 1 mL/minute

| Time | A % | B % |
|---|---|---|
| 0.00 | 95.00 | 5.00 |
| 4.00 | 5.00 | 95.00 |
| 5.00 | 5.00 | 95.00 |

Method 3

- Stationary Phase: X-Bridge C18 Waters (2.1×20 mm, 2.5 μm column)
- Column Temperature: 40° C.
- Mobile Phase A: 10 mM ammonium formate in water+0.1% formic acid
- Mobile Phase B: acetonitrile+5% water+0.1% formic acid
- Flow rate: 1 mL/minute
- Gradient program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 4

- MSQ1/MSQ2 low pH uPLC—MET-uHPLC-AB-101, 7 minute run.
- Stationary Phase: Phenomenex Kinetix-XB C18 (2.1×100 mm, 1.7 μm column)
- Column Temperature: 40° C.
- Mobile Phase A: water+0.1% formic acid
- Mobile Phase B: acetonitrile+0.1% formic acid
- Flow rate: 0.6 mL/minute Gradient Program:

| Time | A % | B % |
|---|---|---|
| 0.00 | 95.00 | 5.00 |
| 5.30 | 0.00 | 100.00 |

-continued

| Time | A % | B % |
|---|---|---|
| 5.80 | 0.00 | 100.00 |
| 5.82 | 95.00 | 5.00 |
| 7.00 | 95.0 | 5.00 |

Method 5

Stationary Phase: Phenomenex Gemini NX-C18 (2×20 mm, 3 μm column)

Mobile Phase A: 10 mM ammonium formate in water+0.1% ammonia solution

Mobile Phase B: acetonitrile+5% water+0.1% ammonia solution

Flow rate: 1 mL/minute

Gradient Program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 6

Stationary Phase: Waters Acquity UPLC BEH C18 (2.1×50 mm, 1.7 μm column)

Mobile Phase A: 10 mM ammonium formate in water+0.1% ammonia solution

Mobile Phase B: acetonitrile+5% water+0.1% ammonia solution

Flow rate: 1.5 mL/minute

Gradient Program:

| Time | A % | B % |
|---|---|---|
| 0.00 | 95.00 | 5.00 |
| 0.10 | 95.00 | 5.00 |
| 3.50 | 5.00 | 95.00 |
| 4.00 | 5.00 | 95.00 |
| 4.05 | 95.00 | 5.00 |

Method 7

Stationary Phase: Waters Acquity UPLC BEH C18 (2.1×50 mm, 1.7 μm column)

Mobile Phase A: 10 mM ammonium formate in water+0.1% formic acid

Mobile Phase B: acetonitrile+5% water+0.1% formic acid

Flow rate: 1.5 mL/minute

Gradient Program:

| Time | A % | B % |
|---|---|---|
| 0.00 | 95.00 | 5.00 |
| 0.10 | 95.00 | 5.00 |
| 3.50 | 5.00 | 95.00 |
| 4.00 | 5.00 | 95.00 |
| 4.05 | 95.00 | 5.00 |

Method 8

Stationary Phase: Phenomenex Gemini NX-C18 (2×20 mm, 3 μm column)

Mobile Phase A: 10 mM ammonium formate in water+0.1% ammonia solution

Mobile Phase B: acetonitrile+5% water+0.1% ammonia solution

Flow rate: 1 mL/minute

Gradient Program:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 9

Stationary Phase: Waters Acquity H-class UPLC C18 (2.1×50 mm, 1.8 μm column) (Acquity UPLC HSS T3)

Mobile Phase A: water/acetonitrile/formic acid (95:5:750 μL/L)

Mobile Phase B: water/acetonitrile/formic acid (5:95:500 μL/L)

Flow rate: 0.8 mL/minute

Gradient Program:

| Time | A % | B % |
|---|---|---|
| 0.00 | 98.00 | 2.00 |
| 0.30 | 98.00 | 2.00 |
| 3.00 | 5.00 | 95.00 |
| 4.00 | 5.00 | 95.00 |
| 4.10 | 98.00 | 2.00 |
| 5.10 | 98.00 | 2.00 |

Intermediate 1

3-Fluoro-4-(4,4,5,5-tetramethyl-1,3,2-dioxaborolan-2-yl)benzene-1,2-diamine

A solution of 4-bromo-3-fluorobenzene-1,2-diamine (5.0 g, 24.39 mmol), bis(pinacolato)diboron (6.5 g, 26 mmol) and potassium acetate (7.2 g, 73 mmol) in 1,4-dioxane (50 mL) was degassed with $N_2$ for 10 minutes, then Pd(dppf)$Cl_2$·DCM (1.3 g, 1.58 mmol) was added. The mixture was degassed with $N_2$ for a further 10 minutes, then the reaction mixture was heated at 105° C. overnight. The reaction mixture was cooled and filtered through Celite®, washing the plug with EtOAc. The filtrate was concentrated in vacuo, then the residue was partitioned between DCM and water. The organic layers were dried over $Na_2SO_4$ and concentrated in vacuo, then purified by flash chromatography, eluting with EtOAc/hexanes (0-65% gradient), to give the title compound (3.7 g, 60%) as a brown solid. LCMS (Method 1): $[M+H]^+$ m/z 253, RT 1.02 minutes.

Intermediate 2

Methyl 4-(3,4-diamino-2-fluorophenyl)-2,5-dihydrofuran-3-carboxylate

To a solution of methyl 4-oxotetrahydrofuran-3-carboxylate (2.0 g, 13.18 mmol), dissolved in DCM (28 mL) and cooled under $N_2$ to −78° C., was added DIPEA (15.8 mmol). The reaction mixture was stirred under $N_2$, then a 1M solution of trifluoro-methanesulfonic anhydride in DCM (14.50 mmol) was added. The reaction mixture was stirred at −78° C. for 30 minutes, then warmed to r.t. and stirred for 4 h. Saturated aqueous $NaHCO_3$ solution (30 mL) was added. The mixture was stirred rapidly at r.t. for 5 minutes, then filtered. The organic layer was concentrated in vacuo. The resulting brown oil was taken up in 1,4-dioxane (28 mL), then Intermediate 1 (2.69 g, 10.70 mmol), $K_2CO_3$ (5.54 g, 40.1 mmol) and water (90 mL) were added. The mixture was sparged with $N_2$. Pd(dppf)$Cl_2$·DCM (10.3 g, 1.34 mmol) was added, and the mixture was further sparged with $N_2$, then heated at 100° C. overnight. The mixture was cooled and concentrated in vacuo, then the residue was partitioned between DCM and water. The organic layers were separated and concentrated in vacuo. The crude residue was purified by flash chromatography, eluting with EtOAc/hexanes (0-100% gradient), yielding the title compound (1.65 g, 49%) as an orange solid. LCMS (Method 1): $[M+H]^+$ m/z 253, RT 0.80 minutes.

Intermediate 3

Methyl 4-(3,4-diamino-2-fluorophenyl)tetrahydro-furan-3-carboxylate

To a solution of Intermediate 2 (0.56 mmol) in EtOH (8 mL) was added 10% Pd/C (130 mg). The reaction mixture was stirred under an atmosphere of hydrogen for three days, then filtered through Celite® (1 g), washing with DCM. The residue was concentrated in vacuo to give the title compound (1:1 mixture of cis isomers) (quantitative) as a brown solid. LCMS (Method 1): $[M+H]^+$ m/z 255, RT 0.63 minutes.

Intermediate 4 (General Method 1)

tert-Butyl N—[(S)-(5-bromo-4-fluoro-1H-benzimidazol-2-yl)(4-methylcyclohexyl)methyl]-carbamate (Trans Isomer)

To a solution of trans-(2S)-2-(tert-butoxycarbonylamino)-2-(4-methylcyclohexyl)acetic acid (5 g, 18.42 mmol) in DCM were added 4-bromo-3-fluorobenzene-1,2-diamine (3.97 g, 19.4 mmol), HATU (8.67 g, 22.1 mmol) and DIPEA (6.4 mL, 37 mmol). The mixture was stirred at r.t. overnight, then partitioned between DCM and water. The organic layers were dried over $Na_2SO_4$, then concentrated in vacuo. The residue was taken up in AcOH (40 mL) and heated at reflux temperature overnight, then poured onto saturated aqueous $NaHCO_3$ solution and partitioned between EtOAc and water. The organic layers were washed with brine, dried over $Na_2SO_4$ and concentrated in vacuo. The crude residue was purified by flash chromatography, eluting with EtOAc/hexanes (0-50% gradient), giving the title compound (7.04 g, 87% overall). LCMS (Method 1): $[M+H]^+$ m/z 442, RT 1.52 minutes.

Intermediate 5

Methyl 4-{2-[(S)-(tert-butoxycarbonylamino)(cyclopentyl)methyl]-4-fluoro-1H-benzimidazol-5-yl}tetrahydrofuran-3-carboxylate The title compound (272 mg, 41%) was prepared from Intermediate 3 (321 mg, 1.26 mmol) and (2S)-2-(tert-butoxycarbonylamino)-2-cyclopentylacetic acid (310 mg, 1.21 mmol) in accordance with General Method 1. LCMS (Method 1): $[M+H]^+$ m/z 462, RT 1.20 minutes.

Intermediate 6 (General Method 2)

4-{2-[(S)-(tert-Butoxycarbonylamino)(cyclopentyl)methyl]-4-fluoro-1H-benzimidazol-5-yl}tetrahydrofuran-3-carboxylic Acid A solution of LiOH·$H_2O$ (20 mg, 0.84 mmol) in water (0.5 mL) was added to a solution of Intermediate 5 (318 mg, 0.69 mmol) in EtOH (2 mL). The reaction mixture was stirred at r.t. for 3.5 h, then concentrated in vacuo, to give the title compound (309 mg, quantitative). LCMS (Method 1): $[M+H]^+$ m/z 448, RT 0.89 minutes.

Intermediate 7 (General Method 3)

(4-{2-[(S)-Amino(cyclopentyl)methyl]-4-fluoro-1H-benzimidazol-5-yl}tetrahydrofuran-3-yl)(3,3-difluoroazetidin-1-yl)methanone To a solution of Intermediate 6 (309 mg, 0.69 mmol), 3,3-difluoroazetidine hydrochloride (145 mg, 1.40 mmol) and DIPEA (2.1 mmol) in DMF (2 mL) was added HATU (0.90 mmol). The reaction mixture was stirred at r.t. for 48 h, then partitioned between DCM and water. The organic phase was separated and dried, then concentrated in vacuo. The crude residue was purified by flash column chromatography (0-100% EtOAc/hexanes). The recovered material was taken up in DCM (4 mL), and 4N HCl in 1,4-dioxane (0.26 mL) was added. The reaction mixture was stirred overnight, then concentrated in vacuo. The residue was dissolved in MeOH (2 mL) and eluted onto an Isolute SCX-2 cartridge (5 g), washing through with MeOH (20 mL). The residue was treated with 7M $NH_3$ in MeOH solution (20 mL), then concentrated in vacuo, to give the title compound (234 mg, 80%). LCMS (Method 1): $[M+H]^+$ m/z 423, RT 0.93 minutes.

Intermediate 8

1-(3,3-Difluoroazetidin-1-yl)prop-2-en-1-one

A solution of 3,3-difluoroazetidine hydrochloride (6.16 g, 47.54 mmol) in DCM (50 mL) was cooled to 0° C. with an ice bath under nitrogen, then DIPEA (18 mL, 103.52 mmol) was added. The mixture was stirred for 5 minutes, then acryloyl chloride (4.2 mL, 49 mmol) was added. The mixture was stirred at 0° C. for 30 minutes, then allowed to warm to r.t. overnight. 1M HCl (50 mL) was added, and the aqueous layer was extracted with DCM (50 mL). The organic layers were washed with water (50 mL), aqueous $NaHCO_3$ solution (50 mL) and brine (50 mL), then filtered through a phase separation column and concentrated in vacuo. The residual orange solid was triturated with heptane, then dried under vacuum, to yield the title compound (5.23 g, 74.8%). $\delta_H$ (400 MHz, DMSO-$d_6$) 6.33 (dd, J 17.0, 10.2 Hz, 1H), 6.17 (dd, J 17.0, 2.1 Hz, 1H), 5.76 (dd, J 10.3, 2.1 Hz, 1H), 4.70 (t, J 12.5 Hz, 2H), 4.36 (t, J 12.7 Hz, 2H).

Intermediate 9 tert-Butyl N—[(S)-{5-[(E)-3-(3,3-difluoroazetidin-1-yl)-3-oxoprop-1-enyl]-4-fluoro-1H-benzimidazol-2-yl}(4-methylcyclohexyl)methyl] carbamate A solution of Intermediate 4 (500 mg, 1.14 mmol), Intermediate 8 (175 mg, 1.19 mmol), palladium(II) acetate (13 mg, 0.06 mmol) and tri-O-tolylphosphine (138 mg, 0.45 mmol) in a mixture of DIPEA (2 mL) and DMF (2 mL) was stirred at 110° C. for 6 h. The reaction mixture was concentrated under reduced pressure, then purified by silica gel chromatography (gradient elution with 0-80% ethyl acetate in hexanes) to give the title compound (390 mg, 67%) as a colourless solid. LCMS (Method 1): $[M+H]^+$ m/z 507, RT 1.38 minutes.

Intermediate 10 tert-Butyl N—[(S)-{5-[1-benzyl-4-(3,3-difluoroazetidine-1-carbonyl)pyrrolidin-3-yl]-4-fluoro-1H-benzimidazol-2-yl}(4-methylcyclohexyl)methyl]carbamate A solution of Intermediate 9 (250 mg, 0.49 mmol), N-(methoxymethyl)-1-phenyl-N-(trimethylsilylmethyl) methanamine (0.76 mL, 2.96 mmol) and TFA (0.037 mL, 0.05 mmol) in DCM (4 mL) was stirred at r.t. overnight. The mixture was concentrated in vacuo, then the residue was purified by silica gel chromatography (gradient elution with 20-100% EtOAc in hexanes), to give the title compound (225 mg, 72%) as a yellow foam. LCMS (Method 1): $[M+H]^+$ m/z 640, RT 1.51 minutes.

Intermediate 11

(4-{2-[(S)-Amino(4-methylcyclohexyl)methyl]-4-fluoro-1H-benzimidazol-5-yl}-1-benzylpyrrolidin-3-yl)(3,3-difluoroazetidin-1-yl)methanone TFA (1 mL) was added to a solution of Intermediate 10 (200 mg, 0.31 mmol) in DCM (4 mL). The mixture was stirred at r.t. for 3 h, then concentrated in vacuo. The residue was purified by passing through a SCX column with 7M $NH_3$ in MeOH, then the solvent was removed in vacuo, to provide the title compound (160 mg, 95%) as a colourless solid. LCMS (Method 1): $[M+H]^+$ m/z 540, RT 1.10 minutes.

Intermediate 12

Methyl (3SR,4RS)-4-(2-{(S)-(tert-butoxycarbonylamino)[4-(trifluoromethyl)cyclohexyl]-methyl}-4-fluoro-1H-benzimidazol-5-yl)tetrahydrofuran-3-carboxylate The title compound (3.49 g, 98%) was prepared from Intermediate 3 (1.75 g, 6.87 mmol) and (2S)-2-(tert-butoxycarbonylamino)-2-[4-(trifluoromethyl)cyclohexyl]acetic acid (2.13 g, 6.55 mmol) in accordance with General Method 1. LCMS (Method 1): $[M+H]^+$ m/z 544, RT 1.37 minutes.

Intermediate 13

(3SR,4RS)-4-(2-{(S)-(tert-Butoxycarbonylamino)[4-(trifluoromethyl)cyclohexyl]methyl}-4-fluoro-1H-benzimidazol-5-yl)tetrahydrofuran-3-carboxylic Acid The title compound (1.97 g, quantitative) was prepared from Intermediate 12 (2.0 g, 3.68 mmol) in accordance with General Method 2. LCMS (Method 1): $[M+H]^+$ m/z 530, RT 0.98 minutes.

Intermediate 14

[(3SR,4RS)-4-(2-{(S)-(Amino)[4-(trifluoromethyl) cyclohexyl]methyl}-4-fluoro-1H-benzimidazol-5-yl) tetrahydrofuran-3-yl](3,3-difluoroazetidin-1-yl) methanone The title compound (0.83 g, 41%) was prepared from Intermediate 13 (1.97 g, 3.68 mmol) in accordance with General Method 3. LCMS (Method 1): $[M+H]^+$ m/z 505, RT 1.16 minutes.

Intermediate 15

(2S)-2-(Benzyloxycarbonylamino)-2-(4,4-difluorocyclohexyl)acetic Acid

To a stirred solution of (2S)-2-amino-2-(4,4-difluorocyclohexyl)acetic acid hydrochloride (1.61 g, 6.66 mmol) and triethylamine (3.25 mL, 23.3 mmol) in DCM (26.6 mL) at 0° C. was added N-(benzyloxycarbonyloxy)succinimide (1.61 g, 6.33 mmol). The reaction mixture was warmed to room temperature and stirred for 4 h, then diluted with DCM (25 mL) and washed with 5% hydrochloric acid (50 mL) and water (50 mL). The organic extracts were combined, passed through a phase separator and concentrated. Trituration with hexane (50 mL) afforded the title compound (1.99 g, 91%) as a white solid. $\delta_H$ (300 MHz, DMSO-$d_6$) 12.70 (s, 1H), 7.09 (d, J 8.7 Hz, 1H), 7.43-7.26 (m, 5H), 5.04 (s, 2H), 4.00 (dd, J 8.7, 6.0 Hz, 1H), 2.12-1.55 (m, 7H), 1.52-1.19 (m, 2H).

Intermediate 16

(2S)-2-(tert-Butoxycarbonylamino)-2-(4,4-difluorocyclohexyl)acetic acid

To a stirred solution of (2S)-2-amino-2-(4,4-difluorocyclohexyl)acetic acid hydrochloride (2.0 g, 8.71 mmol) in DCM (10 mL) were added triethylamine (4.3 mL, 30.5 mmol) and N-(tert-butoxycarbonyloxy)succinimide (1.72 g, 7.83 mmol). The resulting mixture was stirred at room temperature for 24 h, then diluted with DCM (200 mL), 5% hydrochloric acid (2×100 mL) and water (100 mL). The organic extracts were combined, passed through a phase separator and concentrated. Trituration with hexane (100 mL) afforded the title compound (2.0 g, 78%) as a white solid. $\delta_H$ (300 MHz, DMSO-$d_6$) 12.60 (s, 1H), 7.09 (d, J 8.7 Hz, 1H), 3.91 (dd, J 8.5, 6.2 Hz, 1H), 2.08-1.92 (m, 2H), 1.92-1.54 (m, 5H), 1.51-1.16 (m, 11H).

Intermediate 17

Bromo(2-tert-butoxy-2-oxoethyl)zinc tert-Butyl 2-bromoacetate (45.0 mL, 0.31 mol) was added dropwise over 1 h to a slurry of activated zinc (30.2 g, 0.46 mol) in THF (400 mL) at 60° C. An exotherm was observed. The reaction mixture was stirred at 65° C. for 1 h, then allowed to cool to r.t., with settling of the excess zinc. Conversion was assumed to be 100%, and the resulting yellow solution was assumed to be a 0.77M solution in THF.

Intermediate 18

N,N-Dibenzyl-3-bromo-2-fluoro-6-nitroaniline

To a stirred suspension of 1-bromo-2,3-difluoro-4-nitrobenzene (23.0 g, 96.6 mmol) and potassium carbonate (16.0 g, 116 mmol) in acetonitrile (250 mL) was added N-benzyl-1-phenylmethanamine (20.0 mL, 106 mmol). The suspension was stirred at 80° C. for 16 h, then re-treated with N-benzyl-1-phenylmethanamine (2.0 mL, 10.4 mmol) and stirred at 80° C. for 1 h. The mixture was filtered, then concentrated. The residue was purified by flash column chromatography, eluting with a gradient of ethyl acetate in heptanes, to afford the title compound (40.9 g, 85%) as an orange solid. $\delta_H$ 400 MHz, DMSO-$d_6$) 7.64 (dd, J 8.8, 6.5 Hz, 1H), 7.54 (dd, J 8.8, 1.6 Hz, 1H), 7.33-7.18 (m, 10H), 4.15 (s, 4H). LCMS (Method 3): $[M+H]^+$ m/z 415, 417, RT 2.25 minutes.

Intermediate 19 tert-Butyl 2-[3-(dibenzylamino)-2-fluoro-4-nitrophenyl]acetate

To a stirred solution of Intermediate 18 (63.0 g, 0.15 mol), XPhos (4.17 g, 8.74 mmol) and allyl(chloro)palladium dimer (1.61 g, 4.37 mmol) in THF (400 mL) under nitrogen was added Intermediate 17 (0.77M, 378 mL, 0.29 mol) dropwise. The mixture was stirred at 50° C. for 45 minutes, then cooled to 30° C. and quenched with saturated aqueous $NH_4Cl$ solution (200 mL), keeping the temperature between 20° C. and 30° C. The combined mixture was diluted with EtOAc (200 mL), and the phases were separated. The aqueous phase was extracted with EtOAc (50 mL). The organic fractions were combined, dried over $Na_2SO_4$ and concentrated in vacuo. The residue was purified by flash column chromatography, eluting with a gradient of DCM in heptanes, to afford the title compound (65 g, 94%) as a yellow powder. $\delta_H$ 400 MHz, DMSO-$d_6$) 7.47 (dd, J 8.3, 1.1 Hz, 1H), 7.30-7.18 (m, 11H), 4.11 (s, 4H), 3.68 (d, J 1.3 Hz, 2H), 1.41 (s, 9H). LCMS (Method 3): $[M+H]^+$ m/z 451, RT 2.27 minutes.

Intermediate 20 tert-Butyl 4-[3-(dibenzylamino)-2-fluoro-4-nitrophenyl]tetrahydropyran-4-carboxylate To a stirred solution of NaH (60% purity, 9.23 g, 0.23 mol) in DMA (400 mL) was added Intermediate 19 (40 g, 88.8 mmol) at 5° C. in portions. The mixture was stirred for 10 minutes, then 1-iodo-2-(2-iodoethoxy)ethane (14 mL, 0.10 mol) was added dropwise. The resulting mixture was stirred at r.t. for 16 h, then cooled in an ice bath and quenched with saturated aqueous $NH_4Cl$ solution. The mixture was extracted with TBME (2×300 mL). The organic fractions were combined and washed with saturated brine (50 mL), then dried over $Na_2SO_4$ and concentrated in vacuo. The residue was purified by flash column chromatography, eluting with a gradient of EtOAc in heptanes, to afford the title compound (37.6 g, 67%) as a yellow solid. $\delta_H$ 500 MHz, $CDCl_3$) 7.36 (dd, J 8.7, 1.4 Hz, 1H), 7.30-7.17 (m, 10H), 7.15-7.10 (m, 1H), 4.21-4.15 (m, 4H), 3.86-3.76 (m, 4H), 2.33 (d, J 13.5 Hz, 2H), 2.01-1.92 (m, 2H), 1.44 (s, 9H). LCMS (Method 3): $[M+H]^+$ m/z 521, RT 2.26 minutes.

Intermediate 21 tert-Butyl 4-[4-amino-3-(dibenzylamino)-2-fluorophenyl]tetrahydropyran-4-carboxylate Intermediate 20 (36.9 g, 65.9 mmol) was dissolved in EtOH (700 mL) and EtOAc (300 mL), and 10% Pd/C (50% wet, 21.1 g, 9.89 mmol) was added. The reaction mixture was purged and stirred vigorously under a hydrogen atmosphere at r.t. for 20 h. The reaction mixture was filtered through a pad of Celite®, then washed with EtOH (2×100 mL) and concentrated in vacuo. The residue was purified by flash column chromatography, eluting with a gradient of EtOAc in heptanes, to afford the title compound (21.6 g, 67%) as an off-white solid. $\delta_H$ 400 MHz, DMSO-$d_6$) 7.28-7.16 (m, 10H), 6.78 (t, J 8.6 Hz, 1H), 6.32 (d, J 8.5 Hz, 1H), 5.03 (s, 2H), 4.11-3.90 (m, 4H), 3.70-3.49 (m, 4H), 2.15-2.05 (m, 2H), 1.86-1.75 (m, 2H), 1.33 (s, 9H). LCMS (Method 3): $[M+H]^+$ m/z 491, RT 2.19 minutes.

Intermediate 22 tert-Butyl 4-(3,4-diamino-2-fluorophenyl)tetrahydropyran-4-carboxylate

Intermediate 21 (21.6 g, 44.0 mmol) was dissolved in EtOH (300 mL) and 10% Pd/C (50% wet, 9.37 g, 4.40 mmol) was added. The reaction mixture was purged and stirred vigorously under a hydrogen atmosphere at r.t. for 16 h. The reaction mixture was filtered through a pad of Celite®, then washed with EtOH (2×100 mL) and concentrated in vacuo, to give the title compound (12.93 g, 90%) as a pale pink powder. $\delta_H$ 400 MHz, DMSO-$d_6$) 6.38-6.27 (m, 2H), 4.59 (s, 4H), 3.71 (dt, J 11.5, 3.9 Hz, 2H), 3.59-3.48 (m, 2H), 2.23-2.11 (m, 2H), 1.92-1.78 (m, 2H), 1.35 (s, 9H). LCMS (Method 3): $[M-{}^tBu+H]^+$ m/z 255, RT 1.63 minutes.

Intermediate 23 tert-Butyl 4-(3-amino-4-{[(2S)-2-(benzyloxycarbonylamino)-2-(4,4-difluorocyclohexyl)-acetyl]amino}-2-fluorophenyl)tetrahydropyran-4-carboxylate HATU (6.89 g, 18.1 mmol) was added portionwise to a stirred solution of Intermediate 15 (5.19 g, 15.8 mmol), Intermediate 22 (4.93 g, 15.1 mmol) and DIPEA (5.3 mL, 30.2 mmol) in DCM (50 mL) at r.t. The reaction mixture was stirred for 2 h, then washed with water (25 mL). The aqueous layer was extracted with DCM (15 mL). The organic layers were combined, passed through a phase separator and evaporated in vacuo. The residue was purified by flash column chromatography, eluting with a gradient of EtOAc in heptanes, to afford the title compound (9.5 g, 91%) as a pale pink solid. $\delta_H$ (500 MHz, DMSO-$d_6$) 9.49 (s, 1H), 7.68 (d, J 8.1 Hz, 1H), 7.39-7.29 (m, 5H), 7.07 (d, J 8.5 Hz, 1H), 6.57 (t, J 8.4 Hz, 1H), 5.05 (s, 2H), 4.84 (s, 2H), 4.14 (t, J 8.0 Hz, 1H), 3.77-3.69 (m, 2H), 3.64-3.56 (m, 2H), 2.20 (d, J 13.5 Hz, 2H), 2.10-1.99 (m, 2H), 1.97-1.67 (m, 7H), 1.46-1.30 (m, 11H). LCMS (Method 3): $[M+H]^+$ m/z 620, RT 2.03 minutes.

Intermediate 24 tert-Butyl 4-{2-[(S)-benzyloxycarbonylamino(4,4-difluorocyclohexyl)methyl]-4-fluoro-1H-benzimidazol-5-yl}tetrahydropyran-4-carboxylate Intermediate 23 (17.08 g, 27.6 mmol) was stirred in acetic acid (170 mL) at 75° C. for 4 h, then the mixture was cooled to r.t. and concentrated in vacuo. The resulting gum was partitioned between saturated aqueous $NaHCO_3$ solution (150 mL) and EtOAc (200 mL). The phases were separated, and the aqueous layer was further extracted with EtOAc (200 mL). The organic fractions were combined, washed with saturated brine (50 mL) and concentrated in vacuo. The residue was suspended in 1:1 EtOAc:heptanes, filtered and washed with heptanes. The filtrate was concentrated in vacuo and purified by flash column chromatography, eluting with a gradient of EtOAc in heptanes, to afford the title compound (13.29 g, 80%) as a white powder. $\delta_H$ 400 MHz, DMSO-$d_6$) 12.79 (s, 1H), 7.96 (d, J 8.3 Hz, 1H), 7.44-7.24 (m, 5H), 7.23-7.14 (m, 1H), 5.10-4.97 (m, 2H), 4.72 (t, J 8.2 Hz, 1H), 3.82-3.72 (m, 2H), 3.61 (t, J 10.2 Hz, 2H), 2.32 (d, J 12.4 Hz, 2H), 2.16-1.64 (m, 8H), 1.54-1.42 (m, 1H), 1.36 (s, 10H), 1.27-1.21 (m, 1H). LCMS (Method 4): $[M+H]^+$ m/z 602.3, RT 3.82 minutes.

Intermediate 25

Benzyl N-[(S)-{5-[4-(3,3-difluoroazetidine-1-carbonyl)tetrahydropyran-4-yl]-4-fluoro-1H-benzimidazol-2-yl}(4,4-difluorocyclohexyl)methyl]carbamate TFA (17.0 mL, 225 mmol) was added to a solution of Intermediate 24 (9.04 g, 15.0 mmol) in DCM (75 mL). The reaction mixture was stirred at r.t. for 16 h, then concentrated in vacuo. The resultant oil was re-dissolved in TBME (75 mL) and washed with water (3×50 mL). The organic layer was passed through a phase separator and concentrated in vacuo. To a solution of the resulting off-white foam, 3,3-difluoroazetidine hydrochloride (2.34 g, 18.1 mmol) and DIPEA (15.7 mL, 90.3 mmol) in DCM (75 mL) was added HATU (7.08 g, 18.1 mmol). The reaction mixture was stirred at r.t. for 1.5 h, then washed with saturated aqueous $NH_4Cl$ solution (2×75 mL). The combined aqueous layers were extracted with DCM (2×30 mL). The organic layers were combined, passed through a phase separator and concentrated in vacuo. The residue was purified by flash column chromatography, eluting with a gradient of 0-100% EtOAc in hexanes, to give the title compound (7.23 g, 77%) as a white foam. LCMS (Method 5): $[M+H]^+$ m/z 621.0, RT 1.24 minutes.

Intermediate 26

(4-{2-[(S)-Amino(4,4-difluorocyclohexyl)methyl]-4-fluoro-1H-benzimidazol-5-yl}-tetrahydropyran-4-yl)(3,3-difluoroazetidin-1-yl)methanone Palladium on carbon (1.24 g, 1.17 mmol, 10 mass %) was added to a solution of Intermediate 25 (7.23 g, 11.7 mmol) in EtOH (117 mL) under nitrogen. The reaction flask was placed under vacuum, then backfilled with hydrogen from a balloon (3 cycles). The reaction mixture was stirred at r.t. for 7 h, then filtered through a pad of Celite®, washed through with EtOH (2×40 mL) and concentrated in vacuo, to give the crude title compound (5.32 g, 94%) as a white foam, which was utilised without further purification. LCMS (Method 5): $[M+H]^+$ m/z 487.0, RT 0.94 minutes.

Intermediate 27 tert-Butyl 4-{2-[(S)-amino(4,4-difluorocyclohexyl)methyl]-4-fluoro-1H-benzimidazol-5-yl}tetrahydropyran-4-carboxylate Palladium on carbon (300 mg, 0.282 mmol, 10 mass %) was added to a solution of Intermediate 24 (1.69 g, 2.81 mmol) in EtOH (28 mL). The reaction flask was placed under vacuum, then backfilled with hydrogen from a balloon (3 cycles). The reaction mixture was stirred at r.t. for 7 h, then filtered through a pad of Celite®/$SiO_2$ (1:1), washed through with EtOH/EtOAc (1:1, 60 mL) and concentrated in vacuo. The residue was purified by flash column chromatography, eluting with a gradient of 0-100% EtOAc in hexanes, and 0-30% MeOH in EtOAc, to give the title compound (0.99 g, 76%) as an off-white solid. LCMS (Method 5): $[M+H]^+$ m/z 468.0, RT 1.23 minutes.

Intermediate 28 tert-Butyl 4-{2-[(S)-(4,4-difluorocyclohexyl){[6-(difluoromethyl)pyridazin-3-yl]amino}-methyl]-4-fluoro-1H-benzimidazol-5-yl}tetrahydropyran-4-carboxylate DIPEA (41 μL, 0.24 mmol) was added to a solution of Intermediate 27 (31.0 mg, 0.07 mmol) and 3-chloro-6-(difluoromethyl)pyridazine (23.0 mg, 0.13 mmol) in 1,4-dioxane (0.5 mL). The reaction mixture was sealed and heated at 140° C. for 3 days, then concentrated in vacuo, re-dissolved in DCM (5 mL) and washed with water (5 mL). The aqueous layer was re-extracted with DCM (2×5 mL). The combined organic layers were dried with $Na_2SO_4$, then filtered and concentrated in vacuo. The crude residue was purified by flash column chromatography, eluting with a gradient of 0-100% EtOAc in hexanes, and 0-40% MeOH in EtOAc, to give the title compound (10.0 mg, 25%) as a pale yellow glass. LCMS (Method 5): $[M+H]^+$ m/z 596.0, RT 1.38 minutes.

Intermediate 29 tert-Butyl 4-{2-[(S)-(4,4-difluorocyclohexyl)(pyrazin-2-ylamino)methyl]-4-fluoro-1H-benzimidazol-5-yl}tetrahydropyran-4-carboxylate Sodium tert-butoxide (45 mg, 0.47 mmol) was added to a solution of Intermediate 27 (25.0 mg, 0.0535 mmol) in 1,4-dioxane (2.2 mL) under nitrogen. The mixture was stirred for 5 minutes, then 2-bromopyrazine (13 μL, 0.14 mmol) was added. The reaction vessel was placed under vacuum and backfilled with nitrogen (3 cycles), then BrettPhos Pd G3 (9 mg, 0.009 mmol) and BrettPhos (12 mg, 0.022 mmol) were added. The reaction vessel was again placed under vacuum and backfilled with nitrogen (1 cycle), then stirred at 110° C. overnight. In a separate flask, sodium tert-butoxide (45 mg, 0.47 mmol) was added to a solution of Intermediate 27 (25.0 mg, 0.0535 mmol) in 1,4-dioxane (2.2 mL) under nitrogen. The mixture was stirred for 5 minutes, then 2-bromopyrazine (24 μL, 0.25 mmol) was added. The reaction vessel was placed under vacuum and backfilled with nitrogen (3 cycles), then BrettPhos Pd G3 (9 mg, 0.009 mmol) and BrettPhos (12 mg, 0.022 mmol) were added. The reaction vessel was again placed under vacuum and backfilled with nitrogen (1 cycle), then stirred at 110° C. overnight. Both mixtures were combined, diluted with DCM (10 mL) and washed with water (10 mL). The organic layer was passed through a phase separator and concentrated in vacuo. The crude residue was purified by flash column chromatography, eluting with a gradient of 0-100% EtOAc in hexanes, and 0-20% MeOH in EtOAc, to give the title compound (31.0 mg, 53%) as a colourless glass. LCMS (Method 5): $[M+H]^+$ m/z 546.0, RT 1.31 minutes.

Intermediate 30

Mixture of Benzyl N—[(S)-{5-[4-(3,3-difluoroazetidine-1-carbonyl)tetrahydropyran-4-yl]-4-fluoro-1-(2-trimethylsilylethoxymethyl)benzimidazol-2-yl}(4,4-difluorocyclohexyl)-methyl]carbamate and benzyl N—[(S)-{6-[4-(3,3-difluoroazetidine-1-carbonyl) tetrahydro-pyran-4-yl]-7-fluoro-1-(2-trimethylsilylethoxymethyl)benzimidazol-2-yl}(4,4-difluorocyclohexyl)methyl]carbamate 2-(Trimethylsilyl)ethoxymethyl chloride (0.24 mL, 1.3 mmol) was added dropwise to a stirred solution of Intermediate 25 (720 mg, 1.16 mmol) and DIPEA (0.71 mL, 4.1 mmol) in DCM (6 mL) under nitrogen at 0° C. The reaction mixture was stirred for 16.5 h, whilst being allowed to warm slowly to r.t. Additional 2-(trimethylsilyl)-ethoxymethyl chloride (0.06 mL, 0.3 mmol) was added. The reaction mixture was stirred for a further 3 days at r.t., then diluted with DCM (20 mL) and washed with saturated aqueous $NaHCO_3$ solution (20 mL). The aqueous layer was extracted with DCM (20 mL). The combined organic layers were dried with $Na_2SO_4$, then filtered and concentrated in vacuo. The residue was purified by flash column chromatography, eluting with a gradient of 0-100% EtOAc in hexanes, to give the title compounds (mixture of SEM-regioisomers) (649 mg, 75%) as a white foam. LCMS (Method 5): $[M+H]^+$ m/z 751.0, RT 1.63 minutes (isomers unresolved).

Intermediate 31

Mixture of (4-{2-[(S)-amino(4,4-difluorocyclohexyl)methyl]-4-fluoro-1-(2-trimethylsilyl-ethoxymethyl)benzimidazol-5-yl}tetrahydropyran-4-yl)(3,3-difluoroazetidin-1-yl)-methanone and (4-{2-[(S)-amino-(4,4-difluorocyclohexyl)methyl]-4-fluoro-3-(2-trimethylsilylethoxymethyl)benzimidazol-5-yl}tetrahydropyran-4-yl)(3,3-difluoro-azetidin-1-yl) methanone Palladium on carbon (50 mg, 0.047 mmol, 10 mass %) was added to a solution of Intermediate 30 (649 mg, 0.864 mmol) in EtOH (10 mL) under nitrogen. The reaction flask was placed under vacuum, then backfilled with hydrogen from a balloon (3 cycles). The reaction mixture was stirred at r.t. for 2.5 h, then diluted with EtOAc (10 mL), filtered through a pad of Celite®/$SiO_2$ (1:1), washed through with EtOH/EtOAc (1:2, 3×25 mL) and concentrated in vacuo, to give the title compounds (mixture of SEM-regioisomers) (530 mg, 99%) as dark brown gum, which was utilised without further purification. LCMS (Method 5): $[M+H]^+$ m/z 617.0, RT 1.41 minutes.

Intermediate 32 tert-Butyl 2-[3-(dibenzylamino)-2-fluoro-4-nitrophenyl]propanoate

A mixture of Intermediate 18 (7.00 g, 16.2 mmol), XPhos (2.31 g, 4.85 mmol) and $Pd_2(dba)_3$ (2.22 g, 2.43 mmol) in dry THF (150 mL) was degassed under nitrogen for 2 minutes at r.t. A solution of bromo(2-tert-butoxy-1-methyl-2-oxoethyl)zinc in THF (0.5M, 97 mL, 48.5 mmol) was added. The reaction mixture was stirred at 50° C. for 1 h, then cooled to r.t., quenched with saturated aqueous ammonium chloride solution (30 mL) and extracted with EtOAc (3×30 mL). The organic fractions were combined, dried over sodium sulfate and concentrated. The residue was purified by flash column chromatography, eluting with a gradient of 0-10% EtOAc in heptanes, followed by acidic reverse phase column chromatography, eluting with a gradient of 70-85% acetonitrile in water (with 0.1% formic acid), to afford the title compound (7.24 g, 96%) as an orange oil. $\delta_H$ 500 MHz, $CDCl_3$) 7.31 (dd, J 8.5, 1.5 Hz, 1H), 7.28-7.25 (m, 8H), 7.25-7.20 (m, 2H), 7.07 (dd, J 8.5, 6.7 Hz, 1H), 4.22-4.17 (m, 4H), 3.89 (q, J 7.2 Hz, 1H), 1.45-1.39 (m, 12H). LCMS (Method 3): $[M+H]^+$ m/z 465, RT 2.32 minutes.

Intermediate 33

2-[3-(Dibenzylamino)-2-fluoro-4-nitrophenyl]-1-(3,3-difluoroazetidin-1-yl)propan-1-one Intermediate 32 (7.20 g, 15.5 mmol) was stirred in DCM (30 mL) and TFA (30 mL) for 18 h. The reaction mixture was concentrated in vacuo. The resulting brown oil was taken up in DCM (100 mL). 3,3-Difluoroazetidine hydrochloride (2.40 g, 18.6 mmol), DIPEA (11 mL, 61.9 mmol) and HATU (7.06 g, 18.6 mmol) were added. The reaction mixture was stirred for 2 h, then washed with water (2×50 mL) and brine (30 mL), dried over $Na_2SO_4$ and concentrated in vacuo. The residue was purified by flash column chromatography, eluting with a gradient of 0-40% EtOAc in heptanes, to afford the title compound (7.7 g, 99%) as an orange oil. $\delta_H$ 400 MHz, DMSO-$d_6$) 7.52 (dd, J 8.5, 1.2 Hz, 1H), 7.31-7.13 (m, 11H), 4.65 (q, J 11.8 Hz, 1H), 4.38-4.20 (m, 2H), 4.17 (s, 4H), 3.96 (q, J 6.9 Hz, 1H), 3.74 (q, J 11.4 Hz, 1H), 1.25 (d, J 7.0 Hz, 3H). LCMS (Method 3): $[M+H]^+$ m/z 484.0, RT 2.11 minutes.

Intermediate 34

2-(3,4-Diamino-2-fluorophenyl)-1-(3,3-difluoroazetidin-1-yl)propan-1-one

Intermediate 33 (7.7 g, 15.29 mmol) was dissolved in EtOH (100 mL) and 10% Pd/C (50% wet, 1.63 g, 0.80 mmol) was added. The reaction mixture was purged and stirred vigorously under a hydrogen atmosphere at r.t. for 16 h. The reaction mixture was filtered through a pad of Celite®, then washed with EtOH (2×100 mL) and concentrated in vacuo, to give the title compound (3.82 g, 88%) as a purple solid. $\delta_H$ 400 MHz, DMSO-$d_6$) 6.36-6.15 (m, 2H), 4.77-4.59 (m, 3H), 4.38 (s, 2H), 4.36-4.13 (m, 2H), 4.05-3.91 (m, 1H), 3.76 (q, J 6.9 Hz, 1H), 1.22 (d, J 7.0 Hz, 3H). LCMS (Method 3): $[M+H]^+$ m/z 274.0, RT 0.93 minutes.

Intermediate 35 tert-Butyl N—[(S)-{5-[2-(3,3-difluoroazetidin-1-yl)-1-methyl-2-oxoethyl]-4-fluoro-1H-benzimidazol-2-yl}(4,4-difluorocyclohexyl)methyl]carbamate To a solution of Intermediate 34 (2.32 g, 7.90 mmol) and Intermediate 16 (2.66 g, 9.06 mmol) in DCM (50 mL) was added DIPEA (2.9 mL, 16.5 mmol), followed by HATU (3.44 g, 9.06 mmol). The mixture was stirred at r.t. for 45 minutes, then diluted with DCM (50 mL) and washed with water (2×50 mL). The combined organic fractions were dried over $Na_2SO_4$ and concentrated in vacuo. The residue was purified by flash column chromatography, eluting with a gradient of 0-100% EtOAc in heptanes. The resulting pink solid was stirred in acetic acid (50 mL, 0.873 mol) at 60° C. for 9 h. The reaction mixture was concentrated in vacuo. The residue was diluted with EtOAc (100 mL) and washed with saturated aqueous $NaHCO_3$ solution (3×50 mL) and brine (30 mL), then dried over $Na_2SO_4$ and concentrated in vacuo. The residue was purified by flash column chromatography, eluting with a gradient of 0-90% EtOAc in heptanes, followed by further purification by flash column chromatography (KP-NH), eluting with a gradient of 0-100% EtOAc in heptanes, to afford the title compound (3.3 g, 78%) as a white solid. $\delta_H$ (400 MHz, DMSO-$d_6$) 12.95-12.27 (m, 1H), 7.46-7.17 (m, 2H), 7.17-6.88 (m, 1H), 4.89-4.71 (m, 1H), 4.71-4.49 (m, 1H), 4.41-3.90 (m, 4H), 2.14-1.91 (m, 3H), 1.91-1.63 (m, 3H), 1.56-1.09 (m, 15H). LCMS (Method 3): $[M+H]^+$ m/z 531.1, RT 1.86 minutes.

Intermediate 36

2-{2-[(S)-Amino(4,4-difluorocyclohexyl)methyl]-4-fluoro-1H-benzimidazol-5-yl}-difluoroazetidin-1-yl) propan-1-one Intermediate 35 (3.30 g, 5.60 mmol) was stirred in DCM (30 mL) and TFA (10 mL) at r.t. for 1 h. The reaction mixture was concentrated in vacuo. The residue was dissolved in DCM (150 mL) and washed carefully with saturated aqueous $NaHCO_3$ solution (3×50 mL). The aqueous layer was extracted with DCM (2×50 mL). The combined organic layers were dried over $Na_2SO_4$, and concentrated in vacuo, to afford the title compound (2.6 g, 97%) as a white solid. $\delta_H$ 400 MHz, DMSO-$d_6$) 7.27 (d, J 8.3 Hz, 1H), 7.11-6.95 (m, 1H), 4.77 (q, J 11.9 Hz, 1H), 4.32 (q, J 13.0, 12.3 Hz, 1H), 4.21 (q, J 12.7 Hz, 1H), 4.10 (q, J 6.9 Hz, 1H), 4.07-3.91 (m, 1H), 3.87 (d, J 5.9 Hz, 1H), 2.08-1.91 (m, 2H), 1.91-1.63 (m, 4H), 1.57-1.45 (m, 1H), 1.42-1.21 (m, 5H). LCMS (Method 3): $[M+H]^+$ m/z 431.5, RT 0.84 minutes.

Example 1

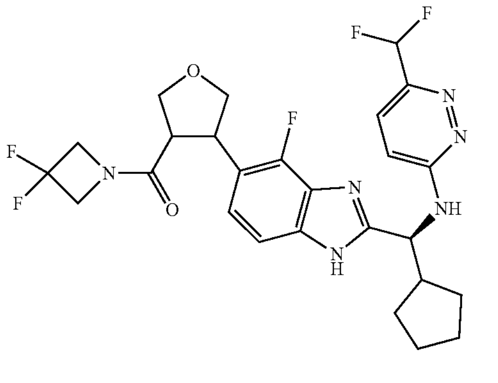 [SMILES: O=C(C1COCC1c1ccc2[nH]c([C@@H](Nc3ccc(C(F)F)nn3)C3CCCC3)nc2c1F)N1CC(F)(F)C1]

(4-{2-[(S)-(Cyclopentyl){[6-(difluoromethyl) pyridazin-3-yl]amino}methyl]-4-fluoro-1H-benzimidazol-5-yl}tetrahydrofuran-3-yl)(3,3-difluoroazetidin-1-yl)methanone A microwave vial was charged with Intermediate 7 (116 mg, 0.28 mmol), 3-chloro-6-(difluoromethyl)pyridazine (85 mg, 0.49 mmol), DIPEA (0.11 mL, 0.63 mmol) and 1,4-dioxane (2 mL), then sealed under $N_2$ and heated at 110° C. for 8 h under microwave irradiation. Heating was repeated in 8 h cycles for 3 days, then the solvents were removed in vacuo. The residue was purified using flash chromatography, eluting with EtOAc/hexanes (0-100% gradient), then preparative HPLC, to yield the title compound (3 mg, 1.9%) as a white solid. $\delta_H$ 400 MHz, DMSO-$d_6$) 7.53 (d, J 9.4 Hz, 1H), 7.32 (d, J 8.5 Hz, 1H), 7.22 (dd, J 8.4, 6.4 Hz, 1H), 7.14 (dd, J 9.3, 1.1 Hz, 1H), 6.67 (td, J 54.9, 3.1 Hz, 1H), 5.14 (dd, J 9.3, 2.5 Hz, 1H), 4.51-4.38 (m, 3H), 4.23 (qd, J 8.0, 1.6 Hz, 3H), 4.07-3.98 (m, 2H), 3.92 (td, J 8.0, 2.6 Hz, 1H), 3.83 (dd, J 19.6, 11.3 Hz, 1H), 2.67-2.59 (m, 1H), 2.07-1.99 (m, 1H), 1.79-1.50 (m, 6H), 1.42 (q, J 4.3 Hz, 1H). LCMS (Method 2): $[M+H]^+$ m/z 551, RT 1.56 minutes.

Example 2

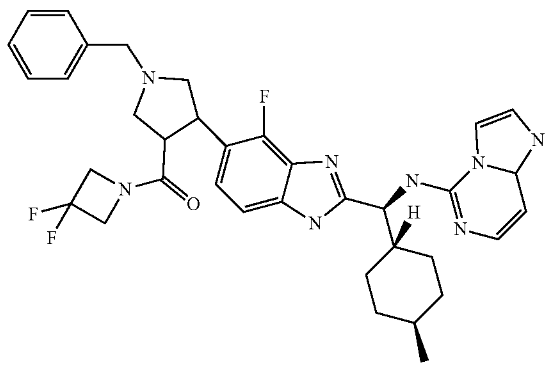 [SMILES: C[C@H]1CC[C@H]([C@H](NC2=NC=CC3NC=CN23)c2nc3c(F)c(C4CN(Cc5ccccc5)CC4C(=O)N4CC(F)(F)C4)ccc3[nH]2)CC1]

(1-Benzyl-4-{4-fluoro-2-[(S)-(imidazo[1,2-c]pyrimidin-5-ylamino)(4-methylcyclohexyl)-methyl]-1H-benzimidazol-5-yl}pyrrolidin-3-yl)(3,3-difluoroazetidin-1-yl)methanone A solution of Intermediate 11 (55 mg, 0.10 mmol), 5-chloroimidazo[1,2-c]-pyrimidine (20 mg, 0.13 mmol) and DIPEA (0.05 mL, 0.3 mmol) in NMP (2 mL, 20.76 mmol) was stirred at 80° C. overnight. After removal of solvent, the residue was purified by silica gel chromatography (gradient elution with 10-20% MeOH in EtOAc) to yield the title compound (12 mg, 18%) as a colourless solid. $\delta_H$ 400 MHz, DMSO-$d_6$) 12.73 (s, 1H), 8.32 (s, 1H), 8.17 (d, J 7.7 Hz, 1H), 7.53 (d, J 1.4 Hz, 1H), 7.51-7.47 (m, 1H), 7.38-7.20 (m, 6H), 6.61 (d, J 6.3 Hz, 1H), 5.31-5.21 (m, 1H), 4.46-4.02 (m, 3H), 3.73-3.58 (m, 2H), 3.30 (t, J 7.0 Hz, 1H), 3.14-2.86 (m, 2H), 2.73-2.63 (m, 4H), 2.23-2.00 (m, 4H), 1.94-1.86 (m, 1H), 1.74-1.59 (m, 2H), 1.38-1.04 (m, 3H), 0.98-0.78 (m, 4H). LCMS (Method 2): $[M+H]^+$ m/z 657.2, RT 1.19 minutes.

Example 3

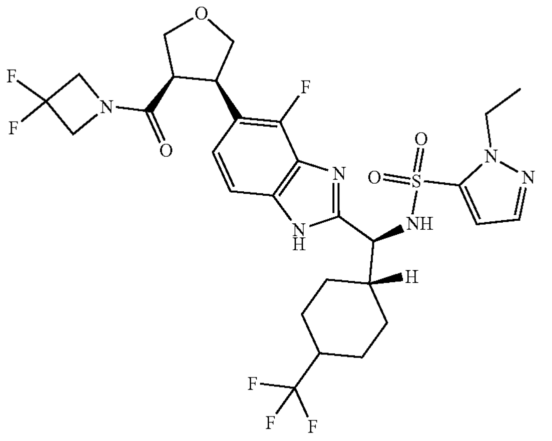

N—[(S)-{5-[(3SR,4RS)-4-(3,3-Difluoroazetidine-1-carbonyl)tetrahydrofuran-3-yl]-4-fluoro-1H-benzimidazol-2-yl}[4-(trifluoromethyl)cyclohexyl]methyl]-2-ethyl-2H-pyrazole-3-sulfonamide To a solution of Intermediate 14 (23 mg, 0.04 mmol) in pyridine (0.5 mL) was added 1-ethyl-1H-pyrazole-5-sulfonyl chloride (7.1 mg, 0.035 mmol). The reaction mixture was stirred overnight, then another aliquot of 1-ethyl-1H-pyrazole-5-sulfonyl chloride (7.1 mg, 0.035 mmol) was added. After a further 2 h, the reaction mixture was concentrated in vacuo, then the residue was purified by reverse-phase HPLC, to provide the title compound (5.3 mg, 22.7%). LCMS (Method 2): $[M+H]^+$ m/z 663.2, RT 2.44 minutes.

Example 4

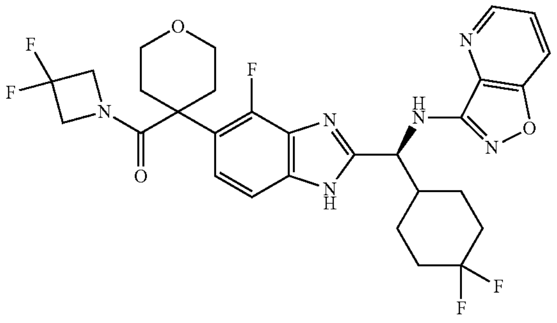 [SMILES: O=C(N1CC(F)(F)C1)C1(c2ccc3[nH]c([C@@H](Nc4noc5cccnc45)C4CCC(F)(F)CC4)nc3c2F)CCOCC1]

(3,3-Difluoroazetidin-1-yl)(4-{2-[(S)-(4,4-difluorocyclohexyl)(isoxazolo[4,5-b]pyridin-3-ylamino)methyl]-4-fluoro-1H-benzimidazol-5-yl}tetrahydropyran-4-yl)methanone Intermediate 26 (50.0 mg, 0.103 mmol), 3-chloroisoxazolo[4,5-b]pyridine (32.8 mg, 0.206 mmol) and AlPhos palladium complex (15.0 mg, 0.00769 mmol) were added to a vial, and the lid was sealed. The vial was placed under vacuum, then under nitrogen (3 cycles). TBME (0.21 mL) was added, followed by DBU (0.047 mL, 0.31 mmol), then the nitrogen line was removed. The reaction mixture was stirred at 60° C. for 18 h, then at 70° C. for a further 3 days. The reaction mixture was diluted with DCM (10 mL) and washed with water (10 mL). The aqueous layer was extracted with DCM (2×10 mL). The combined organic layers were passed through a phase separator and concentrated in vacuo. The residue was purified by preparative basic reverse-phase HPLC and freeze-dried to give the title compound (3.9 mg, 6%) as a white solid. $\delta_H$ 400 MHz, DMSO-$d_6$) 8.62 (dd, J 4.5, 1.2 Hz, 1H), 8.01 (dd, J 8.5, 1.2 Hz, 1H), 7.61 (dd, J 8.5, 4.5 Hz, 1H), 7.18 (d, J 8.3 Hz, 1H), 6.86 (br s, 1H), 4.86 (t, J 6.4 Hz, 1H), 4.21 (br s, 2H), 3.81-3.63 (m, 6H), 2.32-2.20 (m, 3H), 2.11-1.91 (m, 4H), 1.88-1.47 (m, 4H), 1.36-1.18 (m, 2H). Benzimidazole and aniline NH signals not reported. LCMS (Method 6): $[M+H]^+$ m/z 605.4, RT 1.61 minutes.

Example 5

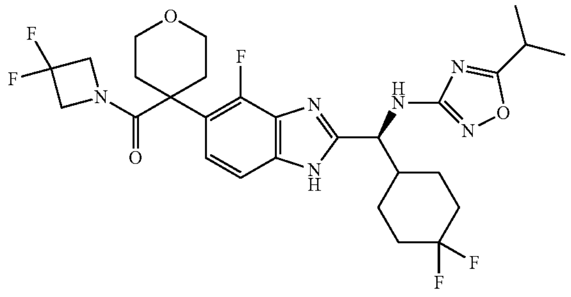 [SMILES: CC(C)c1nc(N[C@H](c2nc3c(F)c(C4(C(=O)N5CC(F)(F)C5)CCOCC4)ccc3[nH]2)C2CCC(F)(F)CC2)no1]

(3,3-Difluoroazetidin-1-yl)[4-(2-{(S)-(4,4-difluorocyclohexyl)[(5-isopropyl-1,2,4-oxadiazol-3-yl)amino]methyl}-4-fluoro-1H-benzimidazol-5-yl)tetrahydropyran-4-yl]-methanone Intermediate 26 (50.0 mg, 0.103 mmol) and AlPhos palladium complex (15.0 mg, 0.00769 mmol) were added to a vial, and the lid was sealed. The vial was placed under vacuum, then under nitrogen (3 cycles). TBME (0.21 mL) was added, followed by 3-bromo-5-isopropyl-1,2,4-oxadiazole (41.3 mg, 0.205 mmol) and DBU (0.047 mL, 0.31 mmol). The nitrogen line was removed, and the reaction mixture was stirred at 60° C. for 3 days. The reaction mixture was concentrated in vacuo, then purified by preparative basic reverse-phase HPLC and freeze-dried, to give the title compound (mixture of two tautomers in a 0.8:0.2 ratio) (7.2 mg, 12%) as an off-white solid. $\delta_H$ 400 MHz, DMSO-$d_6$) 12.94 (s, 0.2H), 12.68 (s, 0.8H), 7.55 (d, J 8.4 Hz, 0.8H), 7.44 (d, J 8.6 Hz, 0.2H), 7.32 (d, J 8.5 Hz, 0.8H), 7.25-7.18 (m, 1.2H), 4.57 (t, J 8.0 Hz, 1H), 4.24 (br s, 2H), 3.83-3.62 (m, 6H), 3.05 (hept, J 6.9 Hz, 1H), 2.32-2.23 (m, 2H), 2.22-2.12 (m, 1H), 2.11-1.90 (m, 5H), 1.87-1.68 (m, 2H), 1.56-1.42 (m, 2H), 1.35-1.21 (m, 7H). LCMS (Method 6): $[M+H]^+$ m/z 597.4, RT 1.72 minutes.

Example 6

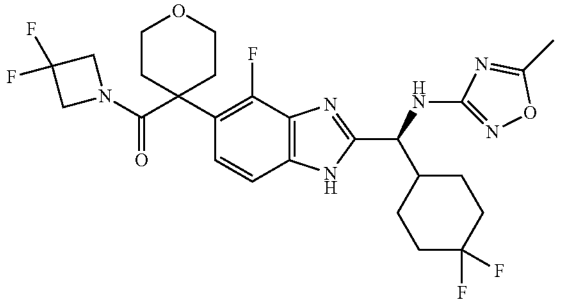 [SMILES: Cc1nc(N[C@H](c2nc3c(F)c(C4(C(=O)N5CC(F)(F)C5)CCOCC4)ccc3[nH]2)C2CCC(F)(F)CC2)no1]

(3,3-Difluoroazetidin-1-yl)[4-(2-{(S)-(4,4-difluoro-cyclohexyl)[(5-methyl-1,2,4-oxadiazol-3-yl)amino] methyl}-4-fluoro-1H-benzimidazol-5-yl)tetrahydro-pyran-4-yl]methanone Intermediate 26 (20.0 mg, 0.0411 mmol) and AlPhos palladium complex (8.0 mg, 0.0041 mmol) were added to a vial, and the lid was sealed. The vial was placed under vacuum, then under nitrogen (3 cycles). TBME (0.041 mL) was added, followed by 3-bromo-5-methyl-1,2,4-oxadiazole (7.8 mg, 0.045 mmol) and DBU (0.012 mL, 0.080 mmol). The nitrogen line was removed, and the reaction mixture was stirred at 60° C. for 3 days. The reaction mixture was diluted with DCM (10 mL) and washed with water (10 mL). The organic layer was passed through a phase separator and concentrated in vacuo. The residue was purified by preparative basic reverse-phase HPLC and freeze-dried to give the title compound (2.0 mg, 9%) as a white solid. LCMS (Method 6): $[M+H]^+$ m/z 569.4, RT 1.46 minutes. LCMS (Method 7): $[M+H]^+$ m/z 569.4, RT 1.45 minutes.

Example 7

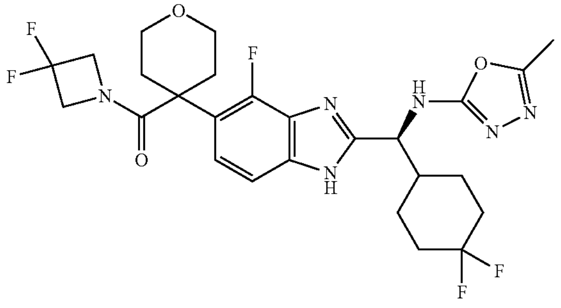 [SMILES: Cc1nnc(N[C@H](c2nc3c(F)c(C4(C(=O)N5CC(F)(F)C5)CCOCC4)ccc3[nH]2)C2CCC(F)(F)CC2)o1]

(3,3-Difluoroazetidin-1-yl)[4-(2-{(S)-(4,4-difluoro-cyclohexyl)[(5-methyl-1,3,4-oxadiazol-2-yl)amino] methyl}-4-fluoro-1H-benzimidazol-5-yl)tetrahydro-pyran-4-yl]methanone Intermediate 26 (20.0 mg, 0.0411 mmol), 2-bromo-5-methyl-1,3,4-oxadiazole (7.8 mg, 0.045 mmol) and AlPhos palladium complex (8.0 mg, 0.0041 mmol) were added to a vial, and the lid was sealed. The vial was placed under vacuum, then under nitrogen (3 cycles). TBME (0.041 mL) was added, followed by DBU (0.012 mL, 0.080 mmol). The nitrogen line was removed, and the reaction mixture was stirred at 60° C. for 3 days. The reaction mixture was diluted with DCM (10 mL) and washed with water (10 mL). The organic layer was passed through a phase separator and concentrated in vacuo. To a separate vial, Intermediate 26 (20.0 mg, 0.0411 mmol), 2-bromo-5-methyl-1,3,4-oxadiazole (7.8 mg, 0.045 mmol) and (tBu)PhCPhos Pd G4 (6.8 mg, 0.0082 mmol) were added, and the lid was sealed. The vial was placed under vacuum, then under nitrogen (3 cycles). Lithium bis(trimethylsilyl)amide (1M in THF, 0.082 mL, 0.082 mmol) was added, the nitrogen line was removed and the reaction mixture was stirred at 80° C. for 23.5 h. The reaction mixture was diluted with DCM (10 mL) and washed with water (10 mL). The organic layer was passed through a phase separator and concentrated in vacuo. The crude residue from both vials was combined and purified by preparative basic reverse-phase HPLC, and freeze-dried, to give the title compound (2.7 mg, 6%) as a white solid. LCMS (Method 6): $[M+H]^+$ m/z 569.3, RT 1.31 minutes. LCMS (Method 7): $[M+H]^+$ m/z 569.2, RT 1.32 minutes.

Example 8

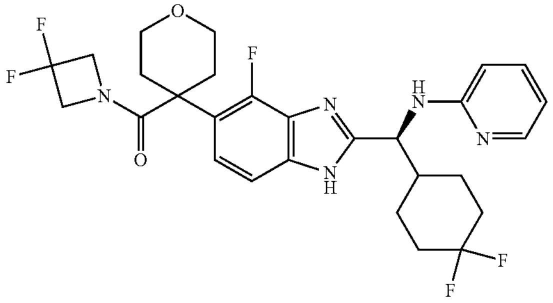 [SMILES: O=C(N1CC(F)(F)C1)C1(c2ccc3[nH]c([C@@H](Nc4ccccn4)C4CCC(F)(F)CC4)nc3c2F)CCOCC1]

(3,3-Difluoroazetidin-1-yl)(4-{2-[(S)-(4,4-difluoro-cyclohexyl)(pyridin-2-ylamino)-methyl]-4-fluoro-1H-benzimidazol-5-yl}tetrahydropyran-4-yl)methanone Intermediate 26 (52.0 mg, 0.107 mmol), cuprous iodide (2.0 mg, 0.011 mmol), potassium phosphate tribasic (51 mg, 0.24 mmol) and 2-bromopyridine (13 μL, 0.14 mmol) were added to a vial, and the lid was sealed. The vial was placed under vacuum, then under nitrogen (3 cycles). 1-Butanol (0.5 mL) and ethylene glycol (0.1 mL) were added. The nitrogen line was removed, and the reaction mixture was stirred at 100° C. for 2 days. The reaction mixture was diluted with EtOAc (6 mL) and washed with water (2 mL). The aqueous layer was re-extracted with EtOAc (6 mL). The combined organic layers were further washed with water (2×3 mL) and brine (3 mL), then dried with $Na_2SO_4$, filtered and concentrated in vacuo. The crude residue was purified by flash column chromatography ($SiO_2$), eluting with a gradient of 0-100% EtOAc in hexanes, and 0-30% MeOH in EtOAc, followed by flash column chromatography (KP-NH), eluting with a gradient of 0-50% MeOH in EtOAc, then freeze-dried, to give the title compound (mixture of two tautomers in a 0.8:0.2 ratio) (8.0 mg, 12%) as a pink solid. $\delta_H$ 400 MHz, DMSO-$d_6$) 12.91 (s, 0.2H), 12.65 (s, 0.8H), 7.91 (dd, J 5.2, 1.8 Hz, 1H), 7.42 (d, J 8.6 Hz, 0.2H), 7.37 (ddd, J 8.7, 7.0, 1.9 Hz, 1H), 7.29 (d, J 8.4 Hz, 0.8H), 7.24-7.17 (m, 1H), 7.08 (d, J 8.5 Hz, 0.8H), 7.00 (d, J 8.6 Hz, 0.2H), 6.72-6.66 (m, 1H), 6.51-6.45 (m, 1H), 5.31 (t, J 7.9 Hz, 1H), 4.25 (br s, 2H), 3.82-3.62 (m, 6H), 2.32-2.22 (m, 2H), 2.21-1.68 (m, 8H), 1.62-1.26 (m, 3H). LCMS (Method 6): $[M+H]^+$ m/z 564.4, RT 1.62 minutes.

Example 9

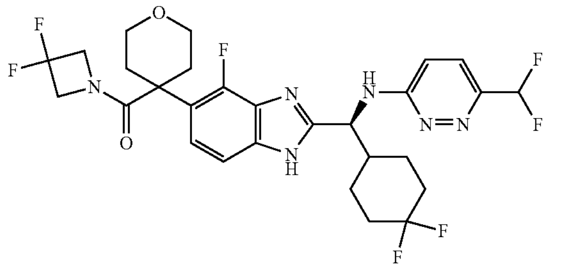 [SMILES: O=C(N1CC(F)(F)C1)C1(c2ccc3[nH]c([C@@H](Nc4ccc(C(F)F)nn4)C4CCC(F)(F)CC4)nc3c2F)CCOCC1]

(3,3-Difluoroazetidin-1-yl)(4-{2-[(S)-(4,4-difluorocyclohexyl) {[6-(difluoromethyl)-pyridazin-3-yl] amino}methyl]-4-fluoro-1H-benzimidazol-5-yl}tetrahydropyran-4-yl)-methanone TFA (50 μL, 0.66 mmol) was added to a solution of Intermediate 28 (10.0 mg, 0.0168 mmol) in DCM (1 mL) under nitrogen. The reaction mixture was stirred at r.t. for 16 h. Additional DCM (1 mL) was added, followed by TFA (50 μL, 0.66 mmol). The reaction mixture was stirred at r.t. for a further 6 h, then diluted with toluene (3 mL) and concentrated in vacuo. DCM (1 mL) and toluene (2 mL) were added, and the material was concentrated in vacuo. To a solution of the crude residue and DIPEA (20 μL, 0.12 mmol) in DCM (0.5 mL) was added HATU (9.0 mg, 0.023 mmol), followed by 3,3-difluoroazetidine hydrochloride (3.0 mg, 0.023 mmol). The reaction mixture was stirred overnight at r.t., then diluted with DCM (5 mL), saturated aqueous $NaHCO_3$ solution (4 mL) and water (2 mL), and stirred for a further 5 minutes. The layers were separated, and the aqueous layer was extracted with DCM (5 mL). The combined organic layers were dried with $Na_2SO_4$, then filtered and concentrated in vacuo. The crude residue was purified by flash column chromatography, eluting with a gradient of 50-100% EtOAc in hexanes, and 0-20% MeOH in EtOAc, and freeze-dried, to give the title compound (mixture of two tautomers in a 0.8:0.2 ratio) (9.9 mg, 96%) as a pale orange solid. $\delta_H$ (400 MHz, DMSO-$d_6$) 13.06 (s, 0.2H), 12.83 (s, 0.8H), 7.98 (d, J 8.2 Hz, 0.8H), 7.94 (d, J 8.3 Hz, 0.2H), 7.59-7.54 (m, 1H), 7.44 (d, J 8.5 Hz, 0.2H), 7.31 (d, J 8.6 Hz, 0.8H), 7.26-7.16 (m, 2H), 6.93 (t, J 54.7 Hz, 0.8H), 6.92 (t, J 54.7 Hz, 0.2H), 5.49 (t, J 7.8 Hz, 1H), 4.25 (br s, 2H), 3.89-3.60 (m, 6H), 2.32-2.17 (m, 3H), 2.15-1.73 (m, 7H), 1.66-1.55 (m, 1H), 1.54-1.31 (m, 2H). LCMS (Method 8): $[M+H]^+$ m/z 615.0, RT 1.91 minutes.

Example 10

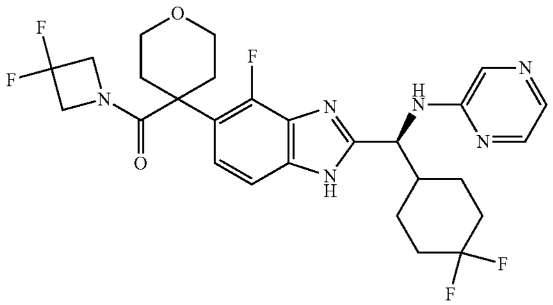 [SMILES: O=C(N1CC(F)(F)C1)C1(c2ccc3[nH]c([C@@H](Nc4cnccn4)C4CCC(F)(F)CC4)nc3c2F)CCOCC1]

(3,3-Difluoroazetidin-1-yl)(4-{2-[(S)-(4,4-difluorocyclohexyl)(pyrazin-2-ylamino)-methyl]-4-fluoro-1H-benzimidazol-5-yl}tetrahydropyran-4-yl)methanone TFA (50 μL, 0.66 mmol) was added to a solution of Intermediate 29 (31.0 mg, 0.0568 mmol) in DCM (1 mL) under nitrogen. The reaction mixture was stirred at r.t. for 5 h, then additional TFA (50 μL, 0.66 mmol) was added and stirring was continued overnight. The reaction mixture was diluted with DCM (1 mL) and toluene (3 mL) and concentrated in vacuo. The residue was diluted with DCM (1 mL) and toluene (3 mL) and concentrated in vacuo. To a solution of the crude residue and DIPEA (60 μL, 0.35 mmol) in DCM (1 mL) was added HATU (27 mg, 0.069 mmol). The reaction mixture was stirred for 5 minutes at r.t., then 3,3-difluoroazetidine hydrochloride (9.0 mg, 0.070 mmol) was added, and stirring was continued for a further 1.5 h. The reaction mixture was diluted with DCM (5 mL), saturated aqueous $NaHCO_3$ solution (4 mL) and water (2 mL). The layers were separated, and the aqueous layer was extracted with DCM (5 mL). The combined organic layers were dried with $Na_2SO_4$, then filtered and concentrated in vacuo. The crude residue was purified by flash column chromatography, eluting with a gradient of 50-100% EtOAc in hexanes, and 0-15% MeOH in EtOAc, then freeze-dried, to give the title compound (mixture of two tautomers in a 0.8:0.2 ratio) (18.5 mg, 58%) as a white solid. $\delta_H$ 400 MHz, DMSO-$d_6$) 12.95 (s, 0.2H), 12.71 (s, 0.8H), 8.15 (d, J 1.5 Hz, 0.8H), 8.14 (d, J 1.5 Hz, 0.2H), 7.91-7.85 (m, 1H), 7.73-7.66 (m, 1.8H), 7.64 (d, J 8.4 Hz, 0.2H), 7.44 (d, J 8.5 Hz, 0.2H), 7.30 (d, J 8.5 Hz, 0.8H), 7.25-7.18 (m, 1H), 5.28-5.21 (m, 1H), 4.25 (br s, 2H), 3.80-3.62 (m, 6H), 2.32-2.14 (m, 3H), 2.10-1.95 (m, 4H), 1.94-1.71 (m, 3H), 1.64-1.55 (m, 1H), 1.51-1.29 (m, 2H). LCMS (Method 6): $[M+H]^+$ m/z 565.2, RT 1.88 minutes.

Example 11

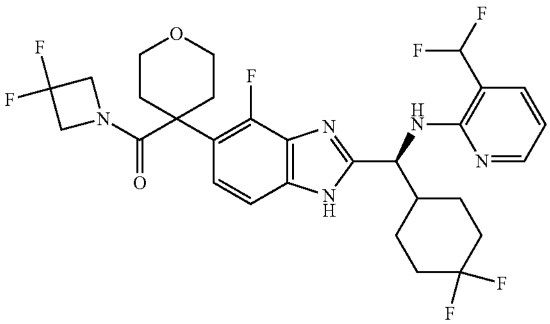 [SMILES: O=C(N1CC(F)(F)C1)C1(c2ccc3[nH]c([C@@H](Nc4ncccc4C(F)F)C4CCC(F)(F)CC4)nc3c2F)CCOCC1]

(3,3-Difluoroazetidin-1-yl)(4-{2-[(S)-(4,4-difluoro-cyclohexyl) {[3-(difluoromethyl)-pyridin-2-yl] amino}methyl]-4-fluoro-1H-benzimidazol-5-yl}tetrahydropyran-4-yl)-methanone Sodium tert-butoxide (19 mg, 0.20 mmol) and 2-bromo-3-(difluoromethyl)-pyridine (18 μL, 0.14 mmol) were added to a solution of Intermediate 31 (30.0 mg, 0.0487 mmol) in 1,4-dioxane (1 mL) under nitrogen. The reaction vessel was placed under vacuum and backfilled with nitrogen (3 cycles), then (tBu)PhCPhos Pd G3 (7 mg, 0.009 mmol) was added. The reaction vessel was again placed under vacuum and backfilled with nitrogen (1 cycle), then stirred at 75° C. for 3 days. The reaction mixture was diluted with DCM (2 mL) and washed with water (2 mL). The aqueous layer was extracted with DCM (1 mL). The combined organic layers were passed through a phase separator and concentrated in vacuo. The crude residue was purified by flash column chromatography, eluting with a gradient of 0-100% EtOAc in hexanes, and 0-20% MeOH in EtOAc. TFA (0.20 mL, 2.6 mmol) was added to the resulting yellow glass in DCM (1 mL) under nitrogen. The reaction mixture was stirred at r.t. overnight. Additional DCM (1.5 mL) and TFA (0.20 mL, 2.6 mmol) were added, and the reaction mixture was stirred for a further 5 h. More TFA (0.20 mL, 2.6 mmol) was added, and stirring was continued for an additional 1 h. The reaction mixture was concentrated in vacuo, then re-dissolved in DCM (5 mL), washed with saturated aqueous $NaHCO_3$ solution (8 mL), passed through a phase separator and concentrated in vacuo. The crude residue was purified by flash column chromatography, eluting with a gradient of 0-100% EtOAc in hexanes, and 0-30% MeOH in EtOAc, then freeze-dried, to give the title compound (mixture of two tautomers in a 0.7:0.3 ratio) (7.6 mg, 25%) as an off-white solid. $\delta_H$ 400 MHz, DMSO-$d_6$) 12.91 (s, 0.3H), 12.66 (s, 0.7H), 7.58-7.51 (m, 1H), 7.47 (d, J 8.6 Hz, 0.7H), 7.43 (d, J 8.5 Hz, 0.3H), 7.39 (d, J 8.6 Hz, 0.3H), 7.30 (d, J 8.5 Hz, 0.7H), 7.25-7.16 (m, 1H), 6.87-6.81 (m, 1H), 6.79-6.75 (m, 1H), 6.60 (t, J 55.4 Hz, 0.7H), 6.58 (t, J 55.4 Hz, 0.3H), 5.32 (t, J 7.8 Hz, 1H), 4.24 (br s, 2H), 3.83-3.57 (m, 6H), 2.31-2.13 (m, 3H), 2.12-1.95 (m, 4H), 1.95-1.69 (m, 3H), 1.65-1.53 (m, 1H), 1.52-1.22 (m, 2H). LCMS (Method 8): $[M+H]^+$ m/z 614.0, RT 2.19 minutes.

Example 12

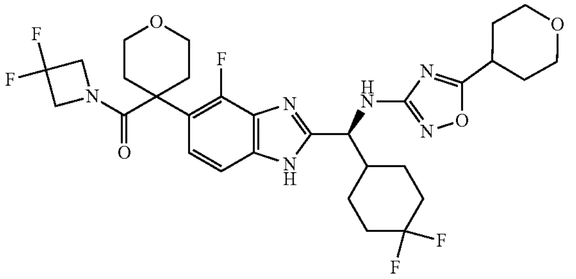 [SMILES: O=C(N1CC(F)(F)C1)C1(c2ccc3[nH]c([C@@H](Nc4noc(C5CCOCC5)n4)C4CCC(F)(F)CC4)nc3c2F)CCOCC1]

(3,3-Difluoroazetidin-1-yl)(4-{2-[(S)-(4,4-difluoro-cyclohexyl) {[5-(tetrahydropyran-4-yl)-1,2,4-oxadi-azol-3-yl]amino}methyl]-4-fluoro-1H-benzimidazol-5-yl}tetrahydropyran-4-yl)methanone A solution of sodium bicarbonate (132 mg, 1.57 mmol) in water (0.8 mL) was added to a solution of Intermediate 31 (387 mg, 0.628 mmol) in DCM (4 mL). The stirred mixture was cooled to 0° C., and a solution of cyanogen bromide (100 mg, 0.944 mmol) in DCM (2 mL) was added. The reaction mixture was stirred at 0° C. for 30 minutes, then the ice bath was removed and the reaction mixture was stirred at r.t. overnight. The reaction mixture was diluted with DCM (30 mL) and water (30 mL), and stirred vigorously for 20 minutes. The layers were separated, and the aqueous layer was re-extracted with DCM (30 mL). The combined organic layers were dried with $Na_2SO_4$, then filtered and concentrated in vacuo. To a solution of the resulting crude orange foam in DMF (6 mL) under an atmosphere of nitrogen were added sodium carbonate (60 mg, 0.57 mmol) and hydroxyammonium chloride (78 mg, 1.1 mmol). The reaction mixture was stirred at 80° C. for 4 h, then cooled to r.t. Toluene (5.5 mL) and pyridine (0.18 mL, 2.2 mmol, 100 mass %) were added, and the reaction mixture was cooled to 0° C. Tetrahydro-2H-pyran-4-carbonyl chloride (0.14 mL, 1.1 mmol) was added dropwise. Stirring was continued for a further 3 days, during which time the reaction mixture was allowed to warm to r.t. The reaction mixture was stirred at 60° C. for an additional 2 h, then diluted with toluene (10 mL) and concentrated in vacuo. The crude residue was evaporated from toluene (10 mL) on a further two occasions, then re-dissolved in DCM (30 mL) and washed with saturated aqueous $NaHCO_3$ solution (30 mL). The layers were separated, and the aqueous layer was extracted with DCM (30 mL). The combined organic layers were passed through a phase separator and concentrated in vacuo. The crude residue was purified by flash column chromatography, eluting with a gradient of 0-100% EtOAc in hexanes, and 0-20% MeOH in EtOAc, followed by preparative basic reverse-phase HPLC, then freeze-dried, to give the title compound (mixture of two tautomers in a 0.8:0.2 ratio) (57.0 mg, 14%) as a white solid. $\delta_H$ 400 MHz, DMSO-$d_6$) 12.94 (s, 0.2H), 12.69 (s, 0.8H), 7.61 (d, J 8.4 Hz, 0.8H), 7.50 (d, J 8.7 Hz, 0.2H), 7.44 (d, J 8.5 Hz, 0.2H), 7.32 (d, J 8.5 Hz, 0.8H), 7.26-7.18 (m, 1H), 4.57 (t, J 8.0 Hz, 1H), 4.25 (br s, 2H), 3.89-3.81 (m, 2H), 3.80-3.63 (m, 6H), 3.46-3.38 (m, 2H), 3.11 (tt, J 11.1, 3.8 Hz, 1H), 2.32-2.23 (m, 2H), 2.23-2.12 (m, 1H), 2.11-1.91 (m, 5H), 1.91-1.60 (m, 6H), 1.55-1.38 (m, 2H), 1.35-1.22 (m, 1H). LCMS (Method 6): $[M+H]^+$ m/z 639.4, RT 1.54 minutes.

Example 13

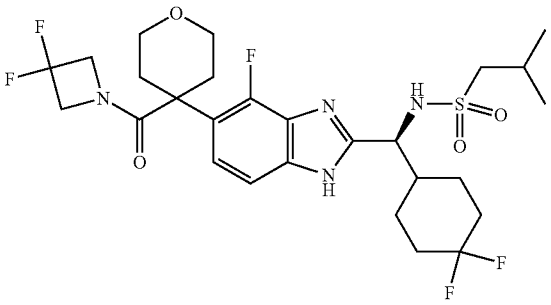 [SMILES: CC(C)CS(=O)(=O)N[C@H](c1nc2c(F)c(C3(C(=O)N4CC(F)(F)C4)CCOCC3)ccc2[nH]1)C1CCC(F)(F)CC1]

N—[(S)-{5-[4-(3,3-Difluoroazetidine-1-carbonyl) tetrahydropyran-4-yl]-4-fluoro-1H-benzimidazol-2-yl}(4,4-difluorocyclohexyl)methyl]-2-methylpropane-1-sulfonamide Pyridine (0.5 mL) was added to a vial containing Intermediate 26 (25.0 mg, 0.0514 mmol) and isobutanesulfonyl chloride (9.7 mg, 0.060 mmol). The reaction mixture was stirred at r.t. for 16 h, then diluted with pyridine (0.3 mL) and filtered. The residue was purified by preparative basic reverse-phase HPLC, then concentrated in vacuo using a Genevac EZ2 evaporator, to give the title compound (14.7 mg, 47%) as a solid. LCMS (Method 9): $[M+H]^+$ m/z 607.2, RT 2.31 minutes.

Example 14

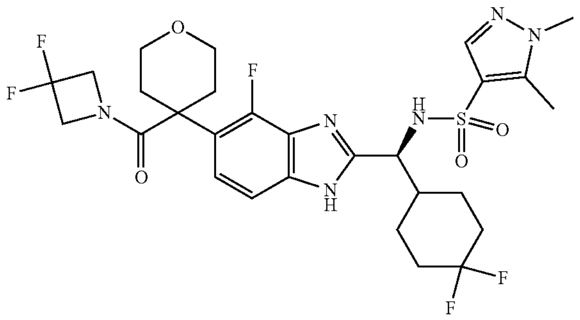 [SMILES: Cc1c(S(=O)(=O)N[C@H](c2nc3c(F)c(C4(C(=O)N5CC(F)(F)C5)CCOCC4)ccc3[nH]2)C2CCC(F)(F)CC2)cnn1C]

N—[(S)-{5-[4-(3,3-Difluoroazetidine-1-carbonyl) tetrahydropyran-4-yl]-4-fluoro-1H-benzimidazol-2-yl}(4,4-difluorocyclohexyl)methyl]-1,5-dimethylpyrazole-4-sulfonamide Pyridine (0.5 mL) was added to a vial containing Intermediate 26 (25.0 mg, 0.0514 mmol) and 1,5-dimethyl-1H-pyrazole-4-sulfonyl chloride (12.3 mg, 0.060 mmol). The reaction mixture was stirred at r.t. for 16 h, then diluted with pyridine (0.3 mL) and filtered. The residue was purified by preparative basic reverse-phase HPLC, then concentrated in vacuo using a Genevac EZ2 evaporator, to give the title compound (22.3 mg, 67%) as a solid. LCMS (Method 9): $[M+H]^+$ m/z 645.2, RT 2.08 minutes.

Example 15

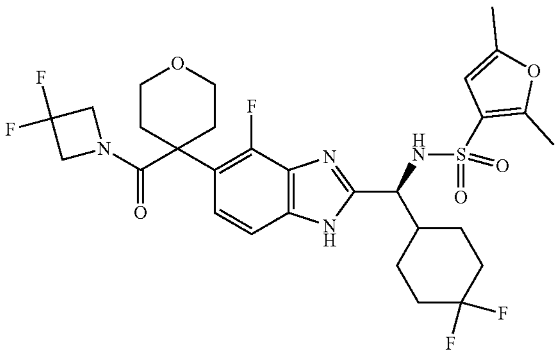 [SMILES: Cc1cc(S(=O)(=O)N[C@H](c2nc3c(F)c(C4(C(=O)N5CC(F)(F)C5)CCOCC4)ccc3[nH]2)C2CCC(F)(F)CC2)c(C)o1]

N—[(S)-{5-[4-(3,3-Difluoroazetidine-1-carbonyl) tetrahydropyran-4-yl]-4-fluoro-1H-benzimidazol-2-yl}(4,4-difluorocyclohexyl)methyl]-2,5-dimethylfuran-3-sulfonamide Pyridine (0.5 mL) was added to a vial containing Intermediate 26 (25.0 mg, 0.0514 mmol) and 2,5-dimethyl-3-furansulfonyl chloride (12.3 mg, 0.060 mmol). The reaction mixture was stirred at r.t. for 16 h, then diluted with pyridine (0.3 mL) and filtered. The residue was purified by preparative basic reverse-phase HPLC and concentrated in vacuo, using a Genevac EZ2 evaporator, to give the title compound (21.7 mg, 66%) as a solid. LCMS (Method 9): $[M+H]^+$ m/z 645.2, RT 2.34 minutes.

Example 16

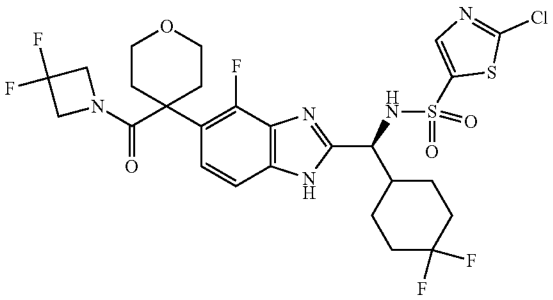 [SMILES: O=C(N1CC(F)(F)C1)C1(c2ccc3[nH]c([C@@H](NS(=O)(=O)c4cnc(Cl)s4)C4CCC(F)(F)CC4)nc3c2F)CCOCC1]

2-Chloro-N—[(S)-{5-[4-(3,3-difluoroazetidine-1-carbonyl)tetrahydropyran-4-yl]-4-fluoro-1H-benzimidazol-2-yl}(4,4-difluorocyclohexyl)methyl]thiazole-5-sulfonamide Pyridine (0.5 mL) was added to a vial containing Intermediate 26 (25.0 mg, 0.0514 mmol) and 2-chloro-1,3-thiazole-5-sulfonyl chloride (13.6 mg, 0.060 mmol). The reaction mixture was stirred at r.t. for 16 h, then diluted with pyridine (0.3 mL) and filtered. The residue was purified by preparative basic reverse-phase HPLC and concentrated in vacuo, using a Genevac EZ2 evaporator, to give the title compound (8.6 mg, 25%) as a solid. LCMS (Method 9): $[M+H]^+$ m/z 668.1, RT 2.34 minutes.

Example 17

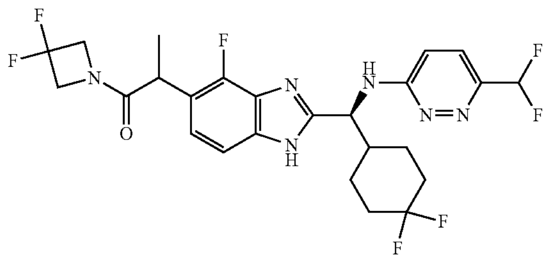 [SMILES: CC(C(=O)N1CC(F)(F)C1)c1ccc2[nH]c([C@@H](Nc3ccc(C(F)F)nn3)C3CCC(F)(F)CC3)nc2c1F]

1-(3,3-Difluoroazetidin-1-yl)-2-{2-[(S)-(4,4-difluorocyclohexyl){[6-(difluoromethyl)-pyridazin-3-yl]amino}methyl]-4-fluoro-1H-benzimidazol-5-yl}propan-1-one DIPEA (0.04 mL, 0.2 mmol) was added to a solution of Intermediate 36 (40.0 mg, 0.0929 mmol) and 3-chloro-6-(difluoromethyl)pyridazine (21.0 mg, 0.128 mmol) in 1,4-dioxane (0.8 mL). The reaction vessel was sealed and heated at 120° C. under microwave irradiation for 12 h. The reaction mixture was heated at 140° C. under microwave irradiation for a further 25 h, then concentrated in vacuo. The residue was purified by preparative basic reverse-phase HPLC and freeze-dried to give the title compound (mixture of two tautomers in a 0.8:0.2 ratio) (11.0 mg, 21%) as a white solid. $\delta_H$ 400 MHz, DMSO-$d_6$) 13.04 (s, 0.2H), 12.77 (s, 0.8H), 7.98 (d, J 8.1 Hz, 0.8H), 7.92 (d, J 8.3 Hz, 0.2H), 7.60-7.54 (m, 1H), 7.37 (dd, J 8.4, 1.5 Hz, 0.2H), 7.26 (dd, J 8.3, 0.9 Hz, 0.8H), 7.21-7.15 (m, 1H), 7.07 (ddd, J 6.5, 5.3, 2.8 Hz, 1H), 6.92 (t, J 54.7 Hz, 1H), 5.44 (q, J 7.4 Hz, 1H), 4.88-4.69 (m, 1H), 4.39-4.15 (m, 2H), 4.15-3.94 (m, 2H), 2.27-2.15 (m, 1H), 2.12-1.92 (m, 3H), 1.91-1.71 (m, 2H), 1.64-1.54 (m, 1H), 1.53-1.29 (m, 5H). LCMS (Method 6): $[M+H]^+$ m/z 559.4, RT 1.68 minutes.

The invention claimed is:

1. A compound of Formula (I) or an N-oxide thereof, or a pharmaceutically acceptable salt thereof:

(I)

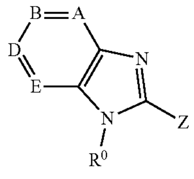

wherein

A represents C—$R^1$ or N;

B represents C—$R^2$ or N;

D represents C—$R^3$ or N;

E represents C—$R^4$ or N;

Z represents —$CH(R^5)N(H)S(O)_2R^6$ or —$CH(R^5)N(H)R^7$;

$R^0$ represents hydrogen or $C_{1-6}$ alkyl;

$R^1$, $R^2$, $R^3$ and $R^4$ independently represent hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2$Re, —$NHSO_2NR^bR^c$, —N═$S(O)R^bR^c$, —$COR^d$, —$CO_2R^d$, —$CONR^bR^c$, —$CON(OR^a)R^b$, —$SO_2NR^bR^c$ or —$S(O)(NR^c)R^a$; or $C_{1-6}$ alkyl, $C_{2-6}$ alkenyl, $C_{2-6}$ alkynyl, $C_{3-9}$ cycloalkyl, $C_{3-9}$ cycloalkyl($C_{1-6}$)alkyl, $C_{4-9}$ cycloalkenyl, aryl, aryl($C_{1-6}$)alkyl, $C_{3-7}$ heterocycloalkyl, $C_{3-7}$ heterocycloalkyl($C_{1-6}$)alkyl, $C_{3-7}$ hetero-cycloalkenyl, $C_{4-9}$ heterobicycloalkyl, heteroaryl or heteroaryl($C_{1-6}$)alkyl, any of which groups are optionally substituted by one or more substituents;

$R^5$ represents $C_{3-9}$ cycloalkyl, which group is optionally substituted by one or more substituents;

$R^{5a}$ represents $C_{3-7}$ cycloalkyl, $C_{4-9}$ bicycloalkyl, aryl, $C_{3-7}$ heterocycloalkyl or heteroaryl, any of which groups may be optionally substituted by one or more substituents; and $R^{5b}$ represents hydrogen or $C_{1-6}$ alkyl; or $R^{5a}$ and $R^{5b}$, when taken together with the carbon atom to which they are both attached, represent $C_{3-7}$ cycloalkyl, $C_{4-9}$ bicycloalkyl or $C_{3-7}$ heterocycloalkyl, any of which groups may be optionally substituted by one or more substituents;

$R^6$ represents —$OR^{6a}$ or —$NR^{6b}R^{6c}$; or $R^6$ represents $C_6$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups are optionally substituted by one or more substituents;

$R^{6a}$ represents $C_{1-6}$ alkyl; or $R^{6a}$ represents $C_{3-9}$ cycloalkyl, which group are optionally substituted by one or more substituents;

$R^{6b}$ represents hydrogen or $C_{1-6}$ alkyl;

$R^{6c}$ represents hydrogen or $C_{1-6}$ alkyl;

$R^7$ represents heteroaryl, which group is optionally substituted by one, two or three substituents independently selected from $C_{1-6}$ alkyl, difluoromethyl and tetrahydropyranyl;

$R^a$ represents trifluoromethyl; or $R^a$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups are optionally substituted by one or more substituents;

$R^b$ and $R^c$ independently represent hydrogen or trifluoromethyl; or $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups are optionally substituted by one or more substituents; or $R^b$ and $R^c$, when taken together with the nitrogen atom to which they are both attached represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups are optionally substituted by one or more substituents;

$R^d$ represents hydrogen; or $R^d$ represents $C_{1-6}$ alkyl, $C_{3-9}$ cycloalkyl, aryl, $C_{3-7}$ heterocycloalkyl or heteroaryl, any of which groups are optionally substituted by one or more substituents; and $R^e$ represents $C_{1-6}$ alkyl, aryl or heteroaryl, any of which groups are optionally substituted by one or more substituents.

2. The compound of claim 1 represented by Formula (IIA), an N-oxide thereof, or a pharmaceutically acceptable salt thereof:

(IIA)

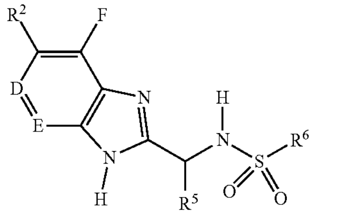

wherein

D, E, $R^2$, $R^5$ and $R^6$ are as defined in claim 1.

3. The compound of claim 1 wherein $R^6$ represents heteroaryl, which group is optionally substituted by one or more substituents.

4. The compound of claim 1 represented by Formula (IIB), an N-oxide thereof, or a pharmaceutically acceptable salt thereof:

(IIB)

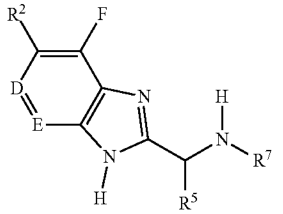

wherein

D, E, $R^2$, $R^5$ and $R^7$ are as defined in claim 1.

5. The compound of claim 1 wherein $R^2$ represents $C_{3-7}$ heterocycloalkyl, which group is optionally substituted by one or more substituents.

6. The compound of claim 1 wherein the compound is selected from:

(4-{2-[(S)-(Cyclopentyl){[6-(difluoromethyl)pyridazin-3-yl]amino}methyl]-4-fluoro-1H-benzimidazol-5-yl}tetrahydrofuran-3-yl)(3,3-difluoroazetidin-1-yl) methanone;

(1-Benzyl-4-{4-fluoro-2-[(S)-(imidazo[1,2-c]pyrimidin-5-ylamino)(4-methylcyclohexyl)-methyl]-1H-benzimidazol-5-yl}pyrrolidin-3-yl)(3,3-difluoroazetidin-1-yl) methanone;

N-[(S)-{5-[(3SR,4RS)-4-(3,3-Difluoroazetidine-1-carbonyl)tetrahydrofuran-3-yl]-4-fluoro-1H-benzimidazol-2-yl}[4-(trifluoromethyl)cyclohexyl]methyl]-2-ethyl-2H-pyrazole-3-sulfonamide;

(3,3-Difluoroazetidin-1-yl)(4-{2-[(S)-(4,4-difluorocyclohexyl)(isoxazolo[4,5-b]pyridin-3-ylamino)methyl]-4-fluoro-1H-benzimidazol-5-yl}tetrahydropyran-4-yl) methanone;

(3,3-Difluoroazetidin-1-yl)[4-(2-{(S)-(4,4-difluorocyclohexyl)[(5-isopropyl-1,2,4-oxadiazol-3-yl)amino] methyl}-4-fluoro-1H-benzimidazol-5-yl)tetrahydropyran-4-yl]-methanone;

(3,3-Difluoroazetidin-1-yl)[4-(2-{(S)-(4,4-difluorocyclohexyl)[(5-methyl-1,2,4-oxadiazol-3-yl)amino] methyl}-4-fluoro-1H-benzimidazol-5-yl)tetrahydropyran-4-yl]methanone;

(3,3-Difluoroazetidin-1-yl)[4-(2-{(S)-(4,4-difluorocyclohexyl)[(5-methyl-1,3,4-oxadiazol-2-yl)amino] methyl}-4-fluoro-1H-benzimidazol-5-yl)tetrahydropyran-4-yl]methanone;

(3,3-Difluoroazetidin-1-yl)(4-{2-[(S)-(4,4-difluorocyclohexyl)(pyridin-2-ylamino)-methyl]-4-fluoro-1H-benzimidazol-5-yl}tetrahydropyran-4-yl)methanone;

(3,3-Difluoroazetidin-1-yl)(4-{2-[(S)-(4,4-difluorocyclohexyl){[6-(difluoromethyl)-pyridazin-3-yl] amino}methyl]-4-fluoro-1H-benzimidazol-5-yl}tetrahydropyran-4-yl)-methanone;

(3,3-Difluoroazetidin-1-yl)(4-{2-[(S)-(4,4-difluorocyclohexyl)(pyrazin-2-ylamino)-methyl]-4-fluoro-1H-benzimidazol-5-yl}tetrahydropyran-4-yl)methanone;

(3,3-Difluoroazetidin-1-yl)(4-{2-[(S)-(4,4-difluorocyclohexyl){[3-(difluoromethyl)-pyridin-2-yl] amino}methyl]-4-fluoro-1H-benzimidazol-5-yl}tetrahydropyran-4-yl)-methanone;

(3,3-Difluoroazetidin-1-yl)(4-{2-[(S)-(4,4-difluorocyclohexyl){[5-(tetrahydropyran-4-yl)-1,2,4-oxadiazol-3-yl]amino}methyl]-4-fluoro-1H-benzimidazol-5-yl}tetrahydropyran-4-yl)methanone;

N-[(S)-{5-[4-(3,3-Difluoroazetidine-1-carbonyl)tetrahydropyran-4-yl]-4-fluoro-1H-benzimidazol-2-yl}(4,4-difluorocyclohexyl)methyl]-2-methylpropane-1-sulfonamide;

N-[(S)-{5-[4-(3,3-Difluoroazetidine-1-carbonyl)tetrahydropyran-4-yl]-4-fluoro-1H-benzimidazol-2-yl}(4,4-difluorocyclohexyl)methyl]-1,5-dimethylpyrazole-4-sulfonamide;

N-[(S)-{5-[4-(3,3-Difluoroazetidine-1-carbonyl)tetrahydropyran-4-yl]-4-fluoro-1H-benzimidazol-2-yl}(4,4-difluorocyclohexyl)methyl]-2,5-dimethylfuran-3-sulfonamide;

2-Chloro-N-[(S)-{5-[4-(3,3-difluoroazetidine-1-carbonyl)tetrahydropyran-4-yl]-4-fluoro-1H-benzimidazol-2-yl}(4,4-difluorocyclohexyl)methyl]thiazole-5-sulfonamide; and 1-(3,3-Difluoroazetidin-1-yl)-2-{2-[(S)-(4,4-difluorocyclohexyl){[6-(difluoromethyl)-pyridazin-3-yl] amino}methyl]-4-fluoro-1H-benzimidazol-5-yl}propan-1-one.

7. A pharmaceutical composition comprising the compound of Formula (I) of claim 1, an N-oxide thereof, or a pharmaceutically acceptable salt thereof, and a pharmaceutically acceptable carrier.

8. A pharmaceutical composition as claimed in claim 7 further comprising an additional pharmaceutically active ingredient.

9. A method of treating a disorder for which the administration of a modulator of IL-17 function is indicated, comprising administering to a patient in need of such treatment an effective amount of the compound of Formula (I) of claim 1, an N-oxide thereof, or a pharmaceutically acceptable salt thereof.

10. A method for the treatment of an inflammatory or autoimmune disorder, which comprises administering to a patient in need of such treatment an effective amount of the compound of Formula (I) of claim 1, an N-oxide thereof, or a pharmaceutically acceptable salt thereof.

11. The compound of claim 4 wherein $R^2$ represents $C_{3-7}$ heterocycloalkyl, which group is optionally substituted by one or more substituents.

12. The compound of claim 1 wherein $R^2$ represents $C_{1-6}$ alkyl or $C_{3-7}$ heterocycloalkyl, which groups are optionally substituted by one or more substituents.

13. The compound of claim 1 wherein $R^2$ represents $C_{1-6}$ alkyl or $C_{3-7}$ heterocycloalkyl, which groups are optionally substituted by one, two or three substituents independently selected from benzyl and difluoroazetidinyl.

14. The compound of claim 1 wherein $R^5$ represents $C_{3-9}$ cycloalkyl, which group is optionally substituted by one, two or three substituents independently selected from halogen, $C_{1-6}$ alkyl and trifluoromethyl.

* * * * *